United States Patent
Grandal et al.

(10) Patent No.: US 11,834,503 B2
(45) Date of Patent: Dec. 5, 2023

(54) ANTI-LAG-3 ANTIBODIES AND COMPOSITIONS

(71) Applicant: Chia Tai Tianqing Pharmaceutical Group Co., Ltd., Lianyungang (CN)

(72) Inventors: Michael Monrad Grandal, Ballerup (DK); Vikram Kjøller Bhatia, Charlottenlund (DK); Torben Gjetting, Jyllinge (DK); Camilla Fröhlich, København Ø (DK); Gunther Roland Galler, Jyllinge (DK); Michael Kragh, Copenhagen N (DK); Ivan David Horak, West Orange, NJ (US); Thomas Bouquin, Alleroed (DK); Mikkel Wandahl Pedersen, Alleroed (DK)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 0 days.

(21) Appl. No.: 17/834,497

(22) Filed: Jun. 7, 2022

(65) Prior Publication Data

US 2022/0363757 A1 Nov. 17, 2022

Related U.S. Application Data

(62) Division of application No. 16/340,855, filed as application No. PCT/EP2017/076188 on Oct. 13, 2017, now Pat. No. 11,390,676.

(60) Provisional application No. 62/407,678, filed on Oct. 13, 2016.

(51) Int. Cl.
| | | |
|---|---|---|
| *C07K 16/28* | (2006.01) | |
| *C12N 15/85* | (2006.01) | |
| *A61P 37/04* | (2006.01) | |
| *A61P 35/00* | (2006.01) | |
| *A61K 9/00* | (2006.01) | |

(52) U.S. Cl.
CPC ........ *C07K 16/2803* (2013.01); *A61K 9/0019* (2013.01); *A61P 35/00* (2018.01); *A61P 37/04* (2018.01); *C12N 15/85* (2013.01)

(58) Field of Classification Search
CPC ............ C07K 16/2803; C07K 2317/21; C07K 2317/24; C07K 2317/33; C07K 2317/34; C07K 2317/52; C07K 2317/71; C07K 2317/76; C07K 16/00–468; C07K 16/2818; C07K 16/2827; A61K 9/0019; A61K 39/395; A61P 35/00; A61P 37/04; A61P 37/00; A61P 43/00; C12N 15/85

See application file for complete search history.

(56) References Cited

U.S. PATENT DOCUMENTS

| | | | | |
|---|---|---|---|---|
| 9,044,460 | B2 * | 6/2015 | Bukhalid | ............... A61P 35/00 |
| 10,000,564 | B2 * | 6/2018 | Murphy | ................. A61P 37/08 |
| 11,390,676 | B2 * | 7/2022 | Grandal | ................. A61P 37/04 |
| 2007/0071675 | A1 | 3/2007 | Wu et al. | |
| 2011/0070238 | A1 | 3/2011 | Triebel et al. | |
| 2014/0093511 | A1 | 4/2014 | Lonberg et al. | |
| 2015/0259420 | A1 * | 9/2015 | Triebel | .................... A61P 15/00 |
| | | | | 435/69.6 |
| 2020/0407444 | A1 | 12/2020 | Lindsted et al. | |
| 2022/0380470 | A1 | 12/2022 | Lindsted et al. | |

FOREIGN PATENT DOCUMENTS

| | | |
|---|---|---|
| WO | WO 95/030750 | 12/1995 |
| WO | WO 01/077342 | 10/2001 |
| WO | WO 2008/132601 A1 | 11/2008 |
| WO | WO 2010/019570 A2 | 2/2010 |
| WO | WO 2014/008218 A1 | 1/2014 |
| WO | WO 2014/140180 A1 | 9/2014 |
| WO | WO 2015/042246 A1 | 3/2015 |
| WO | WO 2015/048312 A1 | 4/2015 |
| WO | WO 2015/138920 A1 | 9/2015 |
| WO | WO 2016/028672 A1 | 2/2016 |
| WO | WO 2016/126858 A1 | 8/2016 |
| WO | WO 2016/200782 A1 | 12/2016 |
| WO | WO 2017/198741 A1 | 11/2017 |

OTHER PUBLICATIONS

Edwards et al. 2003. The remarkable flexibility of the human antibody repertoire; isolation of over one thousand different antibodies to a single protein, BlyS. Journal of Molecular Biology 334:103-118 (Year: 2003).*
Berglund et al., 2008, Protein Science, 17:606-613 (Year: 2008).*
Murphy et al. (Journal of Immunological Methods, vol. 463, p. 127-133, 2018 (Year: 2018).*
Chen L, Zhu C, Guo H, Li R, Zhang L, Xing Z, Song Y, Zhang Z, Wang F, Liu X, Zhang Y, Ma RZ, Wang F. Epitope-directed antibody selection by site-specific photocrosslinking. Sci Adv. Apr. 1, 2020;6(14):eaaz7825. (Year: 2020).*
Andrews et al., "LAG3 (CD223) as a cancer immunotherapy target," Immunol Rev 276(1):80-96 (2017).
Anonymous, "Anti-LAG-3 or Urelumab Alone and in Combination with Nivolumab in Treating Patients with Recurrent Glioblastoma—Full Text View," ClinicalTrials.gov (2016).
Huard et al., "Characterization of the major histocompatibility complex class II binding site on LAG-3 protein," Proc Natl Acad Sci USA 94:5744-5749 (1997).
Isaacs et al., "Therapy with monoclonal antibodies. II. The contribution of Fc gamma receptor binding and the influence of C(H)1 and C(H)3 domains on in vivo effector function," J Immunol. 161(8):3862-9 (1998).

(Continued)

*Primary Examiner* — Jessica H Roark
(74) *Attorney, Agent, or Firm* — Steptoe & Johnson LLP; Z. Ying Li; Wyan-Ching M. Lee

(57) ABSTRACT

This invention relates to anti-LAG-3 antibodies and methods of using them in treating diseases and conditions that benefit from modulating LAG-3 activity, e.g., cancer.

20 Claims, 11 Drawing Sheets
Specification includes a Sequence Listing.

(56) References Cited

OTHER PUBLICATIONS

Jing et al., "Combined immune checkpoint protein blockade and low dose whole body irradiation as immunotherapy for myeloma," J Immunother Cancer 3(1):2 (2015).
Jones et al., "Replacing the complementarity-determining regions in a human antibody with those from a mouse," Nature 321 (6069):522-5 (1986).
Kehry, "Targeting PD-1, TIM-3 and LAG-3 in combination for improved Immunotherapy Combinations," Journal for Immunotherapy of Cancer (2015) [https://www.tesarobio.com/application/files/3014/7552/4272/AACRApr2015.pdf].
Mariuzza et al., "The structural basis of antigen-antibody recognition," Annu Rev Biophys Biophys Chem. 16:139-59 (1987).
Meijer et al., "Isolation of Human Antibody Repertoires with Preservation of the Natural Heavy and Light Chain Pairing," J Mol Biol. 358(3):764-772 (2006).
Nishibori et al., "Humanization of chicken monoclonal antibody using phage-display system," Mol Immunol 43(6):634-42 (2006).
Osborn et al., "High-affinity IgG antibodies develop naturally in Ig-knockout rats carrying germline human IgH/IgK/Igλ loci bearing the rat CH region," J Immunol 190(4):1481-1490 (2013).
Padlan, "Advances in Protein Chemistry," 49:57-133 (1996).
Pan et al., "Blocking neuropilin-1 function has an additive effect with anti-VEGF to inhibit tumor growth," Cancer Cell 11(1):53-67 (2007).
Spiess et al., "Alternative molecular formats and therapeutic applications for bispecific antibodies," Mol Immunol. 67(2 Pt A):95-106 (2015).
Triebel, "LAG-3: a regulator of T-cell and DC responses and its use in therapeutic vaccination," Trends Immunol 24(12):619-22 (2003).
U.S. Appl. No. 16/500,918, filed Oct. 4, 2019, Trine Lindsted et al.
U.S. Appl. No. 17/834,554, filed Jun. 7, 2022, Trina Lindsted et al.

* cited by examiner

ANTI-LAG-3 ANTIBODIES AND COMPOSITIONS

CROSS-REFERENCE TO RELATED APPLICATIONS

This application is a divisional application of U.S. patent application Ser. No. 16/340,855, filed on Apr. 10, 2019, which is a national stage application under 35 U.S.C. § 371 of International Patent Application PCT/EP2017/076188, filed on Oct. 13, 2017, which claims priority from U.S. Provisional Patent Application 62/407,678, filed on Oct. 13, 2016. The disclosures of those applications are incorporated by reference herein in their entirety.

SEQUENCE LISTING

The instant application contains a Sequence Listing which has been submitted electronically in ASCII format and is hereby incorporated by reference in its entirety. The electronic copy of the Sequence Listing, created on Oct. 5, 2017, is named 022675_WO057_SL.txt and is 64,693 bytes in size.

BACKGROUND OF THE INVENTION

LAG-3 (lymphocyte-activation gene 3), also known as CD223, is an immunoglobulin superfamily protein that functions as an immune checkpoint receptor. The mature protein is a 503-amino acid type I transmembrane protein with four extracellular Ig-like domains. It is expressed on various types of cells including activated T cells, T regulatory (Treg) cells, natural killer cells, B cells and plasmacytoid dendritic cells. Information on sequence data, exon/intron organization, and the chromosomal localization of LAG-3 indicates that it is closely related to CD4. Similar to CD4, LAG-3 binds MHC class II molecules, although with a higher affinity and at a distinct site compared to CD4.

LAG-3 is a co-inhibitory receptor that is thought to regulate T cell proliferation, activation and homeostasis in a manner similar to CTLA-4 and PD-1. Upon ligand binding to the extracellular domain, LAG-3 exerts its effect through subsequent signaling via the cytoplasmic domain. The best characterized ligand for LAG-3 is MHC class II (MHCII), but other LAG-3 ligands have been described, including LSECtin.

LAG-3 has no classical ITIM or ITSM motifs, but has a conserved KIEELE motif (SEQ ID NO: 73) which is thought to be indispensable for accomplishing its inhibitory effect on T-cell activity. The exact mechanism by which LAG-3 affects T-cell activity is poorly understood. LAG-3 inhibits T cell expansion by blocking entry of activated T-cells into the growth phase of the cell cycle, resulting in the accumulation of cells in the S-phase. LAG-3 is also thought to play a role in enhancing the suppressive activity of regulatory T-cells and in modulating dendritic cell function. Cancer cells have the ability to upregulate expression of MHCII, which binds LAG-3 on effector T-cells, thus inhibiting their activity and inducing tumor immune escape.

In view of the critical role of LAG-3 as an immune modulator, there is a need for new and improved immune therapies that target LAG-3 to treat cancers and certain disorders of the immune system.

SUMMARY OF THE INVENTION

The present invention is directed to novel recombinant antibodies targeting LAG-3, as well as pharmaceutical compositions comprising one or more of these antibodies, and use of the antibodies and pharmaceutical compositions for enhancing immunity in a patient, and for treatment of cancers originating from tissues such as skin, lung, intestine, colon, ovary, brain, prostate, kidney, soft tissues, the hematopoietic system, head and neck, liver, bladder, breast, stomach, uterus and pancreas. Compared to currently available treatments for such cancers, including antibody treatments, it is contemplated that the antibodies of the invention may provide a superior clinical response either alone or in combination with another cancer therapeutic, such as an antibody targeting another immune checkpoint protein.

In one embodiment, the present invention provides an anti-LAG-3 antibody or an antigen-binding portion thereof, wherein the anti-LAG-3 antibody is any of the antibodies referred to herein as antibody 15646, 15532, 15723, 15595, 15431, 15572 or 15011, or a variant thereof, where the variant may, e.g., be of a different isotype or isotype subclass and/or contain certain minimum amino acid changes relative to antibody 15646, 15532, 15723, 15595, 15431, 15572 or 15011 without losing the antigen-binding specificity of the parent antibody.

In one embodiment, the anti-LAG-3 antibody competes for binding to human LAG-3 with an antibody whose heavy chain (H) CDR1-3 and light chain (L) CDR1-3 are the same as or derived from the H-CDR1-3 and L-CDR1-3 of antibody 15646, 15532, 15723, 15595, 15431, 15572 or 15011.

In one embodiment, the anti-LAG-3 antibody binds to the same epitope of human LAG-3 as an antibody whose heavy chain (H) CDR1-3 and light chain (L) CDR1-3 are the same as or derived from the H-CDR1-3 and L-CDR1-3 of antibody 15646, 15532, 15723, 15595, 15431, 15572 or 15011.

In one embodiment, the anti-LAG-3 antibody comprises an H-CDR3 comprising the H-CDR3 amino acid sequence of antibody 15646, 15532, 15723, 15595, 15431, 15572 or 15011.

In one embodiment, the anti-LAG-3 antibody comprises H-CDR1-3 comprising the H-CDR1-3 sequences, respectively, of antibody 15646, 15532, 15723, 15595, 15431, 15572 or 15011.

In one embodiment, the anti-LAG-3 antibody comprises an L-CDR3 comprising the L-CDR3 amino acid sequence of antibody 15646, 15532, 15723, 15595, 15431, 15572 or 15011.

In one embodiment, the anti-LAG-3 antibody comprises L-CDR1-3 comprising the L-CDR1-3 sequences, respectively, of antibody 15646, 15532, 15723, 15595, 15431, 15572 or 15011.

In one embodiment, the anti-LAG-3 antibody comprises the H-CDR3 and L-CDR3 amino acid sequences of antibody 15646, 15532, 15723, 15595, 15431, 15572 or 15011.

In one embodiment, the anti-LAG-3 antibody comprises the H-CDR1-3 and L-CDR1-3 amino acid sequences of antibody 15646, 15532, 15723, 15595, 15431, 15572 or 15011.

In one embodiment, the anti-LAG-3 antibody competes for binding to human LAG-3 with antibody 15646, 15532, 15723, 15595, 15431, 15572 or 15011.

In one embodiment, the anti-LAG-3 antibody binds to the same epitope of human LAG-3 as antibody 15646, 15532, 15723, 15595, 15431, 15572 or 15011.

In one embodiment, the anti-LAG-3 antibody comprises a heavy chain complementarity-determining region (H-CDR) 3 comprising the amino acid sequence of SEQ ID NO: 37, 43, 46, 50, 55, 58, or 64.

In one embodiment, the anti-LAG-3 antibody comprises H-CDR1-3 comprising the amino acid sequences, respectively, of SEQ ID NOs: 35-37; 41-43; 35, 42, and 46; 48-50; 53-55; 56-58; or 62-64.

In one embodiment, the anti-LAG-3 antibody has a heavy chain variable domain (VH) that is at least 90% (e.g., at least 92%, at least 95%, at least 98%, or at least 99%) identical in sequence to the VH amino acid sequence of SEQ ID NO: 3, 7, 11, 15, 19, 23 or 27.

In one embodiment, the anti-LAG-3 antibody has a VH that comprises SEQ ID NO: 3, 7, 11, 15, 19, 23 or 27.

In one embodiment, the anti-LAG-3 antibody has a heavy chain (HC) that comprises the VH amino acid sequence of SEQ ID NO: 3, 7, 11, 15, 19, 23 or 27 and the heavy chain constant region amino acid sequence of SEQ ID NO: 30.

In one embodiment, the anti-LAG-3 antibody comprises a light chain complementarity-determining region (L-CDR) 3 comprising the amino acid sequence of SEQ ID NO: 40, 52, 61, or 67.

In one embodiment, the anti-LAG-3 antibody comprises L-CDR1-3 comprising the amino acid sequences, respectively, of SEQ ID NOs: 38-40; 44, 45, and 40; 44, 47, and 40; 51, 47, and 52; 59-61; or 65-67.

In one embodiment, the anti-LAG-3 antibody has a light chain variable domain (VL) that is at least 90% (e.g., at least 92%, at least 95%, at least 98%, or at least 99%) identical in sequence to the VL amino acid sequence of SEQ ID NO: 4, 8, 12, 16, 20, 24 or 28.

In one embodiment, the anti-LAG-3 antibody has a VL that comprises SEQ ID NO: 4, 8, 12, 16, 20, 24 or 28.

In one embodiment, the anti-LAG-3 antibody has a light chain (LC) that comprises the VL amino acid sequence of SEQ ID NO: 4, 8, 12, 16, 20, 24 or 28 and the light chain constant region amino acid sequence of SEQ ID NO: 32 or 34.

In one embodiment, the anti-LAG-3 antibody comprises the H-CDR3 and L-CDR3 amino acid sequences of SEQ ID NOs: 37 and 40; 43 and 40; 46 and 40; 50 and 52; 55 and 40; 58 and 61; or 64 and 67; respectively.

In certain embodiments, the anti-LAG-3 antibody or antigen-binding portion of the invention comprises the H-CDR1-3 and L-CDR1-3 amino acid sequences of:
a) SEQ ID NOs: 35, 36, 37, 38, 39, and 40, respectively;
b) SEQ ID NOs: 41, 42, 43, 44, 45, and 40, respectively;
c) SEQ ID NOs: 35, 42, 46, 44, 47, and 40, respectively;
d) SEQ ID NOs: 48, 49, 50, 51, 47, and 52, respectively;
e) SEQ ID NOs: 53, 54, 55, 44, 45, and 40, respectively;
f) SEQ ID NOs: 56, 57, 58, 59, 60, and 61, respectively; or
g) SEQ ID NOs: 62, 63, 64, 65, 66, and 67, respectively.

In certain embodiments, the anti-LAG-3 antibody or antigen-binding portion thereof of the invention:
a) has a VH that is at least 90% (e.g, at least 92%, at least 95%, at least 98%, or at least 99%) identical in sequence to the amino acid sequence of SEQ ID NO: 3, and a VL that is at least 90% (e.g, at least 92%, at least 95%, at least 98%, or at least 99%) identical in sequence to the amino acid sequence of SEQ ID NO: 4;
b) has a VH that is at least 90% (e.g, at least 92%, at least 95%, at least 98%, or at least 99%) identical in sequence to the amino acid sequence of SEQ ID NO: 7, and a VL that is at least 90% (e.g, at least 92%, at least 95%, at least 98%, or at least 99%) identical in sequence to the amino acid sequence of SEQ ID NO: 8;
c) has a VH that is at least 90% (e.g, at least 92%, at least 95%, at least 98%, or at least 99%) identical in sequence to the amino acid sequence of SEQ ID NO: 11, and a VL that is at least 90% (e.g, at least 92%, at least 95%, at least 98%, or at least 99%) identical in sequence to the amino acid sequence of SEQ ID NO: 12;
d) has a VH that is at least 90% (e.g., at least 92%, at least 95%, at least 98%, or at least 99%) identical in sequence to the amino acid sequence of SEQ ID NO: 15, and a VL that is at least 90% (e.g, at least 92%, at least 95%, at least 98%, or at least 99%) identical in sequence to the amino acid sequence of SEQ ID NO: 16;
e) has a VH that is at least 90% (e.g., at least 92%, at least 95%, at least 98%, or at least 99%) identical in sequence to the amino acid sequence of SEQ ID NO: 19, and a VL that is at least 90% (e.g, at least 92%, at least 95%, at least 98%, or at least 99%) identical in sequence to the amino acid sequence of SEQ ID NO: 20;
f) has a VH that is at least 90% (e.g., at least 92%, at least 95%, at least 98%, or at least 99%) identical in sequence to the amino acid sequence of SEQ ID NO: 23, and a VL that is at least 90% (e.g, at least 92%, at least 95%, at least 98%, or at least 99%) identical in sequence to the amino acid sequence of SEQ ID NO: 24; or
g) has a VH that is at least 90% (e.g., at least 92%, at least 95%, at least 98%, or at least 99%) identical in sequence to the amino acid sequence of SEQ ID NO: 27, and a VL that is at least 90% (e.g, at least 92%, at least 95%, at least 98%, or at least 99%) identical in sequence to the amino acid sequence of SEQ ID NO: 28.

In certain embodiments, the anti-LAG-3 antibody or antigen-binding portion of the invention:
a) has a VH that comprises or consists of the amino acid sequence of SEQ ID NO: 3, and a VL that comprises or consists of the amino acid sequence of SEQ ID NO: 4;
b) has a VH that comprises or consists of the amino acid sequence of SEQ ID NO: 7, and a VL that comprises or consists of the amino acid sequence of SEQ ID NO: 8;
c) has a VH that comprises or consists of the amino acid sequence of SEQ ID NO: 11, and a VL that comprises or consists of the amino acid sequence of SEQ ID NO: 12;
d) has a VH that comprises or consists of the amino acid sequence of SEQ ID NO: 15, and a VL that comprises or consists of the amino acid sequence of SEQ ID NO: 16;
e) has a VH that comprises or consists of the amino acid sequence of SEQ ID NO: 19, and a VL that comprises or consists of the amino acid sequence of SEQ ID NO: 20;
f) has a VH that comprises or consists of the amino acid sequence of SEQ ID NO: 23, and a VL that comprises or consists of the amino acid sequence of SEQ ID NO: 24; or
g) has a VH that comprises or consists of the amino acid sequence of SEQ ID NO: 27, and a VL that comprises or consists of the amino acid sequence of SEQ ID NO: 28.

In certain embodiments, the anti-LAG-3 antibody:
a) has an LC that comprises or consists of the amino acid sequences of SEQ ID NOs: 4 and 34; and an HC that comprises or consists of the amino acid sequences of SEQ ID NOs: 3 and 30;

b) has an LC that comprises or consists of the amino acid sequences of SEQ ID NOs: 8 and 34; and an HC that comprises or consists of the amino acid sequences of SEQ ID NOs: 7 and 30;
c) has an LC that comprises or consists of the amino acid sequences of SEQ ID NOs: 12 and 34; and an HC that comprises or consists of the amino acid sequences of SEQ ID NOs: 11 and 30;
d) has an LC that comprises or consists of the amino acid sequences of SEQ ID NOs: 16 and 34; and an HC that comprises or consists of the amino acid sequences of SEQ ID NOs: 15 and 30;
e) has an LC that comprises or consists of the amino acid sequences of SEQ ID NOs: 20 and 34; and an HC that comprises or consists of the amino acid sequences of SEQ ID NOs: 19 and 30;
f) has an LC that comprises or consists of the amino acid sequences of SEQ ID NOs: 24 and 34; and an HC that comprises or consists of the amino acid sequences of SEQ ID NOs: 23 and 30; or
g) has an LC that comprises or consists of the amino acid sequences of SEQ ID NOs: 28 and 32; and an HC that comprises or consists of the amino acid sequences of SEQ ID NOs: 27 and 30.

In some embodiments, the anti-LAG-3 antibody or antigen-binding portion of the invention has at least one of the following properties:
a) at a concentration of 20 µg/mL, reduces the binding of human LAG-3 to human MHC class II on A375 cells by greater than 85% compared to a negative control antibody as determined by a flow cytometric competition assay;
b) at a concentration of 20 µg/mL, reduces the binding of human LAG-3 to human MHC class II on A375 cells to between 35% and 85% compared to a negative control antibody as determined by a flow cytometric competition assay;
c) blocks binding between human LAG-3 expressed on Jurkat cells and human MHC class II expressed on Raji cells;
d) binds to human LAG-3 with an $EC_{50}$ of 0.1 nM or less as measured by flow cytometry;
e) binds to cynomolgus LAG-3 with an $EC_{50}$ of 0.3 nM or less as measured by flow cytometry;
f) binds to human LAG-3 with a $K_D$ of $3.0 \times 10^{-8}$ or less as measured by surface plasmon resonance;
g) binds to cynomolgus LAG-3 with a $K_D$ of $1.5 \times 10^{-7}$ or less as measured by surface plasmon resonance;
h) binds to mouse LAG-3 with a $K_D$ of $3.5 \times 10^{-8}$ or less as measured by surface plasmon resonance;
i) stimulates IL-2 production in Staphylococcal enterotoxin B (SEB) treated human peripheral blood mononuclear cells (PBMCs);
j) reduces cellular levels of LAG-3 in human T cells;
k) reduces soluble levels of LAG-3 in the culture of human T cells;
l) induces tumor growth regression in vivo;
m) delays tumor growth in vivo; and
n) does not bind to the same epitope of human LAG-3 as antibody 25F7-Lag3.5.

Examples of such an antibody include, without limitation, antibody 15646 (having at least properties b, c, d, e, i, and n), antibody 15532 (having at least properties a, c, d, e, f, g, i, j, k, m, and n), antibody 15723 (having at least properties b, c, d, e, i, and n), antibody 15595 (having at least properties a, c, d, e, i, and n), antibody 15431 (having at least properties a, c, d, e, f, g, i, and n), antibody 15572 (having at least properties b, c, d, e, f, g, i, and n), and antibody 15011 (having at least properties a, c, d, e, f, g, h, i, j, k, l, m, and n). In some embodiments, the anti-TIM-3 antibody or antigen-binding portion of the invention has at least 13, 12, 11, 10, 9, 8, 7, 6, 5, 4, 3, 2, or 1 of said properties. In some embodiments, the anti-TIM-3 antibody or antigen-binding portion of the invention has at least properties b, c, d, e, i, and n; at least properties a, c, d, e, f, g, i, j, k, m, and n; at least properties a, c, d, e, i, and n; at least properties a, c, d, e, f, g, i, and n; at least properties b, c, d, e, f, g, i, and n; or at least properties a, c, d, e, f, g, h, i, j, k, l, m, and n.

In some embodiments, the anti-LAG-3 antibody or antigen-binding portion of the invention competes for binding to human LAG-3 with antibody 15011, 15572, and/or 15431.

In some embodiments, the anti-LAG-3 antibody or antigen-binding portion of the invention binds to an epitope of human LAG-3 having:
a) amino acid residues H85, P86, A87, P89, S91, W92, and G93 of SEQ ID NO: 68;
b) amino acid residues A40, Q41, P43, P46, P49, D52, T62, Q64, H65, Q66, P67, D68, G93, P94, P96, R98, Y99, T100, V101, P106, G107, R119, E124, R129, G130, D131, S133, R137, P138, D143, R148, and R163 of SEQ ID NO: 68;
c) amino acid residues A40, Q41, P43, P46, P49, D52, T62, Q64, H65, Q66, P67, D68, P96, Y99, T100, V101, P106, G107, R119, E124, R129, G130, D131, S133, R137, P138, D143, R148, and R163 of SEQ ID NO: 68; or
d) amino acid residues G107, L109, R110, and S111 of SEQ ID NO: 68.

In some embodiments, the anti-LAG-3 antibody or antigen-binding portion of the invention binds to an epitope having amino acid residues 98-105 of SEQ ID NO: 68. Examples of such an antibody include, without limitation, antibodies 15532, 15431, 15572, and 15011.

In some embodiments, the anti-LAG-3 antibody or antigen-binding portion of the invention binds to an epitope having:
a) amino acid residues 78-105 and 123-131 of SEQ ID NO: 68;
b) amino acid residues 23-30, 40-66, 88-105, 123-137, and 148-152 of SEQ ID NO: 68; or
c) amino acid residues 23-30, 40-66, 98-105, 118-137, and 148-161 of SEQ ID NO: 68

In some embodiments, the antibody of the present invention is of isotype IgG, for example, of isotype IgG subclass $IgG_1$ or $IgG_2$. In certain embodiments, the antibody comprises at least one mutation in the $F_c$ region. In particular embodiments, the antibody comprises a mutation in one or more of heavy chain amino acid positions 228, 234 and 235, which are numbered according to the IMGT® numbering scheme. For example, one or both of the amino acid residues at positions 234 and 235 may be mutated from Leu to Ala, and/or the amino acid residue at position 228 may be mutated from Ser to Pro.

In another aspect, the present invention provides pharmaceutical compositions comprising at least one (e.g., one) anti-LAG-3 antibody or antigen-binding portion thereof as described herein and a pharmaceutically acceptable excipient, optionally with an additional therapeutic, such as an anti-cancer antibody therapeutic.

The present invention further provides isolated nucleic acid molecules comprising a nucleotide sequence that encodes the heavy chain or an antigen-binding portion thereof, a nucleotide sequence that encodes the light chain or an antigen-binding portion thereof, or both, of an anti- LAG-3 antibody as described herein. The invention also provides vectors comprising such an isolated nucleic acid molecule, wherein said vector may further comprise an expression control sequence.

The present invention also provide host cells comprising a nucleotide sequence that encodes the heavy chain or an antigen-binding portion thereof, a nucleotide sequence that encodes the light chain or an antigen-binding portion thereof, or both, of an anti-LAG-3 antibody as described herein.

The present invention also provides a method for producing an antibody or antigen-binding portion thereof as described herein, comprising providing a host cell that comprises a nucleotide sequence that encodes the heavy chain or an antigen-binding portion thereof and a nucleotide sequence that encodes the light chain or an antigen-binding portion thereof of an anti-LAG-3 antibody as described herein, culturing said host cell under conditions suitable for expression of the antibody or portion, and isolating the resulting antibody or portion.

The present invention also provides a multi-specific (e.g., bi-specific) binding molecule comprising the antigen-binding portion of an anti-LAG-3 antibody described herein and the antigen-binding portion of another, distinct antibody such as another anti-LAG-3 antibody (e.g., as described herein) or an antibody that targets a different protein, such as another immune checkpoint protein, a cancer antigen, or another cell surface molecule whose activity mediates a disease condition such as cancer.

The present invention also provides a method for treating a patient with a LAG-3-related disorder, comprising administering to said patient an anti-LAG-3 antibody or an antigen-binding portion thereof, a pharmaceutical composition, or a bi-specific binding molecule as described herein. Unless otherwise indicated, a patient refers herein to a human patient.

The present invention also provides a method for enhancing immunity in a patient, comprising administering to said patient an anti-LAG-3 antibody or an antigen-binding portion thereof, a pharmaceutical composition, or a bi-specific binding molecule as described herein.

The present invention further provides a method for treating cancer in a patient, comprising administering to said patient an anti-LAG-3 antibody or an antigen-binding portion thereof, a pharmaceutical composition, or a bi-specific binding molecule as described herein. In some embodiments, the cancer originates in a tissue selected from skin, lung, intestine, colon, ovary, brain, prostate, kidney, soft tissues, hematopoietic system, head and neck, liver, bladder, breast, stomach, uterus and pancreas. In certain embodiments, the cancer is fibrosarcoma, non-small cell lung cancer, melanoma, glioblastoma, gliosarcoma, or colorectal cancer.

Any of the above methods may further comprise administration of, e.g., a chemotherapeutic agent, an anti-neoplastic agent, an anti-angiogenic agent, a tyrosine kinase inhibitor, a LAG-3 pathway inhibitor, or radiation therapy. In some embodiments, the method further comprises administration of retinoic acid, phenylbutyrate, all-trans-retinoic acid, and/or active form vitamin D.

The present invention further provides the use of an antibody composition comprising an anti-LAG-3 antibody or antigen-binding portion as described herein for the manufacture of a medicament for treating a patient with a LAG-3-related disorder, treating cancer in a patient, and/or enhancing immunity in a patient in need thereof.

The present invention further provides an anti-LAG-3 antibody or antigen-binding portion as described herein for treating a patient with a LAG-3-related disorder, treating cancer in a patient, and/or enhancing immunity in a patient in need thereof.

The present invention further provides an article of manufacture comprising an anti-LAG-3 antibody or antigen-binding portion as described herein, wherein said article of manufacture is suitable for treating a patient with a LAG-3-related disorder, treating cancer in a patient, and/or enhancing immunity in a patient in need thereof.

BRIEF DESCRIPTION OF THE DRAWINGS

FIG. 1A: an antibody clone binding specifically to human LAG-3-transfected cells. FIG. 1B: an antibody clone binding non-specifically to CHO-S cells. FIG. 1C: an antibody clone that does not bind to any of the cell populations used in the screening.

DETAILED DESCRIPTION OF THE INVENTION

Figure 1A:
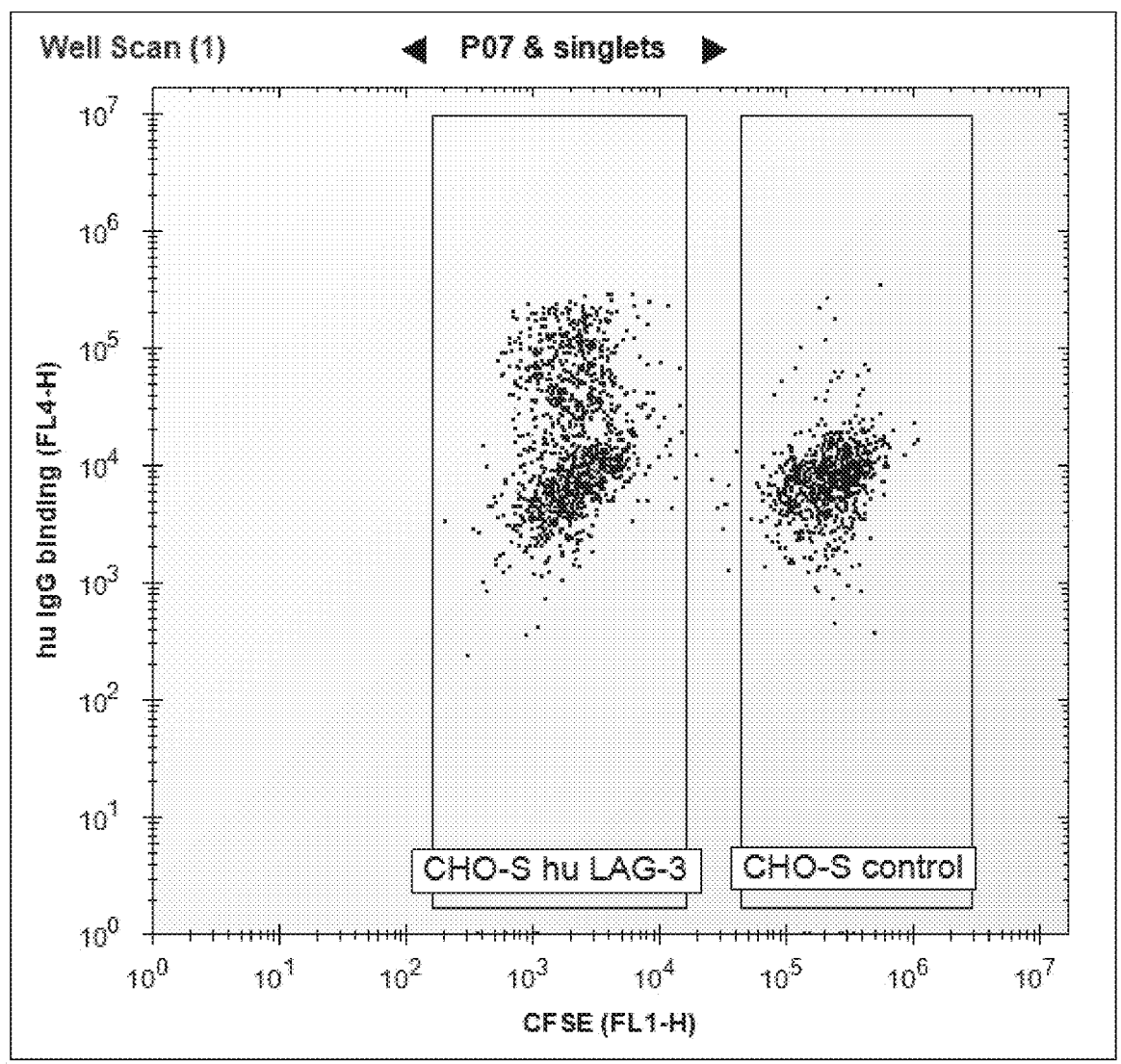
FIGS. 1A-1C show representative flow cytometry dot plots for antibodies generated as described in Example 2.

The present invention provides new anti-human LAG-3 antibodies that can be used to enhance the immune system in a human patient, such as a cancer patient. Unless otherwise stated, as used herein, "LAG-3" refers to human LAG-3. A human LAG-3 polypeptide sequence is available under UniProt Accession No. P18627 (LAG3_HUMAN) (SEQ ID NO: 68).

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers in the heavy or light chain may be in accordance with IMGT® definitions (Lefranc et al., *Dev Comp Immunol* 27(1):55-77 (2003)); or the definitions of Kabat, Sequences of Proteins of Immunological Interest (National Institutes of Health, Bethesda, Md. (1987 and 1991)); Chothia & Lesk, *J. Mol. Biol.* 196:901-917 (1987); or Chothia et al., *Nature* 342:878-883 (1989).

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, the term "germline" refers to the nucleotide and amino acid sequences of antibody genes and gene segments as they are passed from parents to offspring via germ cells. Germline sequences are distinguished from the nucleotide sequences encoding antibodies in mature B cells, which have been altered by recombination and hypermutation events during the course of B cell maturation. An antibody that "utilizes" a particular germline sequence has a nucleotide or amino acid sequence that aligns with that germline nucleotide sequence or with the amino acid sequence that it specifies more closely than with any other germline nucleotide or amino acid sequence.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is ≤1 mM, preferably ≤100 nM. A $K_D$ binding affinity constant can be measured, e.g., by surface plasmon resonance (BIAcore™) or Bio-Layer Interferometry, for example using the IBIS MX96 SPR system from IBIS Technologies or the Octet™ system from ForteBio.

The term "$k_{off}$" refers to the dissociation rate constant of a particular antibody-antigen interaction. A $k_{off}$ dissociation rate constant can be measured, e.g., by SPR (surface plasmon resonance), for example using the using the IBIS MX96 system.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., LAG-3) or a relevant portion thereof, then screening for binding to the epitope.

One can determine whether an antibody binds to the same epitope as or competes for binding with an anti-LAG-3 antibody of the invention by using methods known in the art, including, without limitation, competition assays, epitope binning, and alanine scanning. In one embodiment, one allows the anti-LAG-3 antibody of the invention to bind to LAG-3 under saturating conditions, and then measures the ability of the test antibody to bind to LAG-3. If the test antibody is able to bind to LAG-3 at the same time as the reference anti-LAG-3 antibody, then the test antibody binds to a different epitope than the reference anti-LAG-3 antibody. However, if the test antibody is not able to bind to LAG-3 at the same time, then the test antibody binds to the same epitope, an overlapping epitope, or an epitope that is in close proximity to the epitope bound by the anti-LAG-3 antibody of the invention. This experiment can be performed using, e.g., ELISA, RIA, BIACORE™, SPR, Bio-Layer Interferometry or flow cytometry. To test whether an anti-LAG-3 antibody cross-competes with another anti-LAG-3 antibody, one may use the competition method described above in two directions, i.e., determining if the known antibody blocks the test antibody and vice versa. Such cross-competition experiments may be performed, e.g., using an IBIS MX96 SPR instrument or the Octet™ system.

An antibody that binds to the same epitope as or competes for binding with an antibody of the invention preferably has MHCII blocking activity, e.g. as determined using the flow cytometric competition assay described in Example 6. An antibody that binds to the same epitope as or competes for binding with an antibody of the invention may reduce binding by at least, e.g., 35%, 40%, 45%, 50%, 55%, 60%, 65%, 70%, 75%, or 80%, or preferably by at least 85%, 86%, 87%, 88%, 89%, 90%, 91%, 92%, 93%, 94%, 95%, 96%, 97%, 98%, 99%, or 100%.

The term "chimeric antibody" refers in its broadest sense to an antibody that contains one or more regions from one antibody and one or more regions from one or more other antibodies, typically an antibody that is partially of human origin and partially of non-human origin, i.e., derived in part from a non-human animal, for example a mouse, rat or other rodent, or an avian such as a chicken. Chimeric antibodies are preferred over non-human antibodies in order to reduce the risk of a human anti-antibody response, e.g., a human anti-mouse antibody response in the case of a murine antibody. An example of a typical chimeric antibody is one in which the variable domain sequences are murine while the constant region sequences are human. In the case of a chimeric antibody, the non-human parts may be subjected to further alteration in order to humanize the antibody. The chimeric antibodies described herein may have, e.g., chicken variable domain sequences and human constant region sequences.

The term "humanize" refers to the fact that where an antibody is wholly or partially of non-human origin (for example, a murine or chicken antibody obtained from immunization of mice or chickens, respectively, with an antigen of interest, or a chimeric antibody based on such a murine or chicken antibody), it is possible to replace certain amino acids, in particular in the framework regions and constant regions of the heavy and light chains, in order to avoid or minimize an immune response in humans. Although it is not possible to precisely predict the immunogenicity, and thereby the human anti-antibody response, of a particular antibody, non-human antibodies tend to be more immunogenic in humans than human antibodies. Chimeric antibodies, where the foreign (e.g. rodent or avian) constant regions have been replaced with sequences of human origin, have been shown to be generally less immunogenic than antibodies of fully foreign origin, and the trend in therapeutic antibodies is towards humanized or fully human antibodies. Chimeric antibodies or other antibodies of non-human origin thus can be humanized to reduce the risk of a human anti-antibody response.

For chimeric antibodies, humanization typically involves modification of the framework regions of the variable domain sequences. Amino acid residues that are part of complementarity determining regions (CDRs) most often will not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art, see, e.g., the review by Almagro & Fransson, *Front Biosci.* 13:1619-1633 (2008). One commonly used method is CDR grafting, which for, e.g., a murine-derived chimeric antibody involves identification of human germline gene counterparts to the murine variable domain genes and grafting of the murine CDR sequences into this framework. The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, e.g., by constructing expression vectors that express CDR sequences from the specific antibody grafted into framework sequences from a different antibody. As a result, it is possible to "humanize" a non-human antibody and still substantially maintain the binding specificity and affinity of the original antibody. CDR grafting may be based on the Kabat CDR definitions, although a more recent publication (Magdelaine-Beuzelin et al., *Crit Rev. Oncol Hematol.* 64:210-225 (2007)) has suggested that the IMGT® definition (the international ImMunoGeneTics information System®) may improve the result of the humanization (see Lefranc et al., *Dev. Comp Immunol.* 27:55-77 (2003)).

In some cases, CDR grafting may reduce the binding specificity and affinity, and thus the biological activity, of a CDR-grafted antibody as compared to the parent antibody from which the CDRs are obtained. Back mutations (sometimes referred to as "framework repair") may be introduced at selected positions of the CDR-grafted antibody, typically in the framework regions, in order to reestablish the binding specificity and affinity of the parent antibody. Positions for possible back mutations can be identified using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

In certain cases, it also may be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., *Proc Natl Acad Sci USA*, 94:412-417 (1997), and the stepwise in vitro affinity maturation method of Wu et al., *Proc Natl Acad Sci USA* 95:6037-6042 (1998).

The term "antigen-binding portion" of an antibody (or simply "antibody portion"), as used herein, refers to one or more portions or fragments of an antibody that retain the ability to specifically bind to an antigen (e.g., human LAG-3, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, $C_L$ and $C_H1$ domains; (ii) a F(ab')$_2$ fragment: a bivalent fragment comprising two Fab fragments linked by a disulfide bridge at the hinge region; (iii) an Fd fragment consisting of the $V_H$ and $C_H1$ domains; (iv) a Fv fragment consisting of the $V_L$ and $V_H$ domains of a single arm of an antibody, (v) a dAb fragment, which consists of a $V_H$ domain; and (vi) an isolated complementarity determining region (CDR) capable of specifically binding to an antigen. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ domains pair to form monovalent molecules (known as single chain Fv (scFv)). Also within the invention are antigen-binding molecules comprising a $V_H$ and/or a $V_L$. In the case of a $V_H$, the molecule may also comprise one or more of a $C_H1$, hinge, $C_H2$, or $C_H3$ region. Such single chain antibodies are also intended to be encompassed within the term "antigen-binding portion" of an antibody. Other forms of single chain antibodies, such as diabodies, are also encompassed. Diabodies are bivalent, bi-specific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

The class (isotype) and subclass of anti-LAG-3 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

Unless otherwise indicated, all antibody amino acid residue numbers referred to in this disclosure are those under the IMGT® numbering scheme.

Anti-LAG-3 Antibodies

The present invention provides antibodies directed against LAG-3, and antigen-binding portions thereof. In a particular embodiment, the antibodies disclosed herein are human antibodies generated from transgenic rats that are able to generate antibodies with human idiotypes. In another embodiment, the antibodies are chicken-derived chimeric antibodies comprising chicken CDR sequences and human framework regions, where the framework regions have been subjected to humanization.

One advantage of the novel anti-LAG-3 antibodies of the invention is that they are able to enhance activity of T-cells as measured by increased IL-2 production; see, e.g., Example 7. While not wishing to be bound by any particular theory, it is believed that the anti-LAG-3 antibodies of the invention are able to block the interaction of LAG-3 with its putative ligands such as MHCII and LSECtin. The antibodies may accomplish this directly via blocking of the ligand binding region, as demonstrated, e.g., in Example 6, or via induction of LAG-3 internalization, which is contemplated as a possible mechanism of action behind the results presented in Example 9. Another potential advantage of the anti-LAG-3 antibodies of the invention is a low level of secondary effector functions in antibodies having the "LALA" mutations (L234A/L235A), which hinder significant antibody binding to human FcgR (Fc gamma receptors) and hence depletion of effector T-cells.

In one embodiment, the anti-LAG-3 antibody has a heavy chain CDR3 (H-CDR3) that is at least 90% identical in sequence to any one of SEQ ID NOs: 37, 43, 46, 50, 55, 58, and 64, e.g. at least 92% identical, such as at least 95%, 96%, at least 97%, at least 98% or at least 99% identical to any one of SEQ ID NOs: 37, 43, 46, 50, 55, 58, and 64.

In one embodiment, the anti-LAG-3 antibody has a heavy chain variable domain (VH) that is at least 90% identical in sequence to any one of SEQ ID NOs: 3, 7, 11, 15, 19, 23 or 27, e.g. at least 92% identical, such as at least 95%, 96%, at least 97%, at least 98% or at least 99% identical to any one of SEQ ID NOs: 3, 7, 11, 15, 19, 23 or 27.

In another embodiment, the anti-LAG-3 antibody has a heavy chain variable domain (VH) that is at least 90% identical in sequence to any one of SEQ ID NOs: 3, 7, 11, 15, 19, 23 or 27, e.g. at least 92% identical, such as at least 95%, at least 96%, at least 97%, at least 98% or at least 99% identical to any one of SEQ ID NOs: 3, 7, 11, 15, 19, 23 or 27; and a heavy chain constant region that is at least 90% identical in sequence to SEQ ID NO: 30, e.g. at least 92% identical, such as at least 95%, at least 96%, at least 97%, at least 98% or at least 99% identical to SEQ ID NO: 30.

In another embodiment, the anti-LAG-3 antibody has a heavy chain (HC) that comprises the VH amino acid sequence of any one of SEQ ID NOs: 3, 7, 11, 15, 19, 23 or 27 and the heavy chain constant region amino acid sequence of SEQ ID NO: 30.

In one embodiment, the anti-LAG-3 antibody has a light chain CDR3 (L-CDR3) that is at least 90% identical in sequence to any one of SEQ ID NOs: 40, 52, 61, and 67, e.g. at least 92% identical, such as at least 95%, 96%, at least 97%, at least 98% or at least 99% identical to any one of SEQ ID NOs: 40, 52, 61, and 67.

In another embodiment, the anti-LAG-3 antibody has a light chain variable domain (VL) that is at least 90% identical in sequence to the VL amino acid sequence of any one of SEQ ID NOs: 4, 8, 12, 16, 20, 24 or 28, e.g. at least 92% identical, such as at least 95%, at least 96%, at least 97%, at least 98% or at least 99% identical to any one of SEQ ID NOs: 4, 8, 12, 16, 20, 24 or 28.

In another embodiment, the anti-LAG-3 antibody has a light chain variable domain (VL) that is at least 90% identical in sequence to the VL amino acid sequence of any one of SEQ ID NOs: 4, 8, 12, 16, 20 or 24, e.g. at least 92% identical, such as at least 95%, at least 96%, at least 97%, at least 98% or at least 99% identical to any one of SEQ ID NOs: 4, 8, 12, 16, 20 or 24; and a light chain constant region amino acid sequence that is at least 90% identical in sequence to SEQ ID NO: 34, e.g. at least 92% identical, such as at least 95%, at least 96%, at least 97%, at least 98% or at least 99% identical to SEQ ID NO: 34.

In another embodiment, the anti-LAG-3 antibody has a light chain variable domain (VL) that is at least 90% identical in sequence to the VL amino acid sequence of SEQ ID NO: 28, e.g. at least 92% identical, such as at least 95%, at least 96%, at least 97%, at least 98% or at least 99% identical to SEQ ID NO: 28; and a light chain constant region amino acid sequence that is at least 90% identical in sequence to SEQ ID NO: 32, e.g. at least 92% identical, such as at least 95%, at least 96%, at least 97%, at least 98% or at least 99% identical to SEQ ID NO: 32.

In another embodiment, the anti-LAG-3 antibody has a light chain that comprises any one of SEQ ID NOs: 4, 8, 12, 16, 20 or 24, and SEQ ID NO: 34.

In another embodiment, the anti-LAG-3 antibody has a light chain that comprises SEQ ID NO: 28 and SEQ ID NO: 32.

In certain embodiments, the anti-LAG-3 antibody comprises any one of the above-described heavy chains and any one of the above-described light chains.

In some embodiments, the anti-LAG-3 antibody or antigen-binding portion of the invention comprises the H-CDR1-3 and L-CDR1-3 amino acid sequences of:
a) SEQ ID NOs: 35, 36, 37, 38, 39, and 40, respectively;
b) SEQ ID NOs: 41, 42, 43, 44, 45, and 40, respectively;
c) SEQ ID NOs: 35, 42, 46, 44, 47, and 40, respectively;
d) SEQ ID NOs: 48, 49, 50, 51, 47, and 52, respectively;
e) SEQ ID NOs: 53, 54, 55, 44, 45, and 40, respectively;
f) SEQ ID NOs: 56, 57, 58, 59, 60, and 61, respectively; or
g) SEQ ID NOs: 62, 63, 64, 65, 66, and 67, respectively.

In some embodiments, the anti-LAG-3 antibody or antigen-binding portion of the invention comprises an H-CDR3 and an L-CDR3 that are 80%, 85%, 90%, 91%, 92%, 93%, 94%, 95%, 96%, 97%, 98%, or 99% identical to the amino acid sequences of:
a) SEQ ID NOs: 37 and 40, respectively;
b) SEQ ID NOs: 43 and 40, respectively;
c) SEQ ID NOs: 46 and 40, respectively;
d) SEQ ID NOs: 50 and 52, respectively;
e) SEQ ID NOs: 55 and 40, respectively;
f) SEQ ID NOs: 58 and 61, respectively; or
g) SEQ ID NOs: 64 and 67, respectively.

In some embodiments, the anti-LAG-3 antibody or antigen-binding portion of the invention comprises a VH and a VL that are 80%, 85%, 90%, 91%, 92%, 93%, 94%, 95%, 96%, 97%, 98%, or 99% identical to the amino acid sequences of:
a) SEQ ID NOs: 3 and 4, respectively;
b) SEQ ID NOs: 7 and 8, respectively;
c) SEQ ID NOs: 11 and 12, respectively;
d) SEQ ID NOs: 15 and 16, respectively;
e) SEQ ID NOs: 19 and 20, respectively;
f) SEQ ID NOs: 23 and 24, respectively; or
g) SEQ ID NOs: 27 and 28, respectively.

In some embodiments, the anti-LAG-3 antibody or antigen-binding portion of the invention comprises a VH and a VL that have the amino acid sequences of:
a) SEQ ID NOs: 3 and 4, respectively;
b) SEQ ID NOs: 7 and 8, respectively;
c) SEQ ID NOs: 11 and 12, respectively;
d) SEQ ID NOs: 15 and 16, respectively;
e) SEQ ID NOs: 19 and 20, respectively;
f) SEQ ID NOs: 23 and 24, respectively; or
g) SEQ ID NOs: 27 and 28, respectively.

In some embodiments, the anti-LAG-3 antibody comprises:
a) an HC with the amino acid sequences of SEQ ID NOs: 3 and 30 and an LC with the amino acid sequences of SEQ ID NOs: 4 and 34;
b) an HC with the amino acid sequences of SEQ ID NOs: 7 and 30 and an LC with the amino acid sequences of SEQ ID NOs: 8 and 34;
c) an HC with the amino acid sequences of SEQ ID NOs: 11 and 30 and an LC with the amino acid sequences of SEQ ID NOs: 12 and 34;
d) an HC with the amino acid sequences of SEQ ID NOs: 15 and 30 and an LC with the amino acid sequences of SEQ ID NOs: 16 and 34;
e) an HC with the amino acid sequences of SEQ ID NOs: 19 and 30 and an LC with the amino acid sequences of SEQ ID NOs: 20 and 34;
f) an HC with the amino acid sequences of SEQ ID NOs: 23 and 30 and an LC with the amino acid sequences of SEQ ID NOs: 24 and 34; or
g) an HC with the amino acid sequences of SEQ ID NOs: 27 and 30 and an LC with the amino acid sequences of SEQ ID NOs: 28 and 32.

In some embodiments, the anti-LAG-3 antibody or antigen-binding portion of the invention comprises the H-CDR1-3 and L-CDR1-3 amino acid sequences of antibody 15646, 15532, 15723, 15595, 15431, 15572 or 15011.

In some embodiments, the anti-LAG-3 antibody or antigen-binding portion of the invention comprises a VH and VL that are at least 90% identical in amino acid sequence to the VH and VL, respectively, of antibody 15646, 15532, 15723, 15595, 15431, 15572 or 15011.

In some embodiments, the anti-LAG-3 antibody or antigen-binding portion of the invention comprises a VH and VL that are the VH and VL, respectively, of antibody 15646, 15532, 15723, 15595, 15431, 15572 or 15011.

In some embodiments, the anti-LAG-3 antibody of the invention is antibody 15646, 15532, 15723, 15595, 15431, 15572 or 15011, or an antibody with the same amino acid sequences as said antibody.

The invention also provides an anti-LAG-3 antibody or an antigen-binding portion thereof that binds to an epitope of human LAG-3 having:
a) 1, 2, 3, 4, 5, 6, or all 7 amino acid residues selected from H85, P86, A87, P89, S91, W92, and G93 of SEQ ID NO: 68 (e.g., antibody 15532);
b) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or all 32 amino acid residues selected from A40, Q41, P43, P46, P49, D52, T62, Q64, H65, Q66, P67, D68, G93, P94, P96, R98, Y99, T100, V101, P106, G107, R119, E124, R129, G130, D131, S133, R137, P138, D143, R148, and R163 of SEQ ID NO: 68 (e.g., antibody 15431);
c) 1, 2, 3, 4, 5, 6, 7, 8, 9, 10, 11, 12, 13, 14, 15, 16, 17, 18, 19, 20, 21, 22, 23, 24, 25, 26, 27, 28, or all 29 amino acid residues selected from A40, Q41, P43, P46, P49, D52, T62, Q64, H65, Q66, P67, D68, P96, Y99, T100, V101, P106, G107, R119, E124, R129, G130, D131, S133, R137, P138, D143, R148, and R163 of SEQ ID NO: 68 (e.g., antibody 15572); or
d) 1, 2, 3, or all 4 amino acid residues selected from G107, L109, R110, and S111 of SEQ ID NO: 68 (e.g., antibody 15011).

The invention also provides a monoclonal antibody or an antigen-binding portion thereof that binds to an epitope of human LAG-3 having residues 98-105. In some embodiments, the antibody or antigen-binding portion binds to an epitope of human LAG-3 having:
a) two, or three amino acid segments selected from residues 78-105 and 123-131 of SEQ ID NO: 68 (e.g., antibody 15532);

b) one, two, three, four, or five amino acid segments selected from residues 23-30, 40-66, 88-105, 123-137, and 148-152 of SEQ ID NO: 68 (e.g., antibody 15431);

c) one, two, three, four, or five amino acid segments selected from residues 23-30, 40-66, 98-105, 118-137, and 148-161 of SEQ ID NO: 68 (e.g., antibody 15572); or d) amino acid residues 98-105 of SEQ ID NO: 68 (e.g., antibody 15011).

The invention also provides a monoclonal antibody or an antigen-binding portion thereof that binds to an epitope of human LAG-3 having residues 23-30 and 40-66 of SEQ ID NO: 68. In some embodiments, the epitope further has residues 88-105, 123-137, and/or 148-152 of SEQ ID NO: 68. In some embodiments, the epitope further has residues 98-105, 118-137, and 148-161 of SEQ ID NO: 68.

The invention also provides an anti-LAG-3 antibody or an antigen-binding portion thereof that competes or cross-competes for binding with, or binds to the same epitope as, an antibody selected from the group consisting of 15532, 15646, 15723, 15595, 15431, 15572, and 15011.

In some embodiments, the anti-LAG-3 antibody or antigen-binding portion thereof of the invention does not bind to the same epitope of human LAG-3 as antibody 25F7-Lag3.5.

In some embodiments, the anti-LAG-3 antibody or antigen-binding portion thereof of the invention utilizes a human heavy chain germline gene selected from the group consisting of IGHV4-34, IGHV1-24, IGHV6-1, IGHV4-39, and IGHV3-23. In certain embodiments, the heavy chain germline gene is at least 75%, 80%, 82%, 85%, 86%, 87%, 88%, 89%, 90%, 91%, 92%, 93%, 94%, 95%, 96%, 97%, 98%, 99%, or 100% identical to the corresponding heavy chain sequence in the anti-LAG3 antibody or antigen-binding portion. In certain embodiments, the framework region sequences of said heavy chain germline gene are at least 75%, 80%, 82%, 85%, 86%, 87%, 88%, 89%, 90%, 91%, 92%, 93%, 94%, 95%, 96%, 97%, 98%, 99%, or 100% identical to the corresponding heavy chain framework region sequences in the anti-LAG3 antibody or antigen-binding portion.

In some embodiments, the anti-LAG-3 antibody or antigen-binding portion thereof of the invention utilizes a human light chain germline gene selected from the group consisting of IGKV3-11, IGKV1-12, IGKV1-5, and IGLV3-19. In certain embodiments, the light chain germline gene is at least 75%, 80%, 82%, 85%, 86%, 87%, 88%, 89%, 90%, 91%, 92%, 93%, 94%, 95%, 96%, 97%, 98%, 99%, or 100% identical to the corresponding light chain sequence in the anti-LAG3 antibody or antigen-binding portion. In certain embodiments, the framework region sequences of said light chain germline gene are at least 75%, 80%, 82%, 85%, 86%, 87%, 88%, 89%, 90%, 91%, 92%, 93%, 94%, 95%, 96%, 97%, 98%, 99%, or 100% identical to the corresponding light chain framework region sequences in the anti-LAG3 antibody or antigen-binding portion.

In particular embodiments, the anti-LAG-3 antibody or antigen-binding portion thereof of the invention utilizes any combination of the above human heavy chain germline genes and human light chain germline genes (e.g., IGHV4-34 and IGKV3-11, IGHV1-24 and IGKV1-12, IGHV6-1 and IGKV3-11, IGHV4-39 and IGKV1-5, or IGHV3-23 and IGLV3-19). In some embodiments, the heavy and light chain germline genes are at least 75%, 80%, 82%, 85%, 86%, 87%, 88%, 89%, 90%, 91%, 92%, 93%, 94%, 95%, 96%, 97%, 98%, 99%, or 100% identical to the corresponding heavy and light chain sequences, respectively, in the anti-LAG3 antibody or antigen-binding portion. In certain embodiments, the framework region sequences of said heavy and light chain germline genes are at least 75%, 80%, 82%, 85%, 86%, 87%, 88%, 89%, 90%, 91%, 92%, 93%, 94%, 95%, 96%, 97%, 98%, 99%, or 100% identical to the corresponding heavy and light chain framework region sequences, respectively, in the anti-LAG3 antibody or antigen-binding portion.

In some embodiments, any of the anti-LAG-3 antibodies or antigen-binding portions described herein may bind to human LAG-3 with an EC50 of, for example, 0.2 nM or less, 0.15 nM or less, 0.1 nM or less, 0.09 nM or less, 0.08 nM or less, 0.07 nM or less, 0.06 nM or less, 0.05 nM or less, or 0.04 nM or less. In some embodiments, any of the anti-LAG-3 antibodies or antigen-binding portions described herein may bind to cynomolgus LAG-3 with, for example, an EC50 of 0.4 nM or less, 0.3 nM or less, 0.2 nM or less, 0.1 nM or less, 0.09 nM or less, 0.08 nM or less, 0.07 nM or less, 0.06 nM or less, 0.05 nM or less, 0.04 nM or less, or 0.03 nM or less.

In some embodiments, any of the anti-LAG-3 antibodies or antigen-binding portions described herein may bind to human LAG-3 with an EC50 of, for example, 0.1 nM or less. In some embodiments, any of the anti-LAG-3 antibodies or antigen-binding portions described herein may bind to cynomolgus LAG-3 with, for example, an EC50 of 0.3 nM or less. In particular embodiments, any of the anti-LAG-3 antibodies or antigen-binding portions described herein may bind to human LAG-3 with, for example, an EC50 of 0.1 nM or less and cynomolgus LAG-3 with, for example, an EC50 of 0.3 nM or less.

In some embodiments, any of the anti-LAG-3 antibodies or antigen-binding portions described herein may inhibit binding of ligands such as MHC class II (MHCII) or LSECtin to LAG-3. For example, at 20 µg/mL, the anti-LAG-3 antibody or antigen-binding portion may reduce the binding of LAG-3 to MHCII by at least 35%, at least 40%, at least 45%, at least 50%, at least 55%, at least 60%, at least 65%, at least 70%, at least 75%, at least 80%, at least 85%, at least 89%, at least 90%, at least 91%, at least 92%, at least 93%, at least 94%, at least 95%, at least 96%, at least 97%, at least 98%, at least 99%, or 100% compared to binding in the presence of a negative control antibody. In one embodiment, the anti-LAG-3 antibody or antigen-binding protein may reduce the binding of LAG-3 to MHCII by great than 85% compared to the negative control. In one embodiment, the anti-LAG-3 antibody or antigen-binding protein may reduce the binding of LAG-3 to MHCII by between about 35% and 85% compared to the negative control.

In some embodiments, any of the anti-LAG-3 antibodies or antigen-binding portions described herein may block binding between LAG-3 and MHC class II, e.g., human LAG-3 expressed on Jurkat cells and human MHC class II expressed on Raji cells (for example, at a concentration of 0.1 µg/mL, 0.5 µg/mL, 1 µg/mL, 5 µg/mL, 10 µg/mL, 20 µg/mL, 30 µg/mL, 40 µg/mL, or 50 µg/mL).

In some embodiments, any of the anti-LAG-3 antibodies or antigen-binding portions described herein may bind to human LAG-3 with a $K_D$ of $5.0 \times 10^{-8}$ or less, $4.0 \times 10^{-8}$ or less, $3.0 \times 10^{-8}$ or less, $2.0 \times 10^{-8}$ or less, $1.0 \times 10^{-8}$ or less, $9.0 \times 10^{-9}$ or less, $8.0 \times 10^{-9}$ or less, $7.0 \times 10^{-9}$ or less, $6.0 \times 10^{-9}$ or less, $5.0 \times 10^{-9}$ or less, $4.0 \times 10^{-9}$ or less, $3.0 \times 10^{-9}$ or less, $2.0 \times 10^{-9}$ or less, or $1.0 \times 10^{-9}$ or less, as measured by surface plasmon resonance.

In some embodiments, any of the anti-LAG-3 antibodies or antigen-binding portions described herein may bind to cynomolgus LAG-3 with a $K_D$ of $1.5 \times 10^{-7}$ or less, $1.0 \times 10^{-7}$ or less, $9.0\times10^{-8}$ or less, $8.0\times10^{-8}$ or less, $7.0\times10^{-8}$ or less, $6.0\times10^{-8}$ or less, $5.0\times10^{-8}$ or less, $4.0\times10^{-8}$ or less, $3.0\times10^{-8}$ or less, $2.0\times10^{-8}$ or less, or $1.0\times10^{-8}$ or less, as measured by surface plasmon resonance.

In some embodiments, any of the anti-LAG-3 antibodies or antigen-binding portions described herein may bind to mouse LAG-3 with a $K_D$ of $5.0\times10^{-8}$ or less, $4.5\times10^{-8}$ or less, $4.0\times10^{-8}$ or less, $3.5\times10^{-8}$ or less, or $3.0\times10^{-8}$ or less, as measured by surface plasmon resonance.

In some embodiments, any of the anti-LAG-3 antibodies or antigen-binding portions described herein may stimulate IL-2 production, e.g., from SEB-stimulated PBMCs.

In some embodiments, any of the anti-LAG-3 antibodies or antigen-binding portions described herein may reduce cellular and/or soluble levels of LAG-3, e.g., in a human T cell line (such as a human T cell line overexpressing LAG-3).

In some embodiments, any of the anti-LAG-3 antibodies or antigen-binding portions described herein may induce tumor growth regression and/or delay tumor growth in vivo.

In some embodiments, any of the anti-LAG-3 antibodies or antigen-binding portions described herein may bind to a different epitope of human LAG-3 than antibody 25F7-Lag3.5.

In one embodiment, administration of an anti-LAG-3 antibody of the invention or an antigen-binding portion thereof may activate T-cells, causing enhanced anti-tumor activity.

The class of an anti-LAG-3 antibody obtained by the methods described herein may be changed or switched with another class or subclass. In one aspect of the invention, a nucleic acid molecule encoding VL or VH is isolated using methods well-known in the art such that it does not include nucleic acid sequences encoding CL or CH, respectively. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH chain, as described above. For example, an anti-LAG-3 antibody that was originally IgM may be class switched to IgG. Further, the class switching may be used to convert one IgG subclass to another, e.g., from $IgG_1$ to $IgG_2$. A κ light chain constant region can be changed, e.g., to a λ light chain constant region. A preferred method for producing an antibody of the invention with a desired Ig isotype comprises the steps of isolating a nucleic acid molecule encoding the heavy chain of an anti-LAG-3 antibody and a nucleic acid molecule encoding the light chain of an anti-LAG-3 antibody, obtaining the variable domain of the heavy chain, ligating the variable domain of the heavy chain with the constant region of a heavy chain of the desired isotype, expressing the light chain and the ligated heavy chain in a cell, and collecting the anti-LAG-3 antibody with the desired isotype.

The anti-LAG-3 antibody of the invention can be an IgG, an IgM, an IgE, an IgA, or an IgD molecule, but is typically of the IgG isotype, e.g. of IgG subclass $IgG_1$, $IgG_2$a or $IgG_2$b, $IgG_3$ or $IgG_4$. In one embodiment, the antibody is an $IgG_1$. In another embodiment, the antibody is an $IgG_2$. In certain embodiments, the $IgG_1$ antibodies of the present invention that bind to a LAG-3 epitope described herein offer superior activity in modulating (e.g., inhibiting) LAG-3 functions to achieve the cancer treatment or immunostimulatory effects.

In one embodiment, the anti-LAG-3 antibody may comprise at least one mutation in the Fc region. A number of different Fc mutations are known, where these mutations provide altered effector function. For example, in many cases it will be desirable to reduce or eliminate effector function, e.g. where ligand/receptor interactions are undesired or in the case of antibody-drug conjugates.

In one embodiment, the anti-LAG-3 antibody comprises at least one mutation in the Fc region that reduces effector function. Fc region amino acid positions that may be advantageous to mutate in order to reduce effector function include one or more of positions 228, 233, 234 and 235, where amino acid positions are numbered according to the IMGT® numbering scheme.

In one embodiment, one or both of the amino acid residues at positions 234 and 235 may be mutated, for example from Leu to Ala (L234A/L235A). These mutations reduce effector function of the Fc region of $IgG_1$ antibodies. Additionally or alternatively, the amino acid residue at position 228 may be mutated, for example to Pro. In some embodiments, the amino acid residue at position 233 may be mutated, e.g., to Pro, the amino acid residue at position 234 may be mutated, e.g., to Val, and/or the amino acid residue at position 235 may be mutated, e.g., to Ala. The amino acid positions are numbered according to the IMGT® numbering scheme.

In some embodiments, where the antibody is of the $IgG_4$ subclass, it may comprise the mutation S228P, i.e. having a proline in position 228, where the amino acid position is numbered according to the IMGT® numbering scheme. This mutation is known to reduce undesired Fab arm exchange.

In certain embodiments, an antibody or antigen-binding portion thereof of the invention may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of an anti-LAG-3 antibody of the invention linked to another polypeptide. In certain embodiments, only the variable domains of the anti-LAG-3 antibody are linked to the polypeptide. In certain embodiments, the VH domain of an anti-LAG-3 antibody is linked to a first polypeptide, while the VL domain of an anti-LAG-3 antibody is linked to a second polypeptide that associates with the first polypeptide in a manner such that the VH and VL domains can interact with one another to form an antigen-binding site. In another preferred embodiment, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bi-specific antibody.

To create a single chain antibody (scFv), the VH- and VL-encoding DNA fragments are operatively linked to another fragment encoding a flexible linker, e.g., encoding the amino acid sequence (Gly4-Ser)3 (SEQ ID NO: 74), such that the VH and VL sequences can be expressed as a contiguous single-chain protein, with the VL and VH domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used. Bi-specific or polyvalent antibodies may be generated that bind specifically to human LAG-3 and to another molecule, for instance.

In other embodiments, other modified antibodies may be prepared using anti-LAG-3 antibody-encoding nucleic acid molecules. For instance, "kappa bodies" (Ill et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

An anti-LAG-3 antibody or antigen-binding portion of the invention can be derivatized or linked to another molecule (e.g., another peptide or protein). In general, the antibodies or portions thereof are derivatized such that LAG-3 binding is not affected adversely by the derivatization or labeling. Accordingly, the antibodies and antibody portions of the invention are intended to include both intact and modified forms of the human anti-LAG-3 antibodies described herein. For example, an antibody or antibody portion of the invention can be functionally linked (by chemical coupling, genetic fusion, noncovalent association or otherwise) to one or more other molecular entities, such as another antibody (e.g., a bi-specific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, e.g., to create bi-specific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, Ill.

An anti-LAG-3 antibody can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody according to the present invention may also be labeled. As used herein, the terms "label" or "labeled" refer to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the antibodies of the invention may be present in a neutral form (including zwitter ionic forms) or as a positively or negatively-charged species. In some embodiments, the antibodies may be complexed with a counterion to form a pharmaceutically acceptable salt.

The term "pharmaceutically acceptable salt" refers to a complex comprising one or more antibodies and one or more counterions, wherein the counterions are derived from pharmaceutically acceptable inorganic and organic acids and bases.

Bi-Specific Binding Molecules

In a further aspect, the invention provides a bi-specific binding molecule having the binding specificity (e.g., comprising the antigen-binding portions) of an anti-LAG-3 antibody described herein and the binding specificity of another anti-LAG-3 antibody (e.g., another anti-LAG-3 antibody described herein) or an antibody that targets a different protein, such as another immune checkpoint protein, a cancer antigen, or another cell surface molecule whose activity mediates a disease condition such as cancer. Such bi-specific binding molecules are known in the art, and examples of different types of bi-specific binding molecules are given elsewhere herein.

Nucleic Acid Molecules and Vectors

The present invention also provides nucleic acid molecules and sequences encoding anti-LAG-3 antibodies or antigen-binding portions thereof described herein. In some embodiments, different nucleic acid molecules encode the heavy chain and light chain amino acid sequences of the anti-LAG-3 antibody or an antigen-binding portion thereof. In other embodiments, the same nucleic acid molecule encodes the heavy chain and light chain amino acid sequences of the anti-LAG-3 antibody or an antigen-binding portion thereof.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single- and double-stranded forms.

The invention also provides nucleotide sequences that are at least 70%, 75%, 80%, 85%, 90%, 95%, 97%, 98% or 99% identical to one or more nucleotide sequences recited herein, e.g., to a nucleotide sequence selected from the group consisting of SEQ ID NOs: 1, 2, 5, 6, 9, 10, 13, 14, 17, 18, 21, 22, 25 and 26, or to a nucleotide sequence encoding an amino acid sequence selected from the group consisting of SEQ ID NOs: 3, 4, 7, 8, 11, 12, 15, 16, 19, 20, 23, 24, 27 and 28. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (see, e.g., Pearson, *Methods Enzymol.* 183:63-98 (1990); Pearson, *Methods Mol. Biol.* 132:185-219 (2000); Pearson, *Methods Enzymol.* 266:227-258 (1996); and Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In one aspect, the invention provides a nucleic acid molecule comprising a nucleotide sequence selected from the group consisting of SEQ ID NOs: 1, 2, 5, 6, 9, 10, 13, 14, 17, 18, 21, 22, 25 and 26. In certain embodiments, the nucleic acid molecule comprises the nucleotide sequences of SEQ ID NOs: 1 and 2, SEQ ID NOs: 5 and 6, SEQ ID NOs: 9 and 10, SEQ ID NOs: 13 and 14, SEQ ID NOs: 17 and 18, SEQ ID NOs: 21 and 22, or SEQ ID NOs: 25 and 26.

In any of the above embodiments, the nucleic acid molecules may be isolated.

In a further aspect, the present invention provides a vector suitable for expressing one of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The invention provides vectors comprising nucleic acid molecules that encode the heavy chain of an anti-LAG-3 antibody of the invention or an antigen-binding portion thereof, the light chain of an anti-LAG-3 antibody of the invention or an antigen-binding portion thereof, or both the heavy and light chains of an anti-LAG-3 antibody of the invention or an antigen-binding portion thereof. The invention further provides vectors comprising nucleic acid molecules encoding fusion proteins, modified antibodies, antibody fragments, and probes thereof.

A nucleic acid molecule encoding the heavy and/or light chain of an anti-LAG-3 antibody or antigen-binding portion thereof of the invention can be isolated from any source that produces such an antibody or portion. In various embodiments, the nucleic acid molecules are isolated from B cells that express an anti-LAG-3 antibody isolated from an animal immunized with a human LAG-3 antigen, or from an immortalized cell produced from such a B cell. Methods of isolating nucleic acids encoding an antibody are well-known in the art. mRNA may be isolated and used to produce cDNA for use in polymerase chain reaction (PCR) or cDNA cloning of antibody genes. In certain embodiments, a nucleic acid molecule of the invention can be synthesized rather than isolated.

In some embodiments, a nucleic acid molecule of the invention can comprise a nucleotide sequence encoding a VH domain from an anti-LAG-3 antibody or antigen-binding portion of the invention joined in-frame to a nucleotide sequence encoding a heavy chain constant region from any source. Similarly, a nucleic acid molecule of the invention can comprise a nucleotide sequence encoding a VL domain from an anti-LAG-3 antibody or antigen-binding portion of the invention joined in-frame to a nucleotide sequence encoding a light chain constant region from any source.

In a further aspect of the invention, nucleic acid molecules encoding the variable domain of the heavy (VH) and/or light (VL) chains may be "converted" to full-length antibody genes. In one embodiment, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domains to a nucleic acid molecule encoding a CH and/or CL region using standard molecular biological techniques. Nucleic acid molecules encoding the full-length heavy and/or light chains may then be expressed from a cell into which they have been introduced and the anti-LAG-3 antibody isolated.

The nucleic acid molecules may be used to recombinantly express large quantities of anti-LAG-3 antibodies. The nucleic acid molecules also may be used to produce chimeric antibodies, bi-specific antibodies, single chain antibodies, immunoadhesins, diabodies, mutated antibodies and antibody derivatives, as described herein.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-LAG-3 antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of the anti-LAG-3 antibodies or antigen-binding portions thereof of the invention as described herein.

In another embodiment, the nucleic acid molecules and vectors may be used to make mutated anti-LAG-3 antibodies. The antibodies may be mutated in the variable domains of the heavy and/or light chains, e.g., to alter a binding property of the antibody. For example, a mutation may be made in one or more of the CDRs o increase or decrease the $K_D$ of the anti-LAG-3 antibody, to increase or decrease $k_{off}$, or to alter the binding specificity of the antibody. In another embodiment, one or more mutations are made at an amino acid residue that is known to be changed compared to the germline in a monoclonal antibody of the invention. The mutations may be made in a CDR or framework region of a variable domain, or in a constant region. In a preferred embodiment, the mutations are made in a variable domain. In some embodiments, one or more mutations are made at an amino acid residue that is known to be changed compared to the germline in a CDR or framework region of a variable domain of an antibody or antigen-binding portion thereof of the invention.

In another embodiment, the framework region(s) are mutated so that the resulting framework region(s) have the amino acid sequence of the corresponding germline gene. A mutation may be made in a framework region or constant region to increase the half-life of the anti-LAG-3 antibody. See, e.g., PCT Publication WO 00/09560. A mutation in a framework region or constant region also can be made to alter the immunogenicity of the antibody, and/or to provide a site for covalent or non-covalent binding to another molecule. According to the invention, a single antibody may have mutations in any one or more of the CDRs or framework regions of the variable domain or in the constant region.

In some embodiments, the anti-LAG-3 antibodies of the invention or antigen-binding portions thereof are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody coding sequence may be ligated into a vector such that transcriptional and translational control sequences within the vector serve their intended function of regulating the transcription and translation of the antibody coding sequence. The expression vector and expression control sequences may be chosen to be compatible with the expression host cell used. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can easily be inserted and expressed, as described above. The HC- and LC-encoding genes in such vectors may contain intron sequences that will result in enhanced overall antibody protein yields by stabilizing the related mRNA. The intron sequences are flanked by splice donor and splice acceptor sites, which determine where RNA splicing will occur. Location of intron sequences can be either in variable or constant regions of the antibody chains, or in both variable and constant regions when multiple introns are used. Polyadenylation and transcription termination may occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Host Cells and Methods of Antibody and Antibody Composition Production

An additional aspect of the invention relates to methods for producing the antibody compositions and antibodies and antigen-binding portions thereof of the invention. One embodiment of this aspect of the invention relates to a method for producing an antibody as defined herein, comprising providing a recombinant host cell capable of expressing the antibody, cultivating said host cell under conditions suitable for expression of the antibody, and isolating the resulting antibody. Antibodies produced by such expression in such recombinant host cells are referred to herein as "recombinant antibodies." The invention also provides progeny cells of such host cells, and antibodies produced by same.

The term "recombinant host cell" (or simply "host cell"), as used herein, means a cell into which a recombinant expression vector has been introduced. The invention provides host cells that may comprise, e.g., a vector according to the invention described above. The invention also provides host cells that comprise, e.g., a nucleotide sequence encoding the heavy chain or an antigen-binding portion thereof, a nucleotide sequence encoding the light chain or an antigen-binding portion thereof, or both, of an anti-LAG-3 antibody or antigen-binding portion thereof of the invention. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-LAG-3 antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected by determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana*, *Arabidopsis*, duckweed, corn, wheat, potato, etc. Bacterial host cells include *E. coli* and *Streptomyces* species. Yeast host cells include *Schizosaccharomyces pombe*, *Saccharomyces cerevisiae* and *Pichia pastoris*.

Further, expression of antibodies of the invention or antigen-binding portions thereof from production cell lines can be enhanced using a number of known techniques. For example, the glutamine synthetase gene expression system (the GS system) is a common approach for enhancing expression under certain conditions. The GS system is discussed in whole or part in connection with EP Patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein are part of the instant invention, regardless of the glycosylation state of the antibodies, and more generally, regardless of the presence or absence of post-translational modification(s).

Pharmaceutical Compositions

Another aspect of the invention is a pharmaceutical composition comprising as an active ingredient (or as the sole active ingredient) an anti-LAG-3 antibody or antigen-binding portion thereof, bi-specific binding molecule, or antibody composition of the invention. The pharmaceutical composition may comprise any anti-LAG-3 antibody or antigen-binding portion thereof, bi-specific binding molecule, or antibody composition as described herein. In some embodiments, the pharmaceutical compositions are intended for amelioration, prevention, and/or treatment of a LAG-3-related disorder and/or cancer. As used herein, a LAG-3-related or -mediated disorder refers to a disorder, disease or condition that improves, or slows down in its progression, by modulation of LAG-3 activity. In some embodiments, the compositions are intended for activation of the immune system. In certain embodiments, the compositions are intended for amelioration, prevention, and/or treatment of cancer originating in tissues such as skin, lung, intestine, colon, ovary, brain, prostate, kidney, soft tissues, the hematopoietic system, head and neck, liver, bladder, breast, stomach, uterus and pancreas. In certain embodiments, the cancer is fibrosarcoma, lung carcinoma, or melanoma. In certain embodiments, the cancer is glioblastoma, gliosarcoma, or colorectal cancer. In certain embodiments, the pharmaceutical compositions of the invention are intended for treatment of psoriasis.

Generally, the antibodies, antigen-binding portions, and bi-specific binding molecules of the invention are suitable to be administered as a formulation in association with one or more pharmaceutically acceptable excipient(s), e.g., as described below.

Pharmaceutical compositions of the invention will comprise one or more anti-LAG-3 antibodies, binding portions, or bi-specific binding molecules of the invention, e.g., one or two anti-LAG-3 antibodies, binding portions, or bi-specific binding molecules. In one embodiment, the composition comprises a single anti-LAG-3 antibody of the invention or binding portion thereof.

In another embodiment, the pharmaceutical composition may comprise at least one anti-LAG-3 antibody or antigen-binding portion thereof, e.g., one anti-LAG-3 antibody or portion, and one or more additional antibodies that target one or more relevant cell surface receptors, e.g., one or more cancer-relevant receptors.

The term "excipient" is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and antigen-binding portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions, and kidney dialytic infusion techniques. Regional perfusion is also contemplated. Particular embodiments include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-LAG-3 antibody, antigen-binding portion thereof, bi-specific binding molecule, or antibody composition in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin, and/or by using modified-release coatings (e.g., slow-release coatings).

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antibody of the invention per actuation and the actuation volume may for example vary from 1 µL to 100 µL.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic Uses of Antibodies and Compositions of the Invention

In one aspect, the anti-LAG-3 antibodies and antigen-binding portions thereof, anti-LAG-3 compositions, and bi-specific binding molecules of the invention are used to enhance or activate the immune system in a human in need thereof. In some embodiments, the patient is immune-suppressed. For example, a physician can boost the anti-cancer activity of a patient's own immune system by administering an anti-LAG-3 antibody of the present invention, alone or in combination with other therapeutic agents (sequentially or concurrently). The LAG-3 antibody modulates the activity of LAG-3 in immune cells, resulting in enhancement of anti-cancer immunity.

In certain embodiments, the antibody or antigen-binding portion thereof, composition, or bi-specific binding molecule is for use in the treatment of cancer, e.g., cancers that originate in tissues such as skin, lung, intestine, colon, ovary, brain, prostate, kidney, soft tissues, the hematopoietic system, head and neck, liver, bladder, breast, stomach, uterus and pancreas and any cancers or other conditions which rely on LAG-3 activity and/or in which the patient expresses or overexpresses a LAG-3 ligand (e.g., MHCII, LSECtin, or both).

In some embodiments, cancers treated by the anti-LAG-3 antibodies, antigen-binding portions, bi-specific binding molecules, and/or antibody compositions of the invention may include, e.g., melanoma (e.g., advanced or metastatic melanoma), non-small cell lung cancer, head and neck squamous cell cancer, renal cell carcinoma, Hodgkin's lymphoma, non-Hodgkin's lymphoma, glioblastoma, glioma, squamous cell lung cancer, small-cell lung cancer, hepatocellular carcinoma, bladder cancer, upper urinary tract cancer, esophageal cancer, gastroesophageal junction cancer, gastric cancer, liver cancer, colon cancer, colorectal carcinoma, multiple myeloma, sarcomas, acute myeloid leukemia, chronic myeloid leukemia, myelodysplastic syndrome, nasopharyngeal cancer, chronic lymphocytic leukemia, acute lymphoblastic leukemia, small lymphocytic lymphoma, ovarian cancer, gastrointestinal cancer, primary peritoneal cancer, fallopian tube cancer, urothelial cancer, HTLV-associated T-cell leukemia/lymphoma, prostate cancer, genitourinary cancer, meningioma, adrenocortical cancer, gliosarcoma, fibrosarcoma, kidney cancer, breast cancer, pancreatic cancer, endometrial cancer, skin basal cell cancer, cancer of the appendix, biliary tract cancer, salivary gland cancer, advanced Merkel cell cancer, diffuse large B cell lymphoma, follicular lymphoma, mesothelioma, or solid tumors. The cancer may be, e.g., at an early, intermediate, late, or metastatic stage.

In some embodiments, cancers treated by the anti-LAG-3 antibodies, antigen-binding portions, compositions, and/or bi-specific binding molecules of the invention may include, e.g., hematologic malignancies, glioblastoma (e.g., recurrent glioblastoma), gliosarcoma, non-small cell lung cancer (e.g., advanced non-small cell lung cancer), colorectal cancer, and solid tumors.

In one aspect, the anti-LAG-3 antibodies and antigen-binding portions thereof, antibody compositions, or bi-specific binding molecules of the invention may be used to treat an immune-mediated disorder such as psoriasis, systemic lupus erythematosis, MLS (sclerosis), Crohn's disease, diabetes mellitus, and/or colitis ulcerotis.

In some embodiments, the anti-LAG-3 antibodies and antigen-binding portions thereof, antibody compositions, or bi-specific binding molecules of the invention may be used to treat viral and/or parasitic infections, e.g., where the pathogens inhibit the host immune response. For example, the pathogen may be, e.g., HIV, hepatitis (A, B, or C), human papilloma virus (HPV), lymphocytic choriomeningitis virus (LCMV), adenovirus, flavivirus, echovirus, rhinovirus, coxsackie virus, cornovirus, respiratory syncytial virus, mumps virus, rotavirus, measles virus, rubella virus, parvovirus, vaccinia virus, human T-cell lymphotrophic virus (HTLV), dengue virus, molluscum virus, poliovirus, rabies virus, John Cunningham (JC) virus, arboviral encephalitis virus, simian immunodeficiency virus (SIV), influenza, herpes, Giardia, malaria, *Leishmania, Staphylococcus aureus*, or *Pseudomonas aeruginosa*.

In some embodiments, the anti-LAG-3 antibodies and antigen-binding portions thereof, antibody compositions, or bi-specific binding molecules of the invention may be used to treat a patient who is, or is at risk of being, immunocompromised (e.g., due to chemotherapeutic or radiation therapy).

In some embodiments, the anti-LAG-3 antibodies and antigen-binding portions thereof, antibody compositions, or bi-specific binding molecules of the invention may be used for ex vivo activation and expansion of antigen-specific T cells.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may, for example, result in tumor shrinkage, increased survival, elimination of cancer cells decreased disease progression, reversal of metastasis, or other clinical endpoints desired by healthcare professionals.

The anti-LAG-3 antibodies or antigen-binding portions thereof, antibody compositions, or bi-specific binding molecules of the invention may be administered alone or in combination with one or more other drugs or antibodies (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with," referring to the anti-LAG-3 antibodies and antigen-binding portions thereof, antibody compositions, and bi-specific binding molecules of the invention with one or more other therapeutic agents, is intended to mean, and does refer to and include the following:

a) simultaneous administration of such combination of antibody/antigen-binding portion/antibody composition/bi-specific binding molecule of the invention and therapeutic agent(s) to a patient in need of treatment, when such components are formulated together into a single dosage form which releases said components at substantially the same time to said patient, b) substantially simultaneous administration of such combination of antibody/antigen-binding portion/antibody composition/bi-specific binding molecule of the invention and therapeutic agent(s) to a patient in need of treatment, when such components are formulated apart from each other into separate dosage forms which are taken at substantially the same time by said patient, whereupon said components are released at substantially the same time to said patient, c) sequential administration of such combination of antibody/antigen-binding portion/antibody composition/bi-specific binding molecule of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and d) sequential administration of such combination of antibody/antigen-binding portion/antibody composition/bi-specific binding molecule of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The anti-LAG-3 antibodies and antigen-binding portions thereof, antibody compositions, or bi-specific binding molecules of the invention may be administered without additional therapeutic treatments, i.e., as a stand-alone therapy (monotherapy). Alternatively, treatment with the anti-LAG-3 antibodies and antigen-binding portions thereof, antibody compositions, or bi-specific binding molecules of the invention may include at least one additional therapeutic treatment (combination therapy), e.g., another immunostimulatory agent, an anti-cancer agent, an anti-viral agent, or a vaccine (e.g., a tumor vaccine).

In some embodiments, the antibody or antigen-binding portion thereof, antibody composition, or bi-specific binding molecule may be co-administered or formulated with another medication/drug for the treatment of cancer. The additional therapeutic treatment may comprise, e.g., a chemotherapeutic, anti-neoplastic, or anti-angiogenic agent, a different anti-cancer antibody, and/or radiation therapy.

By combining the antibodies or antigen-binding portions thereof, antibody compositions, or bi-specific binding molecules of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. In some embodiments, the compound is selected from the group consisting of retinoic acid, phenylbutyrate, all-trans-retinoic acid and active form vitamin D.

Pharmaceutical articles comprising an anti-LAG-3 antibody or antigen-binding portion thereof, antibody composition, or bi-specific binding molecule of the invention and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, e.g., fluorouracil and/or other fluoropyrimidines. In some embodiments, the other agent is dacarbazine or gemcitabine.

An anti-LAG-3 antibody or antigen-binding portion thereof, antibody composition, or bi-specific binding molecule of the invention may also be used in combination with other anti-cancer therapies such as vaccines, cytokines, enzyme inhibitors, immunostimulatory compounds, and T cell therapies. In the case of a vaccine, it may, e.g., be a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example 1-methyl-D-tryptophan (1-D-MT). Adoptive T cell therapy refers to various immunotherapy techniques that involve expanding or engineering patients' own T cells to recognize and attack their tumors.

It is also contemplated that an anti-LAG-3 antibody or antigen-binding portion thereof, antibody composition, or bi-specific binding molecule of the invention may be used in adjunctive therapy in connection with tyrosine kinase inhibitors. These are synthetic, mainly quinazoline-derived, low molecular weight molecules that interact with the intracellular tyrosine kinase domain of receptors and inhibit ligand-induced receptor phosphorylation by competing for the intracellular Mg-ATP binding site.

In some embodiments, the antibody or antigen-binding portion thereof, antibody composition, or bi-specific binding molecule may be used in combination with another medication/drug that mediates immune system activation, including, but not limited to, an agent that modulates the expression or activity of A2AR, BTLA, B7-H3, B7-H4, CTLA-4, CD27, CD28, CD40, CD47, CD55, CD73, CD122, CD137, CD160, CGEN-15049, CHK1, CHK2, CTLA-3, CEACAM (e.g., CEACAM-1 and/or CEACAM-5), GAL9, GITR, HVEM, LY108, LAIR1, ICOS, IDO, KIR, LAIR1, PD-1/PD-L1/PD-L2, OX40, TIGIT, TIM-3, TGFR-beta, VISTA, LILRB2, CMTM6 and/or 2B4. In certain embodiments, the agent is an antibody or an antigen-binding fragment thereof that binds to one of the above molecules. It is also contemplated that an anti-LAG-3 antibody or antigen-binding portion thereof, antibody composition, or bi-specific binding molecule of the invention may be used in combination with a cytokine (e.g., IL-1, IL-2, IL-12, IL-15 or IL-21), an EGFR inhibitor, a VEGF inhibitor, etc.

In certain aspects, the antibodies and antigen-binding portions, antibody compositions, or bi-specific binding molecules of the invention may be administered in combination with another inhibitor of the LAG-3 pathway, which may target LAG-3 or one or more of its ligands. Examples of such inhibitors include other anti-LAG-3 antibodies, anti-MHCII antibodies, anti-Galectin-3 antibodies, and anti-LSECtin antibodies. In some embodiments, an anti-LAG-3 antibody or antigen-binding portion thereof, bi-specific antibody, or antibody composition of the invention may be administered in combination with BMS-986016, GSK2831781, REGN3767, BAP050 or BAP050-chi, or LAG525.

It is understood that the antibodies and antigen-binding portions thereof, antibody compositions, and bi-specific binding molecules of the invention may be used in a method of treatment as described herein, may be for use in a treatment as described herein, and/or may be for use in the manufacture of a medicament for a treatment as described herein. The invention also provides kits and articles of manufacture comprising the antibodies and antigen-binding portions thereof, antibody compositions, and bi-specific binding molecules described herein.

Dose and Route of Administration

The antibodies or antigen-binding portions thereof, antibody compositions, or bi-specific binding molecules of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated, each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

It is contemplated that a suitable dose of an antibody, antigen-binding portion, antibody composition, or bi-specific binding molecule of the invention will be in the range of 0.1-100 mg/kg, such as about 0.5-50 mg/kg, e.g., about 1-20 mg/kg. The antibody, antigen-binding portion, antibody composition, or bi-specific binding molecule may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

An effective amount for tumor therapy may be measured by its ability to stabilize disease progression and/or ameliorate symptoms in a patient, and preferably to reverse disease progression, e.g., by reducing tumor size. The ability of an antibody, antigen-binding portion, antibody composition, or bi-specific binding molecule of the invention to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

Diagnostic Uses and Compositions

The antibodies of the present invention also are useful in diagnostic processes (e.g., in vitro, ex vivo). For example, the antibodies can be used to detect and/or measure the level of LAG-3 in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassay, and immunohistology. The invention further encompasses kits (e.g., diagnostic kits) comprising the antibodies described herein.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Example 1: Generation and Screening of Anti-LAG-3 Antibody Repertoires

Two anti-LAG-3 antibody repertoires were generated by immunization with LAG-3 extracellular domain (ECD) or LAG-3 ECD Fc fusion protein. One antibody library was prepared from single-cell sorted B cells from immunized OmniRat® rats using Symplex™ antibody discovery technology (Osborn et al., *J Immunol.* 190(4): 1481-90 (2013); Meijer et al., *J Mol Biol.* 358(3): 764-72 (2006)). The expression constructs from this antibody repertoire encoded fully human immunoglobulins in $IgG_1$ format carrying two mutations (L234A/L235A) known to reduce effector function of the Fc region of $IgG_1$ antibodies (Hezareh et al., *J Virol.* 75(24):12161-8 (2001)). A second antibody repertoire was constructed using single-cell sorted B cells originating from the lymphoid organs of immunized wild-type chickens (*Gallus gallus*).

Cloned antibodies from both anti-LAG-3 repertoires were individually transfected and expressed in HEK293 cells using 293Fectin™ Transfection Reagent (Invitrogen, Cat. No. 12347-019) in 384-well format, and antibody-containing supernatants were collected on day 6 after transfection.

For cell-based antibody screening, CHO-S cells were transfected in 384-well format to express GPI-anchored human LAG-3 using the FreeStyle™ MAX reagent (Invitrogen, Cat. No. 16447-100), and cells transfected with an irrelevant, GPI-anchored control protein were used as a negative control. In order to allow for a multiplexed screening setup, control cells were labeled using carboxyfluorescein succinimidyl ester (CFSE) and mixed with non-labeled LAG-3-transfected cells at a ratio of 1 to 1, and a density of $1 \times 10^6$ cells per mL. In 384-well plates, 40 μL of this cell mix was mixed with 10 μL of antibody-containing supernatant, and cell-bound antibody was revealed by addition of goat anti-human IgG (H+L) AF647 secondary antibody (Molecular Probes, Cat. No. A21445). In parallel, antibodies were screened for binding to cynomolgus LAG-3 in a similar setup. Samples were obtained using high throughput flow cytometry (iQue® Screener, Intellicyt) and data was analyzed using ForeCyt® software by plotting CFSE vs. human IgG binding (AF647). LAG-3-specific primary hits were identified as antibody clones binding to both human and cynomolgus LAG-3-transfected cells (CSFE negative), but not to control cells (CFSE positive), and plate numbers and plate coordinates were collected for hit picking and subsequent sequence analysis.

The heavy and light chain variable region DNA and protein sequences of six functional OmniRat®-derived anti-LAG-3 antibodies (15646, 15532, 15723, 15595, 15431, and 15572) and one functional chicken-derived anti-LAG-3 antibody (15011; see Example 2) are provided in the sequence list section below. An overview of the SEQ ID numbers of the variable and constant region DNA and protein sequences is provided in Tables 8 and 9. SEQ ID numbers for the CDRs are found in Table 9. The CDR sequences herein were determined according to the IMGT® definitions for CDR1 and CDR2. For heavy and light chain CDR3, the definitions herein include one extra amino acid residue upstream of the IMGT-CDR3 (Cys) and one extra amino acid residue downstream (Trp for H-CDR3, Phe for L-CDR3). Germline gene usage of the six OmniRat®-derived antibodies is shown in Table 10.

Example 2: Humanization of Chicken-Derived Anti-LAG-3 Antibodies

Humanization of the framework regions of the chicken-derived anti-LAG-3 antibodies was performed in order to produce antibody molecules having minimal immunogenicity when administered to humans, while substantially retaining the specificity and affinity of the parental chicken antibodies.

Humanization of the chicken-derived antibody was performed using the "CDR grafting" approach, a method originally described by Jones et al., Nature 321(6069):522-5 (1986). First, the variable heavy (VH) and variable light (VL) regions of the antibodies were blasted against human IgG databases in order to find the closest human germline genes. This identified the IGHV3-23*01 (M99660) and human IGLV3-19*01 (X56178) genes as being closest to the chicken VH and VL genes, respectively. Similarly, the selected human amino acid sequences for J-gene region humanization were derived from IGHJ1*01 (J00256) and IGLJ6*01 (M18338) for VH and VL, respectively. The antibody VH and VL genes were then aligned against chicken immunoglobulin germline genes to identify somatic mutations in the framework regions that may play a role in antibody function and/or structure. Finally, certain amino acid positions, so-called "Vernier residues" (Nishibori et al., Mol Immunol. 43(6):634-42 (2006)), that are known to play an important role in antibody structure, stability and function, were considered for generating alternative humanized antibody variants including either human or chicken residues from the corresponding germlines.

Assembly of the chicken CDR and human framework regions was performed in silico and synthetic genes encoding humanized VH and VL were ordered from Genscript Inc. The VH and VL genes were cloned in expression vectors (plasmids) harboring the constant regions of human antibody light chain and heavy chain. Specifically, the VL was joined to the human lambda constant IGLC1*01 (J00252). In order to increase correct cleavage of the signal peptide upstream of the lambda chain, the second amino acid (Ser) of the Lambda gene IGLV3.19 was replaced by another amino acid (Tyr) which is present in other human germlines, for example IGLV3.25.

Figure 1B:
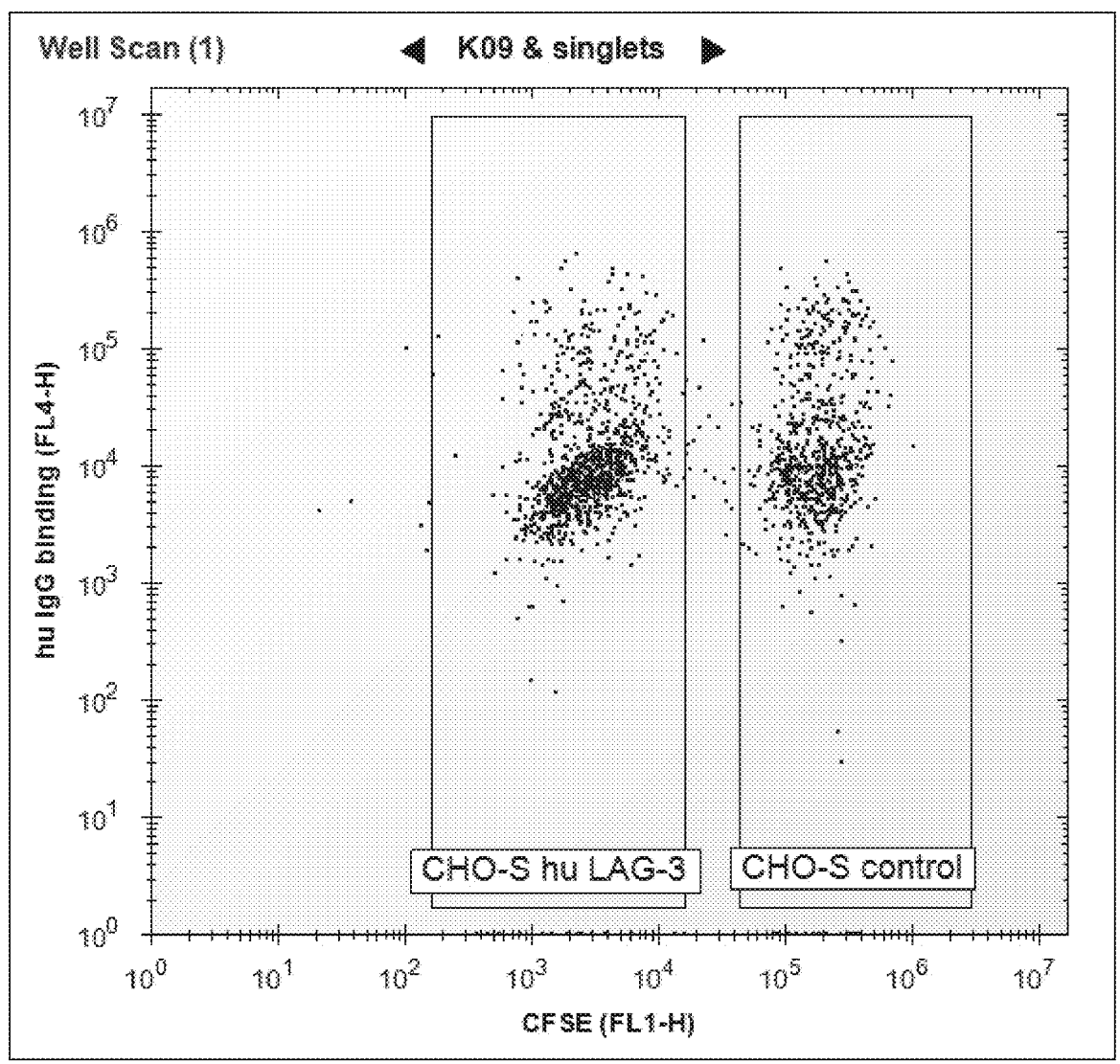
Figure 1C:
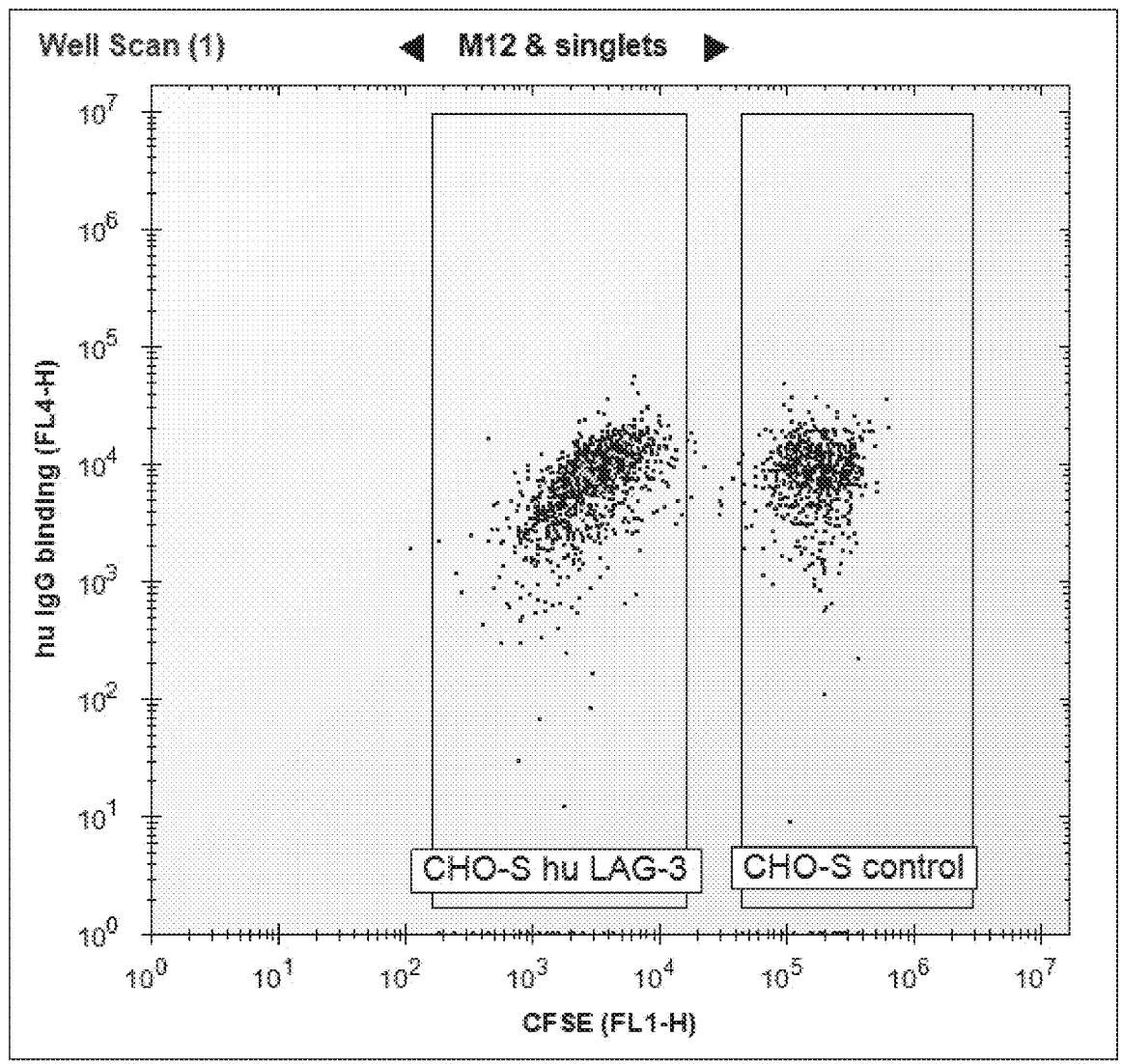

Representative flow cytometry dot plots for antibody clones generated as described in this example are shown in FIGS. 1A-C: (A) an antibody clone binding specifically to human LAG-3-transfected cells, (B) an antibody clone binding non-specifically to CHO-S cells, and (C) an antibody clone that does not bind to any of the cell populations used in the screening.

Example 3: Cloning of Anti-LAG-3 Reference Antibody Analogues

Amino acid sequences encoding the heavy and light chain variable domains of antibody analogues of 25F7-Lag3.5 and BAP050 were obtained from U.S. Patent Application Publication 2014/0093511 A1 (SEQ ID NOs: 12 and 14) and PCT Patent Application Publication WO 2015/138920 AI (SEQ ID NOs: 6 and 16), respectively. The protein sequences were reverse translated to DNA sequences with human codon usage. The corresponding DNA sequences were then synthesized and cloned into expression vectors comprising a coding sequence for human $IgG_4$ heavy chain or kappa light chain constant domain, resulting in expression of full-length antibodies. To prevent Fab arm exchange, the serine residue at position 228 was substituted with proline (Angal et al., Mol. Immunol. 30:105-108 (1993)). CHO cells were transfected with the resulting expression plasmids using a standard protein expression system. The corresponding antibody supernatants were purified using standard protein A purification column chromatography.

Example 4: Screening of a Panel of LAG-3 Specific mAbs in the SEB+PBMC Assay The ability of a large panel of LAG-3 specific mAbs to stimulate IL-2 secretion from Staphylococcal enterotoxin B (SEB) treated peripheral blood mononuclear cells (PBMCs) was evaluated using PBMCs from a single donor. SEB is a super-antigen that binds to MHC class II molecules and specific Vβ regions of T cell receptors (TCR) and drives non-specific stimulation of T-cells. This results in polyclonal T cell activation/proliferation and release of cytokines, including IL-2. Human PBMCs isolated from buffy coats from healthy donors were seeded in 384 well plates and left untreated or treated with 10 ng/mL SEB and 10 μg/mL of the antibodies. After 48 hours in a humidified incubator at 37° C., supernatants were removed and analyzed for IL-2 levels using an IL-2 ELISA kit (Life Technologies).

Figure 2:
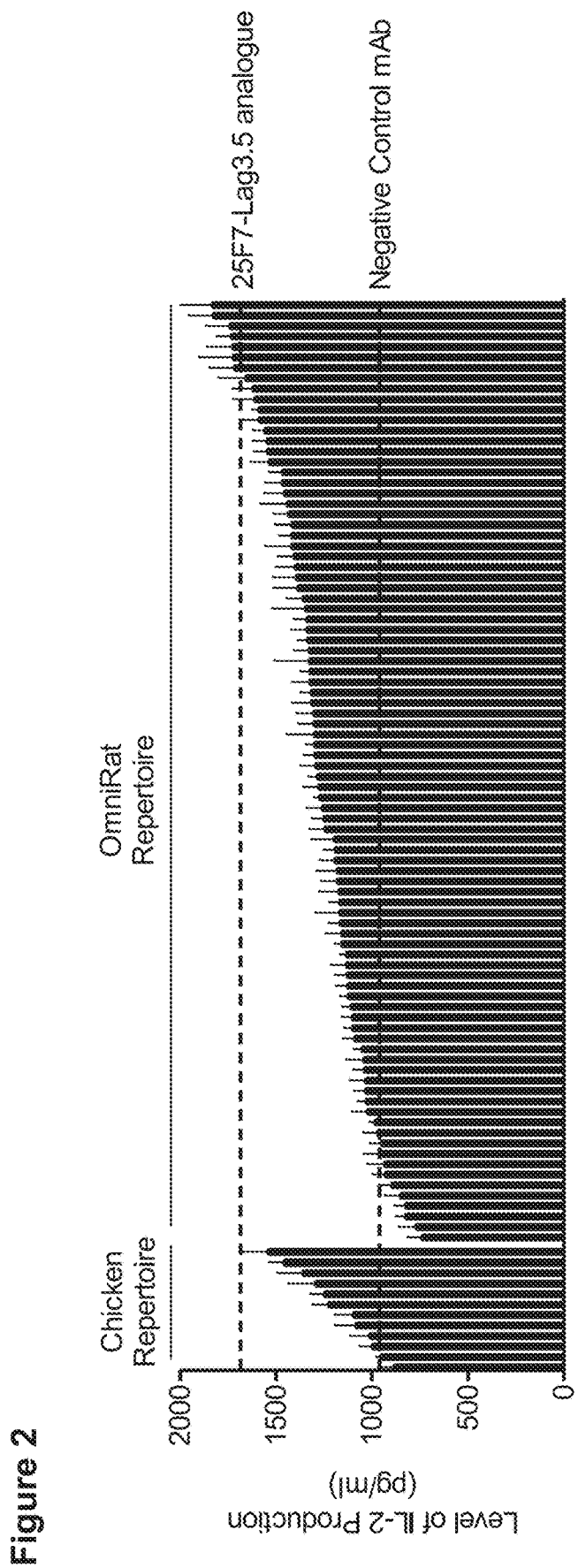
FIG. 2 shows the level of IL-2 production from SEB-stimulated PBMCs after treatment with anti-LAG-3 monoclonal antibodies.

The increase in IL-2 secretion after treatment with the anti-LAG-3 mAb repertoires or the 25F7-Lag3.5 analogue is seen in FIG. 2. It is evident that the IL-2 levels after treatment with the different anti-LAG-3 mAbs varied strongly, showing that some antibodies in the repertoire had no functionality in this assay, whereas other antibodies induced IL-2 secretion to similar levels as the 25F7-Lag3.5 analogue.

Example 5: Antibody Binding to Cell-Expressed Human or Cynomolgus LAG-3

To determine EC50 values for binding of antibodies by flow cytometry, CHO-S cells were transiently transfected to express human or cynomolgus LAG-3 using the FreeStyle™ MAX reagent (Invitrogen, Cat. No. 16447-100). Antibodies were titrated in 3-fold dilutions down from 10 to 0.05 µg/mL in staining buffer (PBS; 2% FBS; NaN$_3$) and mixed and incubated with either the human or cynomolgus LAG-3-transfected cells. After two washes in staining buffer, cell-bound antibody was revealed by addition of goat anti-human IgG (H+L) AF647 secondary antibody (Molecular Probes, Cat. No. A21445). Samples were obtained using high throughput flow cytometry (iQue® Screener, Intellicyt) and data was analyzed using ForeCyt® software by plotting antibody concentration vs. mean fluorescence intensity (MFI) for AF647. EC50 values were calculated using the "dose response graph" feature in ForeCyt®.

A summary of antibody binding properties measured by titration is found in Table 1 below, where huLAG-3 and cyLAG-3 are human and cynomolgus LAG-3-transfected cells, respectively. As shown in Table 1, antibodies 15646, 15532, 15723, 15595, 15431, and 15572 bind to both human and cynomolgus LAG-3.

TABLE 1

Antibody properties overview

| Antibody | Source | EC50 by FACS-huLAG-3 (nM) | EC50 by FACS-cyLAG-3 (nM) |
| --- | --- | --- | --- |
| 15646 | OmniRat® | 0.10 | 0.11 |
| 15532 | OmniRat® | 0.07 | 0.05 |
| 15723 | OmniRat® | 0.09 | 0.26 |
| 15595 | OmniRat® | 0.05 | 0.03 |
| 15431 | OmniRat® | 0.04 | 0.04 |
| 15572 | OmniRat® | 0.07 | 0.06 |
| 15011 | chicken | NA | NA |

Example 6: Flow Cytometric Analysis of Anti-LAG-3 Antibodies for MHCII Blocking Activity This example illustrates how the anti-LAG-3 antibodies were tested for major histocompatibility complex II (MHCII) blocking activity by performing a flow cytometric competition assay using surface-MHCII-positive A375 cells and fluorochrome-labeled soluble LAG-3.

MHCII blocking activity was investigated in a cell-based assay using the human melanoma cell line A375 (ATCC® CRL-1619™). R-PE-labeled human LAG-3-Fc chimera protein can specifically bind to surface-expressed MHCII on A375, allowing quantification of this interaction by flow cytometry. Commercially available recombinant human LAG-3-Fc chimera protein (R&D Systems, USA) was conjugated to R-PE using the Lightning-Link® R-Phycoerythrin Conjugation Kit (Innova Biosciences, UK). A375 cells were harvested using enzyme-free Cell Dissociation Buffer (Gibco™), washed, and re-suspended in cold staining buffer (PBS, 2% FBS, NaN$_3$). Anti-LAG-3 antibodies to be tested were plated in 96-well format and adjusted to 20 µg/mL in 50 µL staining buffer. 1 µL of LAG-3-Fc-PE (corresponding to approx. 0.17 µg LAG-3-Fc) was added per well, mixed, and plates were incubated at 4° C. for 30 mins to allow LAG-3-antibody complex formation. During incubation, 1×10$^5$ A375 cells (in 100 µL staining buffer) were plated in 96-well format, sedimented by centrifugation, and cell pellets were re-suspended in the pre-incubated LAG-3/antibody mixtures. Cells were incubated for additional 20 mins at 4° C., washed 1× in 200 µL cold staining buffer, and re-suspended in 100 µL staining buffer for acquisition.

Of the seven anti-LAG-3 antibodies tested (at 20 µg/mL), four, 15532, 15595, 15431 and 15011, induced a reduction of LAG-3 binding to MHCII (MFI) by approximately 90% compared to binding in the presence of a negative control antibody, and are thus considered effective blockers of the interaction. The remaining three antibodies, 15646, 15723 and 15572, only had limited effect on LAG-3-MHCII-binding and may be considered poor blockers. The reference antibody 25F7-Lag3.5 analogue displayed intermediate blocking activity. The results are summarized in Table 2.

TABLE 2

Blocking of LAG-3 binding to MHCII on A375 cells in the presence of anti-LAG-3 antibodies.

| Antibody | LAG-3/MHCII Blocking (%)* |
| --- | --- |
| 15646 | 49 |
| 15532 | 89 |
| 15723 | 55 |
| 15595 | 94 |
| 15431 | 92 |
| 15572 | 37 |
| 15011 | 92 |
| 25F7-Lag3.5 analogue | 77 |

*Median, normalized to LAG-3 binding in the presence of a negative control antibody.

Example 7: Efficacy of Anti-LAG-3 Monoclonal Antibodies in SEB+PBMC Assay

The ability of the seven anti-LAG-3 mAbs to stimulate IL-2 secretion from Staphylococcal enterotoxin B (SEB) treated peripheral blood mononuclear cells (PBMCs) was evaluated. This example describes the efficacy of the seven anti-LAG-3 mAbs in several PBMC donors. In addition, the efficacy of four anti-LAG-3 mAbs from other sequence clusters is described. Sequence cluster numbers are shown in brackets after the antibody numbers and are further described in Example 13. The anti-LAG-3 antibodies were tested at 10 or 12.5 µg/ml in a SEB+PBMC assay as described in Example 4.

Figure 3:
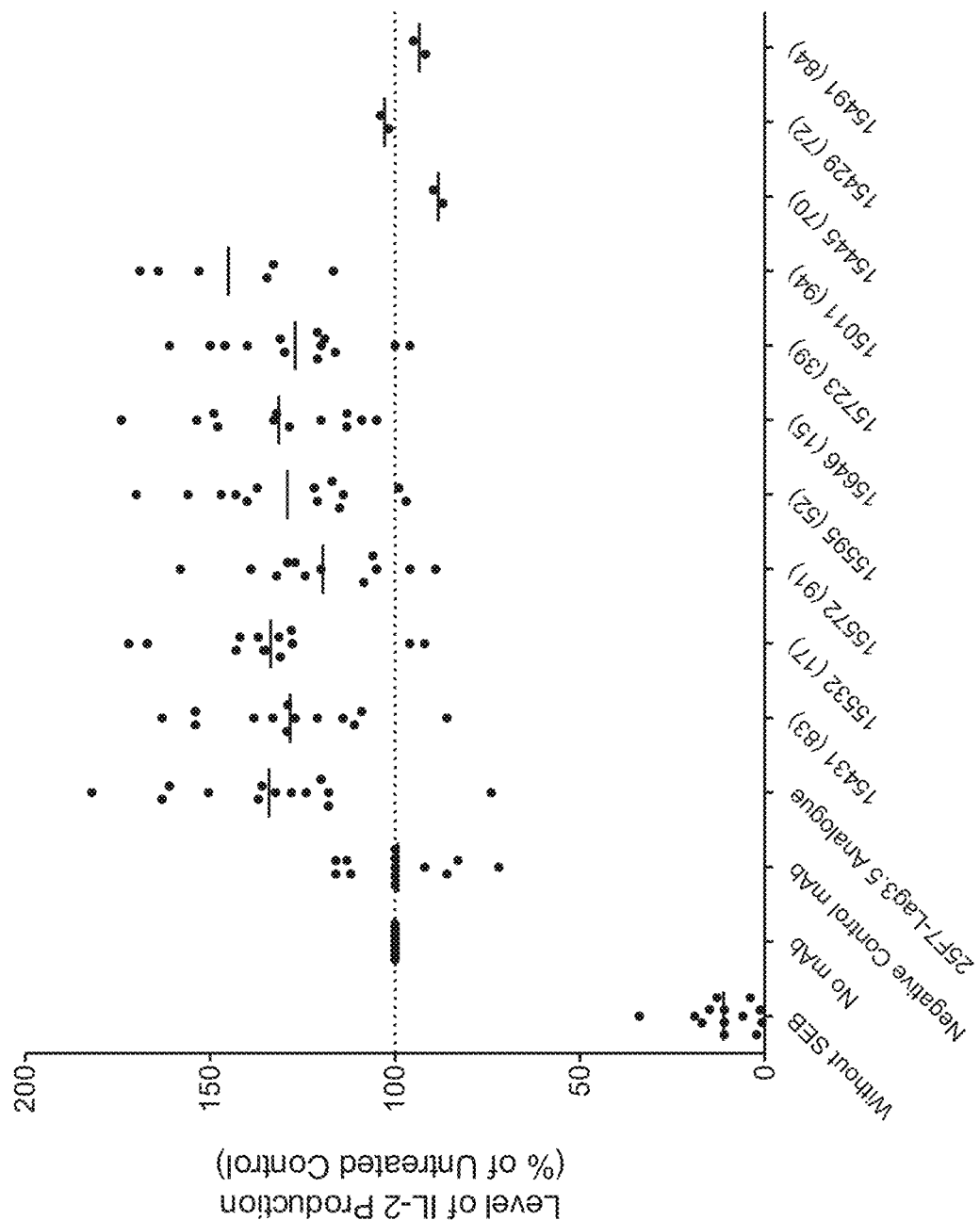
FIG. 3 shows the level of IL-2 production from SEB-stimulated PBMCs after treatment with anti-LAG-3 monoclonal antibodies. Each dot represents the level of IL-2 secretion from a single PBMC donor.

The increase in IL-2 secretion after treatment with the anti-LAG-3 mAbs 15431, 15532, 15572, 15595, 15646, 15723, and 15011 or the 25F7-Lag3.5 analogue is shown in FIG. 3. Each dot represents the level of IL-2 secretion from a single PBMC donor. It is evident that the IL-2 levels after treatment with the anti-LAG-3 mAbs varied among the different PBMC donors, but all seven anti-LAG-3 mAbs stimulated IL-2 production to similar levels. This is in contrast to the anti-LAG-3 mAbs 15445, 15429 and 15491, which do not increase IL-2 production.

Example 8: Effect of Anti-LAG-3 Monoclonal Antibodies in Cell-Based LAG-3-MHC Class II Blocking Assay To characterize the seven anti-LAG-3 mAbs further, the ability to block the LAG-3-MHC class II interaction was tested in a cell based assay.

Figure 4:
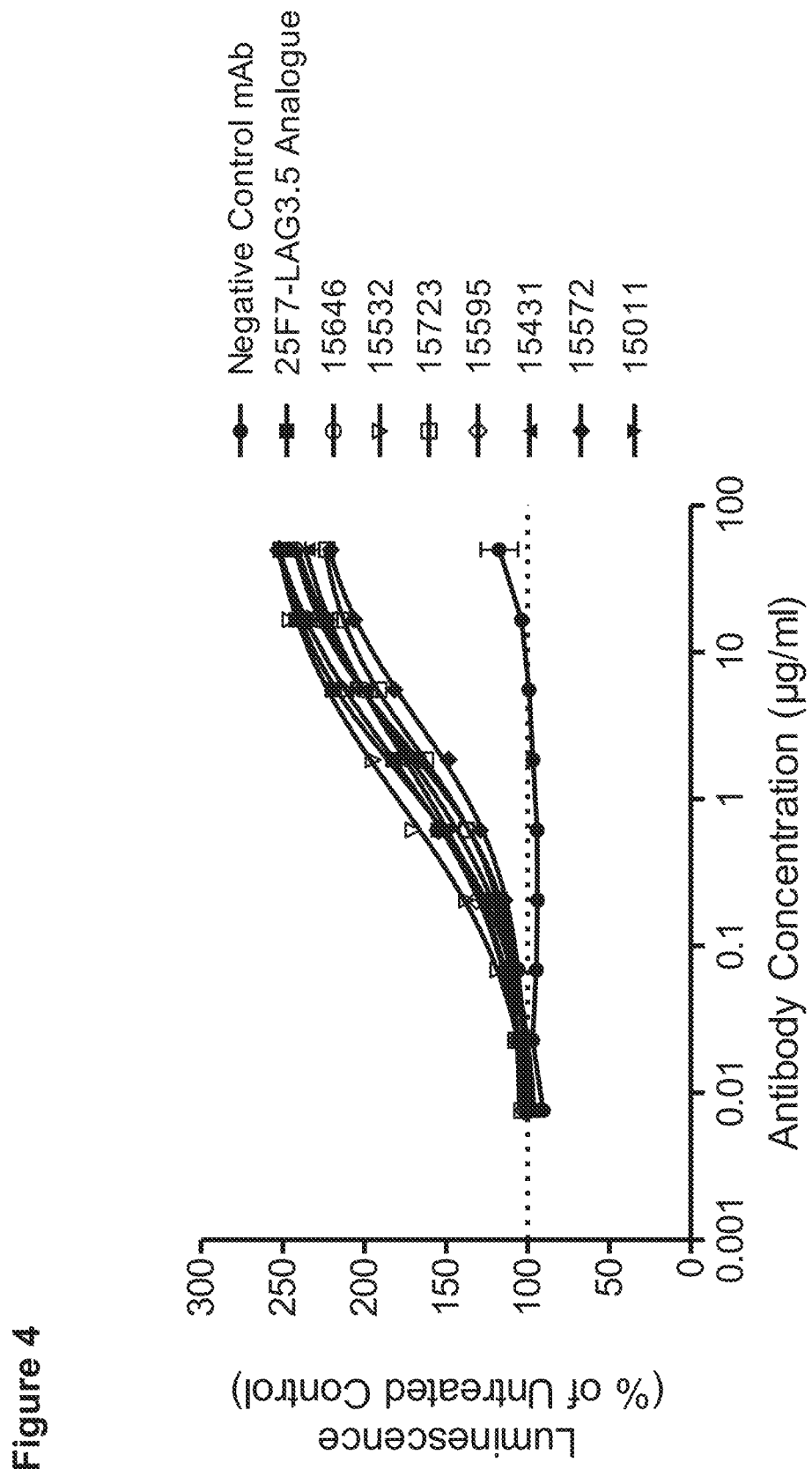
FIG. 4 shows the level of luminescence in a LAG-3-MHC class II blocking assay after treatment with anti-LAG-3 monoclonal antibodies. Data are presented as means±SEM.

Jurkat cells harboring an NFAT-RE-controlled luciferase gene and expressing a modified TCR and LAG-3 (Promega) were incubated with the MHC class II-expressing Raji cell line, 50 ng/mL Staphylococcal enterotoxin D (SED) and different concentrations of monoclonal antibodies as indicated in FIG. 4. After 6 hours in a humidified incubator at 37° C., luciferase substrate (Promega) was added and luminescence was measured. Luminescence is a measure of luciferase expression, which is controlled by TCR signaling and inhibited by LAG-3 signaling. Thus, less LAG-3 signaling, e.g., by blocking the LAG-3-MHCII interaction, will lead to increased luminescence.

The increase in luminescence after treatment with the anti-LAG-3 mAbs 15431, 15532, 15572, 15595, 15646, 15723, and 15011 or the 25F7-Lag3.5 analogue is shown in FIG. 4. All of the tested anti-LAG-3 antibodies were found to increase the luminescence to similar levels.

Example 9: Effect of Anti-LAG-3 Monoclonal Antibodies on Cellular Levels of LAG-3

To characterize selected anti-LAG-3 mAbs further, the ability to down-modulate LAG-3 levels was tested in a T-cell line overexpressing LAG-3.

Figure 5:
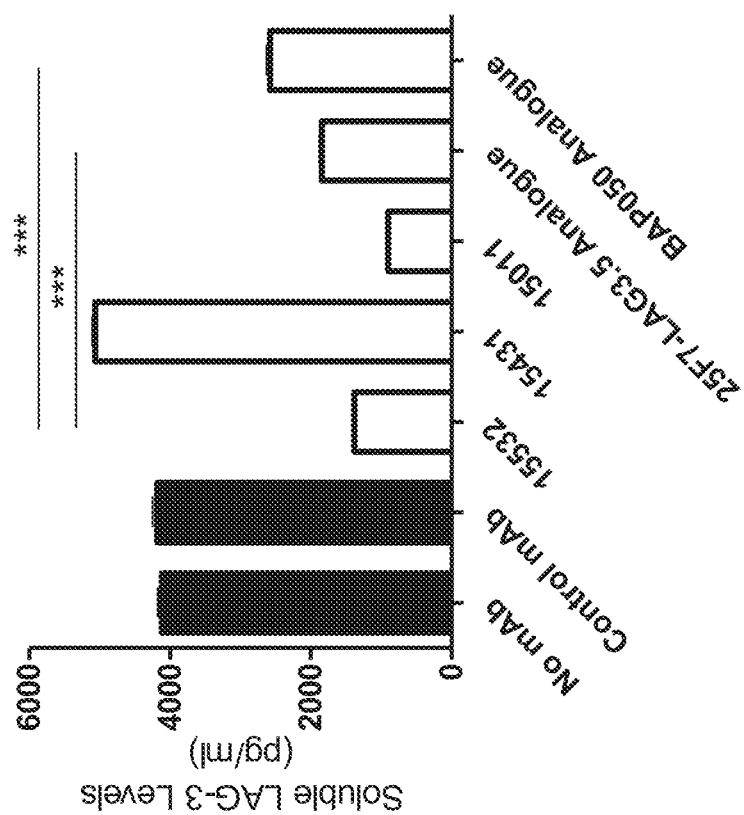
FIG. 5 shows the levels of LAG-3 in lysates and supernatants from a LAG-3 transfected T cell line after treatment with anti-LAG-3 monoclonal antibodies. Data are presented as means±SEM. Asterisks indicate a statistically significant difference between 15532 and reference antibody analogues (*: $p<0.05$, *: $p<0.001$, **: $p<0.0001$).
Figure 5:
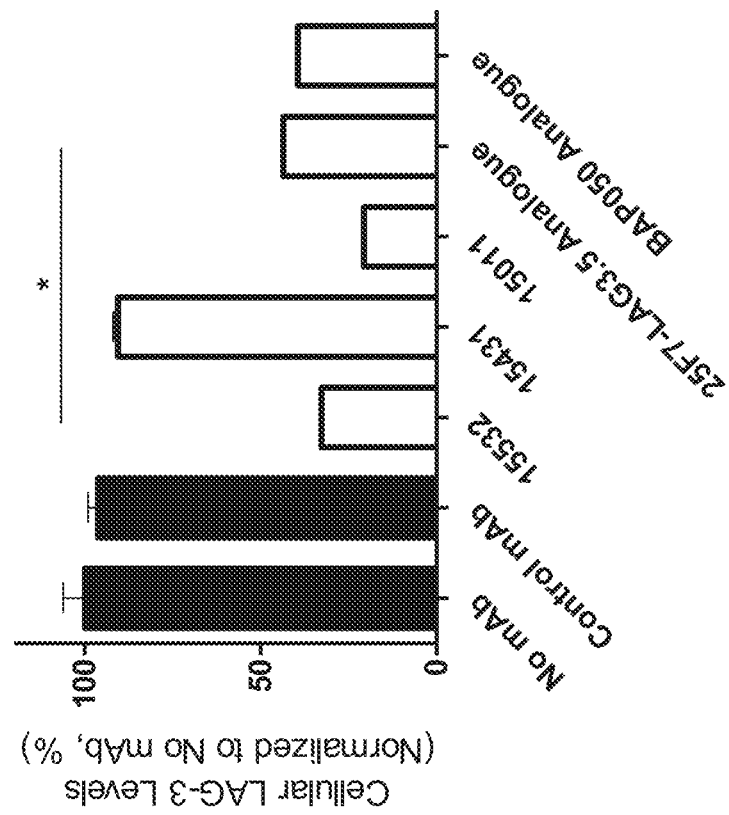

Jurkat cells expressing a modified TCR and LAG-3 (Promega) were incubated with 25 mg/mL of monoclonal antibodies as indicated in FIG. 5. After 24 hours in a humidified incubator at 37° C., supernatants were collected and cell-lysed. Levels of LAG-3 in cells were evaluated with an anti-LAG-3 detection antibody (Novus Biologicals) and simple Western technique (Sally Sue, Proteinsimple). Levels of LAG-3 in the supernatant were evaluated using an anti-LAG-3 ELISA (R&D Systems). Binding competition studies confirmed that the tested anti-LAG-3 antibodies do not compete with the ELISA detection antibody for binding to soluble LAG-3. Statistical analysis was performed using one-way ANOVA with correction for multiple comparisons followed by a Bonferroni corrected, post-hoc t-test.

The levels of cellular and soluble LAG-3 after treatment with the anti-LAG-3 mAbs 15431, 15532, 15011, 25F7-Lag3.5 analogue or BAP050 analogue are shown in FIG. 5. 15532, 15011, 25F7-Lag3.5 analogue and BAP050 analogue decreased cellular as well as soluble LAG-3 levels. 15532 decreased cellular LAG-3 levels to a lower level than 25F7-Lag3.5 analogue with statistical significance, and decreased soluble LAG-3 levels to a lower level than 25F7-Lag3.5 analogue and BAP050 analogue with statistical significance. 15431 did not lower either cellular or soluble LAG-3 levels.

Figure 6:
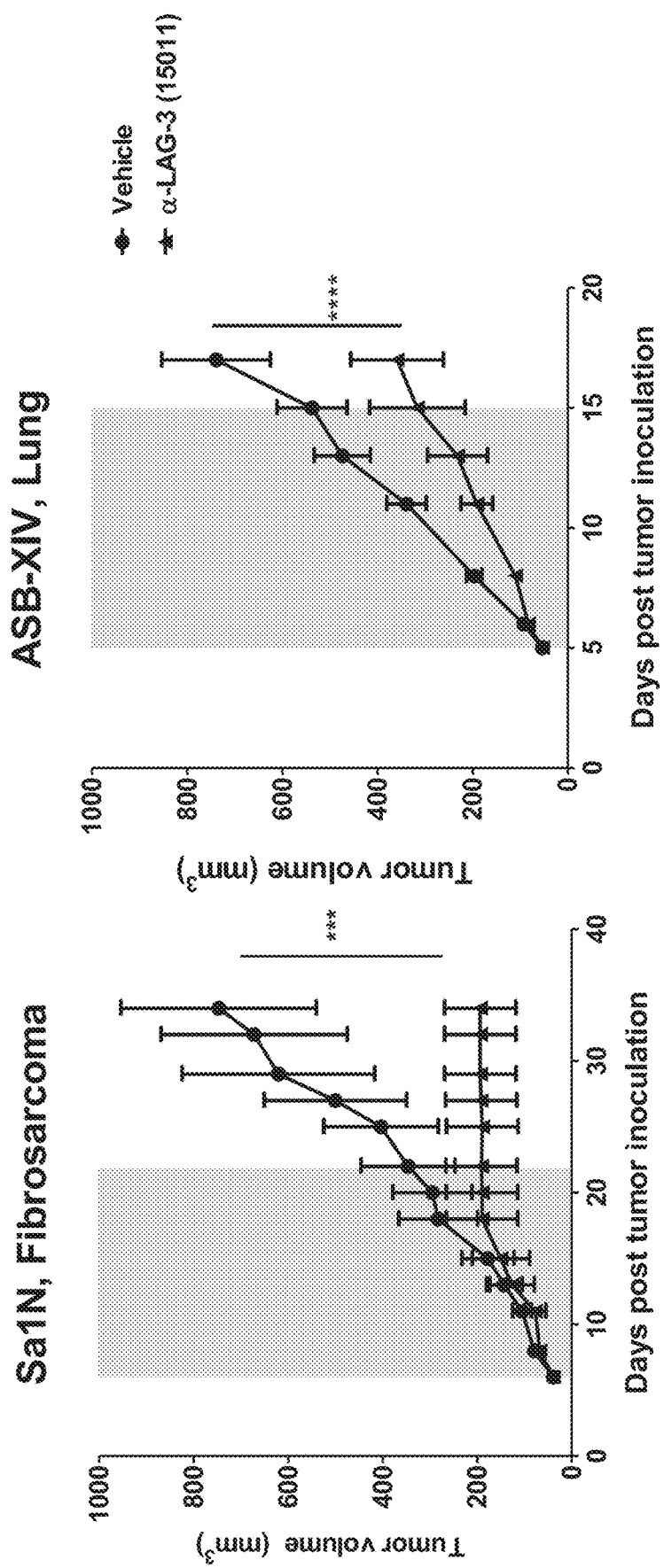
FIG. 6 demonstrates the in vivo efficacy of antibody 15011 in two syngeneic murine tumor models.

Example 10: In Vivo Efficacy of Antibody 15011 in Two Syngeneic Murine Tumor Models This example demonstrates the in vivo efficacy of antibody 15011 in two syngeneic murine tumor models.
Methods $2\times10^5$ Sa1N (fibrosarcoma) and $5\times10^6$ ASB-XIV (lung carcinoma) cells were inoculated subcutaneously into the flank of 6-8 week old female A/J (Sa1N) or BALB/cAnNRj (ASB-XIV) mice. Tumors were measured three times weekly by caliper in two dimensions and tumor volume in mm$^3$ was calculated according to the formula: (width)$^2\times$length$\times0.5$. On day 5-7 post-inoculation, at an average tumor size of 30-50 mm$^3$, the mice were randomized into two groups of ten animals and treatment initiated. The mice were treated three times weekly with a total of six treatments by intraperitoneal injection of vehicle buffer or the monoclonal antibody 15011 followed by an observation period. The antibody treatments were dosed at 10 mg/kg. Two-way ANOVA with Bonferroni's multiple comparisons test was applied to compare tumor volumes at each time-point between treatment groups. Statistical analyses were performed using GraphPad Prism version 5.0 (GraphPad Software, Inc.).
Results The results showed a profound tumor inhibitory effect of antibody 15011 in the tested syngeneic tumor models (*P<0.001) (FIG. 6). 15011 induced tumor growth regression in 50% of the mice engrafted with Sa1N tumors and resulted in tumor growth delay in the ASB-XIV syngeneic tumor model.

Figure 7:
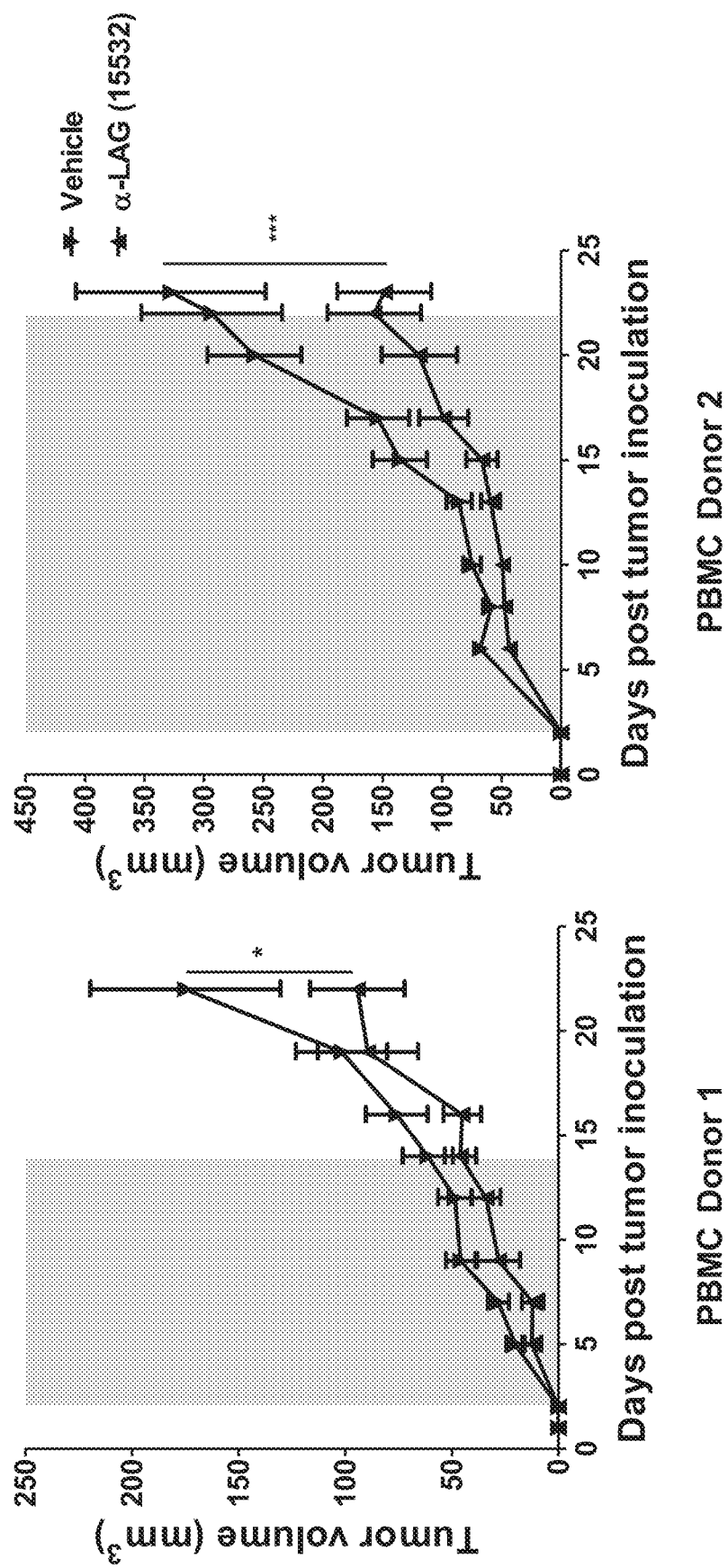
FIG. 7 demonstrates the in vivo efficacy of antibody 15532 in a semi-humanized xenograft tumor model, where the immune system in NOG mice was reconstituted with human PBMC and the mice engrafted with human melanoma A375 cells.

Example 11: In Vivo Efficacy of Antibody 15532 in NOG Mice Reconstituted with Human PBMC and Engrafted with Human Melanoma A375 Cells This example demonstrates the in vivo efficacy of antibody 15532 in a semi-humanized xenograft tumor model, where the immune system in NOG mice was reconstituted with human PBMC and the mice engrafted with human melanoma A375 cells.
Methods On study day 0, NOG mice were subcutaneously injected with $2\text{-}4.5\times10^6$ A375 melanoma cell and received 9 or $12\times10^6$ PBMCs intraperitoneally on study day 2. PBMCs from one donor were used in each experiment. Treatment was initiated at the day of PBMC inoculation and the mice were treated three times weekly with a total of six or nine treatments by intraperitoneal injection of vehicle buffer, or the monoclonal antibody 15532 (10 mg/kg), followed by an observation period. Tumors were measured three times weekly by caliper in two dimensions and tumor volume in mm$^3$ was calculated according to the formula: (width)$^2\times$ length$\times0.5$. Two-way ANOVA with Bonferroni's multiple comparisons test was applied to compare tumor volumes at each time-point between treatment groups. Statistical analyses were performed using GraphPad Prism version 5.0 (GraphPad Software, Inc.).
Results FIG. 7 shows results from two experiments using two different human PBMC donors that responded to anti-LAG-3 treatment. Treatment with 15532 resulted in significant tumor growth delay compared to the vehicle treated group [P<0.05 (donor 1) and P<0.001 (donor 2)].

Example 12: Measurement of Anti-LAG-3 Monoclonal Antibody Affinities Towards Human, Cynomolgus and Mouse LAG-3

This example demonstrates the binding of anti-LAG-3 antibodies towards human, cynomolgus and mouse LAG-3 extracellular domains as measured by Surface Plasmon Resonance (SPR). The protein sequence of human LAG-3 is available under UniProt Accession No. P18627 (SEQ ID NO: 68). The protein sequence of cynomolgus LAG-3 is available under NCBI Accession No. XP_005570011.1 (SEQ ID NO: 69). The protein sequence of mouse LAG-3 is available under UniProt Accession No. Q61790 (SEQ ID NO: 72).
Materials and Methods The kinetic binding analysis was performed by Surface Plasmon Resonance (SPR), using a Continuous Flow Microspotter (CFM, Wasatch Microfluidics, Salt Lake City, US) combined with an IBIS MX96 SPR instrument (IBIS Technologies, The Netherlands).

Anti-LAG-3 Fab antibodies were generated by digesting IgG$_1$ antibodies with GingisKHAN enzyme, using a kit provided by Genovis (Sweden).

The LAG-3 cDNAs coding for the extracellular domains of human and cynomolgus LAG-3 were synthesized and each cloned into a vector containing a CMV promoter and a human IgG₁ Fc sequence (AA P101-K330), resulting in fusion of IgG$_1$ Fc C-terminally to the cloned LAG-3 ECD. The LAG-3 Fc fusion constructs were generated by standard PCR and engineering techniques and protein was expressed transiently in 2 mL culture using an ExpiCHO™ expression system. The human LAG-3 Fc fusion constructs were harvested after 9 days and supernatants were tested for binding affinity to LAG-3 Fab antibodies by SPR. Antigens were purified using standard procedures and captured onto an G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye® was positioned in the IBIS MX96 biosensor and remaining capture sites blocked. Kinetic analysis was performed by applying a so called kinetic titration series (Karlsson R. 2006), where monomeric Fab fragments of the antibodies of the invention were injected in increasing concentrations from 1 nM to 1000 nM without application of surface regeneration steps after each Fab injection. Fab association was performed for 15 minutes and antigen dissociation was performed for 15 minutes. The recorded binding responses were fitted to a simple Langmuir 1:1 binding model with Scrubber 2 software for calculation of the on-rate (kon or ka), off-rate (koff or kd) and affinity ($K_D$) constants.

Results

The results of the affinity measurement demonstrate that the evaluated antibodies 15532, 15431, 15572, 15011 and reference antibody analogue 25F7-Lag3.5 bind human and cynomolgus LAG-3 with different affinities. 15011 is the only antibody with mouse LAG-3 cross-reactivity. The detailed binding kinetics are tabulated in Table 3 below.

TABLE 3

Binding kinetics of anti-LAG-3 Fab fragments to human, cynomolgus and mouse LAG-3 ECD as measured by SPR.

| Antibody | LAG-3 ECD | $k_{on}$ (M$^{-1}$S$^{-1}$) | $k_{off}$ (s$^{-1}$) | $K_D$ (M) |
|---|---|---|---|---|
| 15532 | Human | 1.1E+05 | 6.5E−04 | 5.8E−09 |
| 15532 | Cynomolgus | 7.1E+04 | 4.8E−03 | 6.8E−08 |
| 15532 | Mouse | N.B. | N.B. | N.B. |
| 15431 | Human | 6.6E+04 | 2.0E−03 | 3.0E−08 |
| 15431 | Cynomolgus | 5.9E+04 | 6.8E−03 | 1.2E−07 |
| 15431 | Mouse | N.B. | N.B. | N.B. |
| 15572 | Human | 1.1E+05 | 3.0E−03 | 2.7E−08 |
| 15572 | Cynomolgus | 4.0E+04 | 4.0E−03 | 1.0E−07 |
| 15572 | Mouse | N.B. | N.B. | N.B. |
| 15011 | Human | 1.1E+05 | 4.8E−04 | 4.3E−09 |
| 15011 | Cynomolgus | 7.0E+04 | 2.5E−03 | 3.5E−08 |
| 15011 | Mouse | 7.2E+04 | 2.3E−03 | 3.3E−08 |
| 25F7-Lag3.5 | Human | 1.4E+05 | 1.2E−03 | 8.5E−09 |
| 25F7-Lag3.5 | Cynomolgus | 4.2E+03 | 3.8E−03 | 9.1E−07 |
| 25F7-Lag3.5 | Mouse | N.B. | N.B. | N.B. |

*NB: No binding

Example 13: Epitope Binning of Anti-LAG-3 Antibodies

This example illustrates how the anti-LAG-3 antibodies were grouped into epitope bins based on paired competition patterns in a sandwich assay. Antibodies belonging to different epitope bins recognize different epitopes on the LAG-3 ECD.

Materials and Methods

Investigation of paired antibody competition was performed by Surface Plasmon Resonance (SPR) analysis using a Continuous Flow Microspotter (CFM) (Wasatch Microfluidics, US) combined with an IBIS MX96 SPR instrument (IBIS Technologies, The Netherlands). Surface Plasmon Resonance imaging analysis was performed on a goat-anti-human-IgG Fc SensEye® SPR sensor (Ssens BV, The Netherlands). A total of thirteen anti-LAG-3 antibodies, including reference antibody 25F7-Lag3.5, were diluted to 7.5 µg/mL in PBS buffer containing 0.05% Tween 20 (PBS-T), pH 7.0. Antibodies were captured onto the anti-Fc sensor surface by spotting for 15 minutes using a Continuous Flow Microspotter. After spotting, the SensEye® was positioned in the IBIS MX96 biosensor and residual anti-Fc sites blocked by injection of 30 µg/mL non-specific human IgG$_1$. Captured antibodies were conjugated to the surface using a FixIt kit (Ssens BV, The Netherlands). After sensor preparation, the immobilized antibodies (ligands) were used to capture monovalent LAG-3 antigen (50 nM, Acro Biosystems, China) in solution when injected over the sensor. Next, the panel of LAG-3 antibodies, diluted to 15 µg/mL in PBS-T buffer, were injected as analytes one by one over the sensor and tested for binding to captured LAG-3 in a sandwich assay to establish antibody competition patterns. After each antibody injection, the sensor surface was regenerated with 100 mM H$_3$PO$_4$ buffer, pH 3.0.

Results

Figure 8:
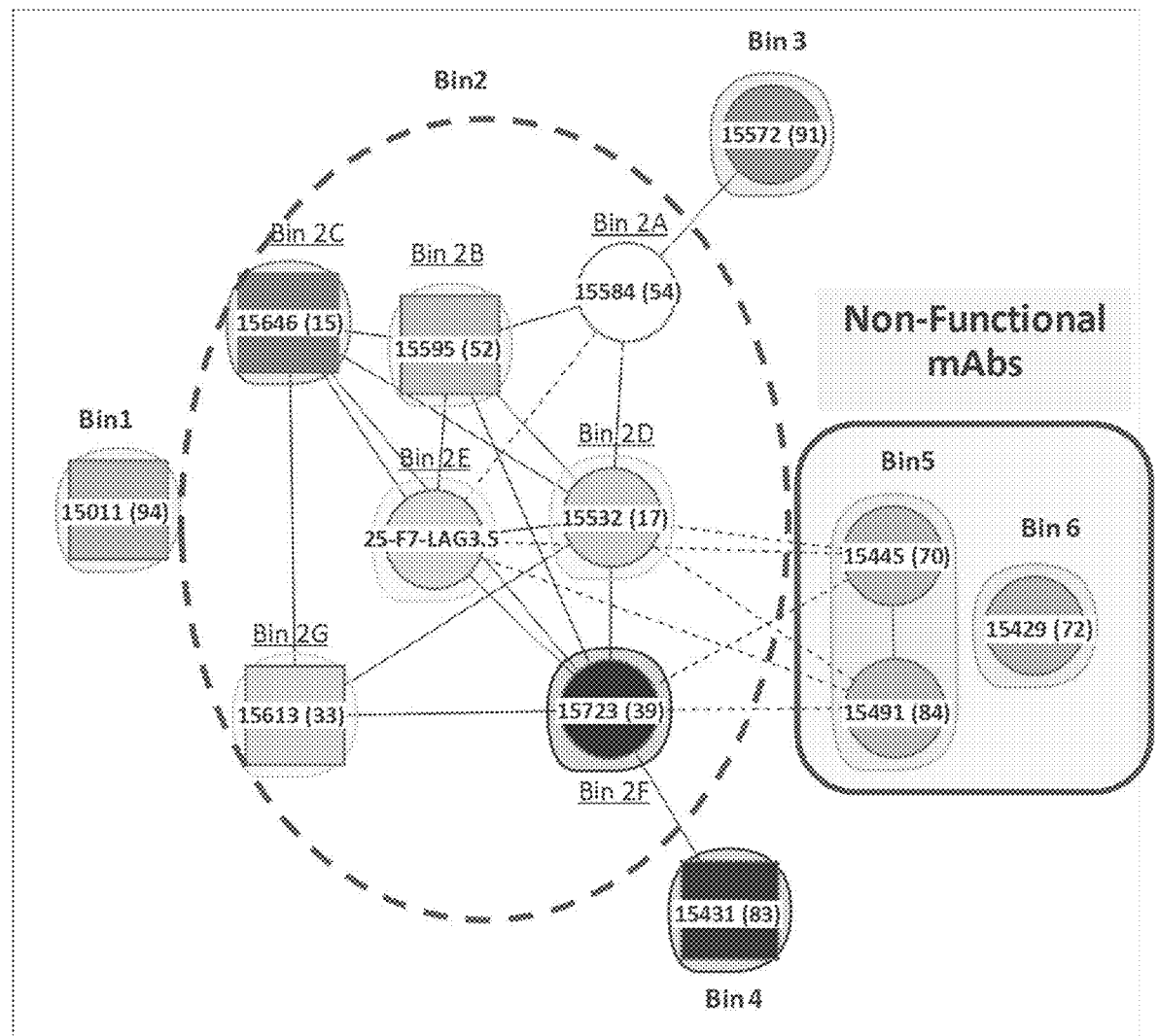
FIG. 8 shows an overview of the epitope groups (epitope bins) identified by binding competition analysis of a panel of thirteen anti-LAG-3 antibodies. Antibodies connected by black lines indicate cross blocking activity in both orientations (ligand and analyte). Antibodies connected by dashed lines indicate unidirectional blocking where the antibody is blocked when tested as an analyte only. Antibodies are grouped according to competition patterns with other anti-LAG-3 antibodies.

The competition pattern of the thirteen anti-LAG-3 antibodies is presented in FIG. 8. Antibodies are named according to their ID number and cluster group is listed in parenthesis. MAbs from identical cluster groups are expected to bind identical epitope bins, since the protein sequences from cluster members are highly related and only differ at few positions.

All antibodies were successfully epitope binned, however, antibodies 15595 (52), 15613 (33) and 15431 (38) did not work when used as ligands, and could only be tested as analytes. Antibodies 15646 (15) and 15011 (94) were only tested as ligands.

The competition analysis indicated that the panel of LAG-3 antibodies covers 6 major epitope bins (FIG. 8). Antibody 15011 (94) bound to a unique epitope that was not cross blocked by any other antibodies from the panel, and this antibody was consequently assigned to epitope bin 1. Epitope bin 2 contains seven antibodies that cross competed with some of the other mAbs from the group, and these antibodies were further divided into sub bins. MAb 15584 (54) was characterized by cross blocking both 15532 (17) and 15595 (52) when tested as a ligand or analyte, but it was not blocked by reference mAb 25F7-Lag3.5 when tested as an analyte. MAb 15613 (33) was only tested as an analyte and was shown to be blocked by 15723 (39), 15532 (17) and 15646 (15) but not 25F7-Lag3.5. Consequently, although 15532 (17) bound an epitope overlapping with 25F7-Lag3.5, the epitope of 15532 (17) is different from that of 25F7-Lag3.5 due to differences in competition with 15584 (84) and 15613 (33), and these antibodies were consequently assigned to different sub bins. Likewise, other mAbs in epitope bin 2 were assigned to sub bins based on competition patterns with other antibodies in bin 2 (FIG. 8).

MAb 15572 (91) was only found to cross compete with mAb 15584 (54) and was assigned to a separate bin 3. Likewise, mAb 15431 (83) was assigned to a separate bin 4, because this antibody only cross competed with mAb 15723 (39). Finally, two separate epitope bins containing antibodies with nonfunctional activity were identified. Epitope bin 5 contained cross blocking antibodies 15445 (70) and 15491

Figure 9:
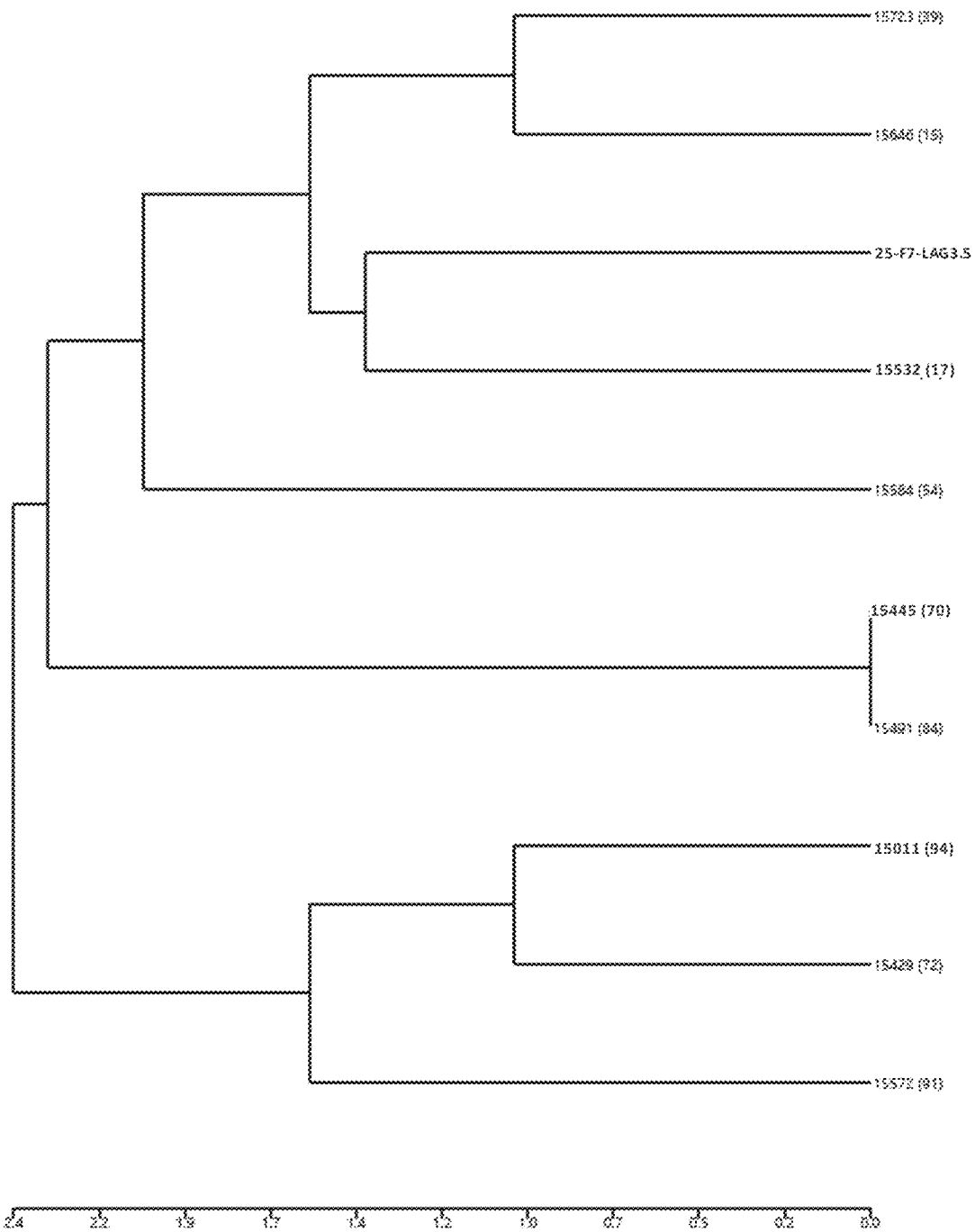
FIG. 9 shows a cluster analysis of the epitope diversity of ligand antibodies. Antibodies with branching points at x-axis values above 0 have epitopes that are distinct based on the competition for LAG-3 binding of other antibodies in the panel.

(84) and epitope bin 6 contained mAb 15429 (72) that did not cross block any of the antibodies from the panel. Bin 5 antibodies also blocked antibodies 25F7-Lag3.5, 15532 (17) and 15723 (39) from bin 2, when these were tested as analytes (FIG. 8). A summary of the competition patterns for ligand antibodies is shown in FIG. 9, where the epitope relatedness of mAbs is shown based on clustering using Euclidean distance. From the cluster diagram it can be observed that antibodies with branching points at x-axis values above zero have different epitopes compared to other antibodies in the tested LAG-3 panel. MAbs 15595 (52), 15613 (33) and 15431 (38) were not included in the cluster analysis, because they did not work as ligands.

Example 14: Epitope Mapping of LAG-3 Antibodies by LAG-3 Mutagenesis

Antibody epitopes can generally be characterized as linear epitopes (also termed continuous epitopes) or conformational epitopes (also termed discontinuous epitopes). While linear epitopes are defined based on a single continuous amino acid sequence, conformational epitopes may consist of many smaller discontinuous linear sequences or single contact residues. A collection of contact residues that cluster at the intermolecular protein interface between the antibody and the antigen is also termed a hot spot (Moreira et al., *Proteins* 68(4):803-12 (2007)). It is now widely acknowledged that most B-cell epitopes are discontinuous in nature (Sivalingam and Shepherd, *Mol Immunol.* 51(3-4):304-92012 (2012), Kringelum et al., *Mol Immunol.* 53(1-2):24-34 (2013)) with the average epitope spanning 15-22 amino acid residues of which 2-5 amino acids contribute to most of the binding (Sivalingam and Shepherd, supra).

By ranking binding affinity to 108 different LAG-3 mutants, this example illustrates how the binding epitopes of the anti-LAG-3 antibodies 15532, 15431, 15572, and 15011 can be divided into linear epitopes and hotspots that are distinct from the epitope recognized by the reference antibody 25F7-Lag3.5 analogue.

Methods

Human LAG-3 receptor (CD223) is a 525 amino acid (AA) transmembrane protein that comprises an extracellular domain (ECD) of 427 amino acids (residues 23-450) followed by a transmembrane domain (residues 451-471) and a cytoplasmic domain (residues 472-525). LAG-3 ECD contains 4 immunoglobulin domains (D1-D4) where the first domain, an IgV-type domain, is involved in ligand binding (MHCII binding) and the remaining three domains are IgC2 type domains. The first two N-terminal domains alone (D1-D2) are sufficient for ligand binding, and D2 has been shown to be required for correct receptor presentation (Huard et al., *Proc Natl Acad Sci USA* 94:5744-5749 (1997), Andrews et al., *Immunol Rev.* 276(1):80-96 (2017)). Domain 1 contains an additional unique stretch of 30 amino acids (extra loop) that is not found in other IgV-domains and that has been shown to be essential for ligand binding. Amino acids (AA) 99, 110, 125, 131 and 137 have also been identified as important for ligand binding (Y77, R88, R103, D109, R115 in the mature protein) (Huard et al, supra; Andrews et al., supra). There is no published structure for LAG-3. However, sequence and evolutionary homology between LAG-3 and CD4 have been identified, thus allowing access to structural information on LAG-3 based on homology modeling of CD4 (Huard et al., supra; Andrews et al., supra).

The protein sequences of human LAG-3 and orthologues were downloaded from UniProt or NCBI: human (P18627; SEQ ID NO: 68), cynomolgus monkey (*Macaca fascicularis*, XP_005570011.1; SEQ ID NO: 69), rat (*Rattus norvegicus*, Q5BK54; SEQ ID NO: 70) and dog (*Canis Lupus Familiaris*, F1P7Z3; SEQ ID NO: 71). The sequence identities of the different LAG-3 extracellular domain amino acid sequences are shown in Table 4 below.

TABLE 4

List of amino acid differences and sequence identity to human LAG-3 in the extracellular domain of LAG-3 from different species.

|  | Amino Acid Differences | % Sequence Identity |
|---|---|---|
| Cynomolgus LAG-3 ECD | 34 | 92.1 |
| Rat LAG-3 ECD | 140 | 67.3 |
| Dog LAG-3 ECD | 197 | 54.1 |

To map linear epitopes in the context of the native human LAG-3 structure, 35 chimeric proteins were designed, where 10 amino acids in the human LAG-3 ECD sequence were sequentially exchanged to rat sequence in segments that overlapped by 5 amino acids, and supplemented with dog and cynomolgus versions in regions of particular interest (e.g. critical AA insertion sequences and loop stretches). Sequence exchanges were performed in domain 1 of human LAG-3 spanning amino acids 23-170. From a constructed homology model based on CD4 crystal structures (1WIO, 1WIQ) and amino acid sequence alignments, surface exposed amino acids were identified and 80 individual substitutions were designed on human LAG-3 domain 1. Introduced point mutations were primarily alanine substitutions. When the surface exposed residue was alanine, this position was changed to serine.

LAG-3 cDNA coding for domains 1 and 2 of the human LAG-3 extracellular domain (AA 1-266) was gene synthesized and cloned into a vector containing CMV promoter and human IgG$_1$ Fc sequence (AA P101-K330), resulting in expression of a LAG domain 1-2 Fc fusion protein. The mutated human LAG-3 Fc fusion constructs were generated by standard PCR and engineering techniques and protein was expressed transiently in 2 ml culture using an ExpiCHO™ expression system. The human LAG-3 Fc fusion constructs were harvested, purified and tested for binding affinity to anti-LAG-3 mAbs by Surface Plasmon Resonance (SPR). The LAG-3 fusion proteins were immobilized onto a G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye® was positioned in an IBIS MX96 biosensor and captured proteins were evaluated for binding affinity. Kinetic analysis was performed by applying a so called kinetic titration series (Karlsson R. 2006), where monomeric Fab fragments of the antibodies of the invention were injected in increasing concentrations from 0.4 nM to 300 nM without application of surface regeneration steps after each Fab injection. Fab association was performed for 15 minutes and antigen dissociation was performed for 15 minutes. The recorded binding responses were fitted to a simple Langmuir 1:1 binding model with Scrubber 2 software for calculation of the on-rate (kon or ka), off-rate (koff or kd) and affinity (KD) constants.

Results

The binding affinities of Fab fragments of anti-LAG-3 antibodies 15532, 15431, 15572, 15011 and the reference antibody 25F7-Lag3.5 analogue were evaluated with respect to altered binding to LAG-3 mutant constructs. The binding affinities of Fab fragments binding to the mutated LAG-3 constructs were expressed as the ratio between KD mutant/ KD wildtype (normalized binding affinity). Tables 5 and 6 below show the normalized binding affinities to all tested chimeric proteins and for the alanine scanning experiments, respectively. A cut-off of at least 5-fold affinity reduction was employed as a criterion for detecting significantly reduced binding affinity to mutated LAG-3 constructs. In some instances, no binding could be detected to specific antibodies. These constructs are listed as not binding (N.B.).

The analysis showed that the binding epitopes of anti-LAG-3 antibodies 15532, 15431, 15572, 15011 are distinct from that of the reference antibody 25F7-Lag3.5 analogue. The binding epitope of 15532 was evident from the chimeric proteins with AA inserted at positions 78-87, 84-92, 88-97—a collective amino acid stretch in LAG-3 that is within the domain 1 extra loop. However, unlike 25F7-Lag3.5, the linear epitopes of 15532 extend beyond this stretch, including AA 95-100, AA 98-105 and AA123-131. Interestingly, key amino acids for ligand interactions have been identified in the segment from 99-131 (Y99, R125 & D131; Huard et al, supra). The 25F7-Lag3.5 analogue did not show any sensitivity for mutations in the region critical for ligand binding. The 15532 contact residues as measured by alanine substitutions were identified as H85, P86, A87, P89, S91, W92 and G93 whereas the 25F7-Lag3.5 analogue did not show sensitivity towards P86 and S91, illustrating differentiated contact residues within the AA 85-93 region. 15532 was able to bind chimeric construct #28 with cynomolgus AA backmutations (P84H; H85R; S90Y), whereas the 25F7-Lag3.5 analogue was not, again reflecting a differentiated fine epitope within the AA 84-90 region.

The two antibodies 15431 and 15572 were both found to bind linear epitopes at segments AA 23-30 and 40-66. Further alanine scanning illustrated that both antibodies shared identical contact residues at positions A40, Q41, P43, P46, P49, D52, T62, Q64, H65, Q66, P67 and D68. 15431 was additionally sensitive to chimeric constructs 88-97, 95-100 and 98-105 (segment AA 88-105). The AA region 98-105 proved to be a unique shared epitope between 15532, 15431, 15572 and 15011. The 25F7-Lag3.5 analogue did not bind this epitope. Alanine scanning indicated that 15431 and 15572 shared contact residues P96, Y99, T100, V101, P106 and G107, while 15431 had unique contacts at positions G93, P94, and R98. The antibody 15431 also had a linear epitope in segments AA 123-131, 128-137 and 148-154. Interestingly, positions 125, 131 and 137 have previously been shown to be important for ligand binding (Huard et al, supra). These segments (AA 123-131, 128-137 and 148-154) were also important for 15572, which recognized linear epitopes in the segments AA 118-137 and 148-161. Alanine scanning further showed that both 15431 and 15572 shared contact residues at positions R119, E124, R129, G130, D131, S133, R137, P138, D143, R148 and R163 while the 25F7-Lag3.5 analogue did not show sensitivity towards any of these epitope regions or amino acid positions.

Antibody 15011 contained a linear epitope defined by a chimeric construct with mutations in the range from AA 98-105, and alanine scanning further extended the unique epitope to include contact residues at positions G107, L109, R110 and S111. Interestingly, R110 has been shown to be important for ligand binding (Huard et al, supra). The amino acid sequence is well conserved in this region (AA 98-113) between human, cynomolgus, mouse and rat orthologues, explaining the cross-reactivity of this antibody to mouse and cynomolgus monkey LAG-3 (Example 12). A summary of the collected epitope mapping findings is shown in Table 7 below.

In summary, we have shown at single amino acid resolution, by analyzing binding to a panel of 108 LAG-3 mutants, that the four antibodies 15532, 15431, 15572 and 15011 recognize unique but partially overlapping epitopes in domain 1 of LAG-3. This finding is consistent with the epitope binning analysis of Example 13, showing that 15532 cross-competes with the 25F7-Lag3.5 analogue, but has a differentiated competition pattern with other LAG-3 antibodies and hence a different epitope (Table 7). 15431, 15572 and 15011 did not compete for binding with 15532 or 25F7-Lag3.5 and had unique competition patterns with discrete epitope bin 2 antibodies. The assigned epitope bins (Example 13) match well the epitope mapping that revealed that each antibody showed unique differentiated epitopes (Table 7). The epitope data including chimeric construct #28 also corroborated well with the binding affinity analysis (Example 12) in which 15532 showed significant binding to cynomolgus LAG-3 and 25F7-Lag3.5 did not—reflecting different properties of the antibodies due to differentiated contact residues.

TABLE 5

Summary of binding affinity analysis for Fab fragments of anti-LAG-3 antibodies binding mutated LAG-3 ECD constructs with inserted rat, dog or cynomolgus sequence segments. Normalized binding expressed as $K_D$ mutant/$K_D$ wild type.

| Chimeric construct # | Scanned region hu LAG-3 | Mutated region hu LAG-3 | Introduced mutations from other species | 15532 | 15431 | 15572 | 15011 | 25F7-Lag3.5 analogue |
|---|---|---|---|---|---|---|---|---|
| 1 | AA 23-32 | AA 23-30 | L23S; Q24G; A27K; V29L; P30S | 3.2 | N.B. | N.B. | 0.5 | 1.3 |
| 2 | AA 28-37 | AA 29-30 | V29L; P30S | 3.1 | N.B. | N.B. | 0.5 | 1.2 |
| 3 | AA 33-42 | AA 40-41 | A40V; Q41H | 2.2 | N.B. | N.B. | 0.5 | 1.3 |
| 4 | AA 38-47 | AA 40-47 | A40V; Q41H; P46L; T47E | 3.9 | N.B. | N.B. | 0.5 | 1.3 |
| 5 | AA 43-52 | AA 46-51 | P46L; T47E; I48F; L50H; Q51L | 2.7 | N.B. | N.B. | 0.5 | 1.3 |
| 6 | AA 48-57 | AA 48-55 | I48F; L50H; Q51L; L53P; S54N; L55F | 3.4 | N.B. | N.B. | 0.5 | 1.4 |
| 7 | AA 53-62 | AA 53-60 | L53P; S54N; L55F; A59G; G60W | 3.4 | N.B. | N.B. | 0.5 | 1.4 |
| 8 | AA 58-67 | AA 59-66 | A59G; G60W; Q66R | 2.7 | N.B. | N.B. | 0.5 | 1.3 |
| 9 | AA 63-72 | AA 66-71 | Q66R; G70D; P71Q | 3.9 | 0.4 | 1.1 | 0.7 | 1.3 |
| 10 | AA 68-77 | AA 70-77 | G70D; Q71Q; A74S; A75I; G77A | 1.1 | 1.1 | 0.7 | 1.8 | 1.0 |
| 11 | AA 73-82 | AA 74-82 | A74S; A75I; G77A; H78L; P79D; A81L; P82Q | 1.5 | 0.4 | 0.5 | 0.6 | 1.1 |
| 12 | AA 78-87 | AA 78-87 | H78L; P79D; A81L; P82Q; delP84-A87 | N.B. | 0.8 | 0.8 | 0.9 | N.B. |
| 13 | AA 83-92 | AA 84-92 | delP84-A87; A88M; S91T; W92R | N.B. | 0.6 | 1.1 | 1.3 | N.B. |
| 14 | AA 88-97 | AA 88-97 | A88M; S91T; W92R; G93R; P94H; R95P; R97H | N.B. | N.B. | 0.7 | 0.6 | N.B. |
| 15 | AA 93-102 | AA 95-100 | R95G; R98S; T100V | 6.5 | N.B. | 3.1 | 1.9 | 1.5 |

TABLE 5-continued Summary of binding affinity analysis for Fab fragments of anti-LAG-3 antibodies binding mutated LAG-3 ECD constructs with inserted rat, dog or cynomolgus sequence segments. Normalized binding expressed as $K_D$ mutant/$K_D$ wild type.

| Chimeric construct # | Scanned region hu LAG-3 |

TABLE 6-continued

Summary of binding affinity analysis for Fab fragments of anti-LAG-3 antibodies binding point mutation scanned human LAG-3. Normalized binding expressed as $K_D$ mutant/$K_D$ wild type.

| Point mutation # | Mutated AA in hu LAG-3 | 15532 | 15431 | 15572 | 15011 | 25F7-Lag3.5 analogue |
|---|---|---|---|---|---|---|
| 55 | S111A | 1.0 | 0.8 | 0.7 | 53.4 | 0.9 |
| 56 | G112A | 1.0 | 0.5 | 0.5 | 3.1 | 0.9 |
| 57 | R113A | 0.6 | 0.9 | 0.7 | 3.3 | 0.8 |
| 58 | P115A | 1.0 | 1.1 | 1.4 | 1.3 | 1.0 |
| 59 | Q117A | 0.8 | 0.4 | 0.5 | 0.7 | 0.8 |
| 60 | P118A | 0.7 | 1.0 | 0.9 | 1.2 | 0.8 |
| 61 | R119A | 3.2 | N.B. | N.B. | 0.6 | 1.1 |
| 62 | Q121A | 0.9 | 1.0 | 0.6 | 0.9 | 0.9 |
| 63 | D123A | 1.0 | 0.9 | 0.5 | 0.8 | 1.0 |
| 64 | E124A | 1.8 | N.B. | N.B. | 0.8 | 1.1 |
| 65 | R125A | 0.9 | 1.1 | 1.1 | 1.1 | 0.9 |
| 66 | G126A | 0.9 | 0.9 | 0.9 | 0.9 | 0.9 |
| 67 | R127A | 0.6 | 0.9 | 0.5 | 0.9 | 0.7 |
| 68 | Q128A | 0.7 | 0.8 | 0.9 | 1.0 | 0.7 |
| 69 | R129A | 3.0 | N.B. | N.B. | 0.7 | 1.2 |
| 70 | G130A | 4.4 | N.B. | N.B. | 0.6 | 1.3 |
| 71 | D131A | 4.2 | N.B. | N.B. | 0.6 | 1.2 |
| 72 | S133A | 2.2 | N.B. | N.B. | 0.6 | 1.1 |
| 73 | R137A | 3.6 | N.B. | N.B. | 0.6 | 1.0 |
| 74 | P138A | 2.7 | N.B. | N.B. | 0.7 | 1.0 |
| 75 | R141A | 0.7 | 1.0 | 0.9 | 1.1 | 0.8 |
| 76 | D143A | 3.8 | N.B. | N.B. | 0.5 | 1.0 |
| 77 | R148A | 2.9 | N.B. | N.B. | 0.7 | 1.2 |
| 78 | R154A | 0.8 | 1.0 | 0.8 | 1.2 | 0.8 |
| 79 | S159A | 0.7 | 0.9 | 0.3 | 0.7 | 0.8 |
| 80 | R163A | 2.5 | N.B. | N.B. | 0.6 | 1.0 | bold <5-fold KD change Point mutants
N.B. >5-fold KD change Point mutants
No binding of Point mutants

TABLE 7

Summary of the binding epitopes identified for tested anti-LAG-3 antibodies

| Antibody | Epitope Bin | Linear epitopes | Contact Residues |
|---|---|---|---|
| 15532 | 2D | 78-105 | H85, P86, A87, P89, S91, W92, G93 |
|  |  | 123-131 |  |
| 15431 | 4 | 23-30 | A40, Q41, P43, P46, P49, D52 |
|  |  | 40-66 | T62, Q64, H65, Q66, P67, D68 |
|  |  | 88-105 | G93, P94, P96, R98, Y99, T100, V101, P106, G107 |
|  |  | 123-137 | R119, E124 |
|  |  | 148-152 | R129, G130, D131, S133, R137, P138, D143, R148, R163 |
| 15572 | 3 | 23-30 | A40, Q41, P43, P46, P49, D52 |
|  |  | 40-66 | T62, Q64, H65, Q66, P67, D68 |
|  |  | 98-105 | P96, Y99, T100, V101, P106, G107 |
|  |  | 118-137 | R119, E124 |
|  |  | 148-161 | R129, G130, D131, S133, R137, P138, D143, R148, R163 |
| 15011 | 1 | 98-105 | G107, L109, R110, S111 |
| 25F7-Lag3.5 analogue | 2E | 78-97 | H85, A87, P89, W92, G93 |

TABLE 8

SEQ ID NOs for VH, VL, HC and LC DNA and protein sequences

| SEQ ID NO | Sequence |
|---|---|
| 1 | 15646 heavy chain variable domain (VH) DNA sequence |
| 2 | 15646 light chain variable domain (VL) DNA sequence |
| 3 | 15646 VH protein sequence |
| 4 | 15646 VL protein sequence |
| 5 | 15532 VH DNA sequence |
| 6 | 15532 VL DNA sequence |
| 7 | 15532 VH protein sequence |
| 8 | 15532 VL protein sequence |
| 9 | 15723 VH DNA sequence |
| 10 | 15723 VL DNA sequence |
| 11 | 15723 VH protein sequence |
| 12 | 15723 VL protein sequence |
| 13 | 15595 VH DNA sequence |
| 14 | 15595 VL DNA sequence |
| 15 | 15595 VH protein sequence |
| 16 | 15595 VL protein sequence |
| 17 | 15431 VH DNA sequence |
| 18 | 15431 VL DNA sequence |
| 19 | 15431 VH protein sequence |
| 20 | 15431 VL protein sequence |
| 21 | 15572 VH DNA sequence |
| 22 | 15572 VL DNA sequence |
| 23 | 15572 VH protein sequence |
| 24 | 15572 VL protein sequence |
| 25 | 15011 VH DNA sequence |
| 26 | 15011 VL DNA sequence |
| 27 | 15011 VH protein sequence |
| 28 | 15011 VL protein sequence |
| 29 | IgG$_1$-LALA heavy chain (HC) constant region DNA sequence |
| 30 | IgG$_1$-LALA heavy chain (HC) constant region protein sequence |
| 31 | Ig lambda light chain (LC) constant region DNA sequence |
| 32 | Ig lambda light chain (LC) constant region protein sequence |
| 33 | Ig kappa light chain (KC) constant region DNA sequence |
| 34 | Ig kappa light chain (KC) constant region protein sequence |

TABLE 9

SEQ ID NOs for the VH and VL DNA and protein sequences and the H-CDR1-3 and L-CDR1-3 amino acid sequences of the anti-LAG-3 antibodies

| Antibody | VH (DNA) | VL (DNA) | VH (Protein) | VL (Protein) | H-CDR1 | H-CDR2 | H-CDR3 | L-CDR1 | L-CDR2 | L-CDR3 |
|---|---|---|---|---|---|---|---|---|---|---|
| 15646 | 1 | 2 | 3 | 4 | 35 | 36 | 37 | 38 | 39 | 40 |
| 15532 | 5 | 6 | 7 | 8 | 41 | 42 | 43 | 44 | 45 | 40 |
| 15723 | 9 | 10 | 11 | 12 | 35 | 42 | 46 | 44 | 47 | 40 |
| 15595 | 13 | 14 | 15 | 16 | 48 | 49 | 50 | 51 | 47 | 52 |
| 15431 | 17 | 18 | 19 | 20 | 53 | 54 | 55 | 44 | 45 | 40 |
| 15572 | 21 | 22 | 23 | 24 | 56 | 57 | 58 | 59 | 60 | 61 |
| 15011 | 25 | 26 | 27 | 28 | 62 | 63 | 64 | 65 | 66 | 67 |

TABLE 10

Complementarity determining regions (CDRs) of anti-LAG-3 antibodies and germline gene origin of OMT rat-derived antibodies.

| Antibody number | IGHV gene | H-CDR1 | H-CDR2 | H-CDR3 | SEQ ID NOs |
|---|---|---|---|---|---|
| 15646 | IGHV4-34 | GGSFSGYY | INHRGST | CTRGEEWESLFFDYW | 35-37 |
| 15532 | IGHV4-34 | GESFSGYY | INHSGST | CARGWDLLDWNDYWNEYW | 41-43 |
| 15723 | IGHV4-34 | GGSFSGYY | INHSGST | CARGEDWGESFFDYW | 35, 42, 46 |
| 15595 | IGHV1-24 | GYSLTEIS | FDPEDGET | CATGGWGPNWFDPW | 48-50 |
| 15431 | IGHV6-1 | GDSVSSNSA | TYYRSKW | CARDDDWNDFDYW | 53-55 |
| 15572 | IGHV4-39 | GDSISSSS | YYIFYSGNT | CAREDDFLTDYYGAFDIW | 56-58 |
| 15011 | IGHV3-23* | GFDFRSYA | INGEVGGSNTCVKGAGACGICNDDIDAW | | 62-64 |

| Antibody number | IGKV gene | L-CDR1 | L-CDR2 | L-CDR3 | SEQ ID NOs |
|---|---|---|---|---|---|
| 15646 | IGKV3-11 | QSISSY | GAS | CQQRSNWPLTF | 38-40 |
| 15532 | IGKV3-11 | QSVSSY | DAS | CQQRSNWPLTF | 44, 45, 40 |
| 15723 | IGKV3-11 | QSVSSY | AAS | CQQRSNWPLTF | 44, 47, 40 |
| 15595 | IGKV1-12 | QGISSW | AAS | CQQANSFPFTF | 51, 47, 52 |
| 15431 | IGKV3-11 | QSVSSY | DAS | CQQRSNWPLTF | 44, 45, 40 |
| 15572 | IGKV1-5 | QSISSW | KAS | CQQYNSYLTF | 59-61 |
| 15011 | IGLV3-19* | GSYAGSY | DND | CGSTNDNDDGGLF | 65-67 |

*Genes used for humanization, see Example 2.

Sequence List

VH and VL DNA and protein sequences
SEQ ID NO: 1 (15646 VH DNA sequence)
CAGGTGCAGCTGCAGCAGTGGGGTGCCGGTCTGCTGAAGCCTTCTGAAACTCTGTCTCTGACTT
GTGCCGTCTATGGTGGATCATTCAGCGGCTACTATTGGTCCTGGATCAGGCAGCCCCCTGGCAA
GGGCCTGGAGTGGATCGGCGAGATCAACCACCGGGGCTCTACCAACTACAATCCCTCTCTGAAG
AGCAGGGTGACCATCTCCGTGGACACATCTAAGAATCAGTTCAGCCTGAAGCTGAGCTCCGTGA
CCGCCGCTGATACAGCCGTGTACTATTGCACAAGGGGGGAGGAATGGGAGTCACTGTTCTTTGA
TTACTGGGGGCAGGGGACACTGGTCACAGTCTCGAGT SEQ ID NO: 2 (15646 VL DNA sequence)
GAAATCGTCCTGACCCAGTCCCCCGCCACCCTGAGCCTGAGCCCCGGAGAAAGAGCCACCCTGT
CCTGCCGAGCAAGCCAGTCCATCAGCTCCTATCTCGCCTGCCAGCAGAAACCAGGCCAGGC
TCCCCGGCTGCTGATCTACGGCGCCTCCAACAGAGCTACAGGAATCCCAGCCCGCTTCAGCGGC
TCCGGCTCTGGCACAGACTTTACCCTGACAATCTCTAGCCTGGAGCCTGAGGATTTCGCCGTGT
ACTATTGCCAGCAGAGATCTAATTGGCCACTGACATTCGGCGGCGGCACACGGGTGGAGATCAA
G SEQ ID NO: 3 (15646 VH protein sequence)
QVQLQQWGAGLLKPSETLSLTCAVYGGSFSGYYWSWIRQPPGKGLEWIGEINHRGSTNYNPSLK
SRVTISVDTSKNQFSLKLSSVTAADTAVYYCTRGEEWESLFFDYWGQGTLVTVSS SEQ ID NO: 4 (15646 VL protein sequence)
EIVLTQSPATLSLSPGERATLSCRASQSISSYLAWYQQKPGQAPRLLIYGASNRATGIPARFSG
SGSGTDFTLTISSLEPEDFAVYYCQQRSNWPLTFGGGTRVEIK SEQ ID NO: 5 (15532 VH DNA sequence)
CAGGTTCAGCTGCAGCAGTGGGGCGCCGGCCTGCTGAGACCAAGCGAGACCCTGTCCCTGACAT
GCGCCGTGTATGGCGAGAGCTTCTCCGGCTATTACTGGAACTGGATCCGGCAGCCTCCCGGCAA
GGGCCTGGAGTGGATCGGCGAGATCAATCACTCCGGCTCCACCAATTACAACCCATCCCTGAAG
TCTCGGGTGACAATCAGCGTGGATACAAGCAAGACCCAGTTCAGCCTGAAGCTGAGCTCCGTGA
CAGCTGCCGATACCGCCGTGTATTACTGCGCCAGAGGCTGGGACCTGCTGGATTGGAATGACTA
CTGGAATGAGTACTGGGGCCAGGGGACCCTGGTGACCGTCTCGAGT

Sequence List

SEQ ID NO: 6 (15532 VL DNA sequence)
GAGATCGTGCTGACCCAGTCCCCTGCCACCCTGTCTCTGTCCCCTGGCGAGCGGGCCACCCTGT
CCTGTAGAGCTTCTCAGTCCGTGTCTTCCTACCTGGCTTGGTACCAGCAGAAGCCAGGACAGGC
CCCAAGACTGCTGATCTATGACGCTTCCAATCGGGCTACCGGCATCCCAGCTCGCTTTAGCGGC
TCCGGCTCCGGCACCGACTTCACCCTGACAATCAGCTCCCTGGAGCCAGAGGATTTTGCCGTGT
ATTACTGTCAGCAGAGGTCCAATTGGCCACTGACATTTGGCGGCGGCACAAAGGTTGAGATCAA
G SEQ ID NO: 7 (15532 VH protein sequence)
QVQLQQWGAGLLRPSETLSLTCAVYGESFSGYYWNWIRQPPGKGLEWIGEINHSGSTNYNPSLK
SRVTISVDTSKTQFSLKLSSVTAADTAVYYCARGWDLLDWNDYWNEYWGQGTLVTVSS SEQ ID NO: 8 (15532 VL protein sequence)
EIVLTQSPATLSLSPGERATLSCRASQSVSSYLAWYQQKPGQAPRLLIYDASNRATGIPARFSG
SGSGTDFTLTISSLEPEDFAVYYCQQRSNWPLTFGGGTKVEIK SEQ ID NO: 9 (15723 VH DNA sequence)
CAGGTTCAGCTGCAGCAGTGGGGCGCTGGCCTGCTGAAGCCCTCTGAGACCCTGTCTCTGACCT
GTGCCGTGTATGGCGGCAGCTTCTCCGGCTATTACTGGAACTGGATCCGCCAGCCCCCCGGCAA
GGGCCTGGAGTGGATCGGCGAGATCAACCACTCCGGCTCTACCAACTACAATCCTTCTCTGAAG
TCCAGGGTGACAATCAGCGTGGACACCAGCAAGAACCAGTTTAGCCTGAAGCTGTCCAGCGTGA
CAGCTGCCGATACAGCCGTGTATTACTGCGCCAGAGGCGAGGATTGGGGCGAGAGCTTCTTTGA
TTACTGGGGCCAGGGGACCCTGGTGACCGTCTCGAGT SEQ ID NO: 10 (15723 VL DNA sequence)
GAGATCGTGCTGACCCAGTCCCCTGCCACCCTGTCTCTGTCCCCTGGCGAGCGGGCCACCCTGA
GCTGTCGGGCCTCCCAGTCCGTGAGCTCCTACCTGGCTTGGTATCAGCAGAAGCCAGGACAGGC
CCCAAGACTGCTGATCTACGCCGCTTCCAATGGGCCACCGGCATCCCCGCCAGATTTTCCGGC
TCTGGCTCCGGCACCGATTTCACCCTGACAATCAGCTCCCTGGAGCCAGAGGACTTCGCCGTGT
ACTACTGCCAGCAGAGGTCTAATTGGCCACTGACATTTGGCGGCGGCACCAAGGTTGAGATCAA
G SEQ ID NO: 11 (15723 VH protein sequence)
QVQLQQWGAGLLKPSETLSLTCAVYGGSFSGYYWNWIRQPPGKGLEWIGEINHSGSTNYNPSLK
SRVTISVDTSKNQFSLKLSSVTAADTAVYYCARGEDWGESFFDYWGQGTLVTVSS SEQ ID NO: 12 (15723 VL protein sequence)
EIVLTQSPATLSLSPGERATLSCRASQSVSSYLAWYQQKPGQAPRLLIYAASNRATGIPARFSG
SGSGTDFTLTISSLEPEDFAVYYCQQRSNWPLTFGGGTKVEIK SEQ ID NO: 13 (15595 VH DNA sequence)
CAGGTTCAGCTGGTGCAGTCCGGCGCTGAGGTGAAGAAGCCTGGAGCTTCTGTGAAGGTTTCCT
GTAAGGTTTCCGGCTATAGCCTGACCGAGATCTCTATGCACTGGGTACGGCAAGCCCCCGGCAA
GGGCCTGGAGTGGATGGGCGGCTTTGACCCAGAGGATGGCGAGACCATCTACGCTCAGAGGTTT
CAGGGGCGCGTGATCATGACCGAGGATACCAGCACCGATACCGCCTACATGGAGCTGTCCAGCC
TGAGATCCGAGGATACCGCCGTGTATTACTGCGCTACTGGTGGCTGGGGCCCCAATTGGTTCGA
TCCTTGGGGCCAGGGGACCCTGGTGACCGTCTCGAGT SEQ ID NO: 14 (15595 VL DNA sequence)
GACATCCAGATGACACAGTCTCCTTCCTCTGTGAGCGCCTCTGTGGGCGACCGCGTGACCATCA
CATGCCGCGCTTCCCAGGGGATCTCTTCCTGGCTGGCTTGGTACCAGCAGAAGCCCGGCAAGGC
CCCCAAGCTGCTGATCTATGCTGCCAGCAGCCTGCAGTCCGGCGTGCCTTCCAGGTTTAGCGGC
TCCGGCTCCGGCACCGACTTTACACTGACAATCAGCTCCCTGCAGCCCGAGGATTTTGCCACCT
ATTACTGTCAGCAGGCGAATTCCTTCCCTTTTACATTCGGCCCTGGCACCAAGGTTGATATCAA
G SEQ ID NO: 15 (15595 VH protein sequence)
QVQLVQSGAEVKKPGASVKVSCKVSGYSLTEISMHWVRQAPGKGLEWMGGFDPEDGETIYAQRF
QGRVIMTEDTSTDTAYMELSSLRSEDTAVYYCATGGWGPNWFDPWGQGTLVTVSS SEQ ID NO: 16 (15595 VL protein sequence)
DIQMTQSPSSVSASVGDRVTITCRASQGISSWLAWYQQKPGKAPKLLIYAASSLQSGVPSRFSG
SGSGTDFTLTISSLQPEDFATYYCQQANSFPFTFGPGTKVDIK SEQ ID NO: 17 (15431 VH DNA sequence)
CAGGTTCAGCTGCAGCAGTCCGGCCCCGCCTGGTGAAGCCAAGCCAGACCCTGTCTCTGACAT
GCGCCATCTCCGGCGACAGCGTGTCCTCTAACTCCGCCGCTTGGAATTGGATCCGGCAGTCTCC
ATCCAGAGGCCTGGAGTGGCTGGGCAGAACCTATTACCGGTCCAAGTGGTACAACGATTATGCC
GTGTCCGTGAAGAGCAGAATCACCATCAACCCTGATACCAGCAAGAACCAGTTCAGCCTGCAGC
TGAATTCCGTGACCCCAGAGGATACAGCCGTGTATTACTGTGCTAGGACGATGATTGGAATGA
CTTCGATTACTGGGGCCAGGGGACCCTGGTGACAGTCTCGAGT SEQ ID NO: 18 (15431 VL DNA sequence)
GAGATCGTGCTGACCCAGTCCCCCAGCTACACTGTCCCTGTCTCCCGGCGAGCGGGCCACCCTGA
GCTGTAGAGCTTCCCAGTCCGTGTCTTCCTATCTGGCTTGGTATCAGCAGAAGCCAGGACAGGC
CCCAAGGCTGCTGATCTACGACGCCTCCAATAGAGCCACCGGCATCCCAGCTAGATTTTCTGGC

```
TCCGGCTCCGGCACCGATTTCACACTGACCATCTCTAGCCTGGAGCCAGAGGATTTTGCTGTAT
ATTACTGCCAGCAGCGCAGCAACTGGCCCCTGACATTTGGCGGCGGCACCAAGGTTGAGATCAA
G

SEQ ID NO: 19 (15431 VH protein sequence)
QVQLQQSGPGLVKPSQTLSLTCAISGDSVSSNSAAWNWIRQSPSRGLEWLGRTYYRSKWYNDYA
VSVKSRITINPDTSKNQFSLQLNSVTPEDTAVYYCARDDDWNDFDYWGQGTLVTVSS SEQ ID NO: 20 (15431 VL protein sequence)
EIVLTQSPATLSLSPGERATLSCRASQSVSSYLAWYQQKPGQAPRLLIYDASNRATGIPARFSG
SGSGTDFTLTISSLEPEDFAVYYCQQRSNWPLTFGGGTKVEIK SEQ ID NO: 21 (15572 VH DNA sequence)
CAGCTGCAGCTGCAGGAAAGCGGCCCCGGCCTGGTGAAGCCCTCTGAGACCCTGTCCCTGACAT
GCACCGTGAGCGGCGATTCCATCAGCTCTTCCAGCTATTACTGGGGCTGGATCCGGCAGCCCC
CGGCAAGGGCCTGGAGTGGATCGGCAGCATCTTCTACTCCGGCAATACATATTATAATCCTTCT
CTGAAGAGCAGGGTGACAATCAGCGTGGATACCTCCAAGAATCAGTTTAGCCTGAAGCTGAGCT
CCGTGACAGCTGCCGATACAGCCGTGTATTACTGCGCTAGGGAGGACGATTTTCTGACCGATTA
TTACGGCGCTTTCGACATCTGGGGCCAGGGGACAATGGTGACAGTCTCGAGT SEQ ID NO: 22 (15572 VL DNA sequence)
GATATCCAGATGACCCAGTCTCCAAGCACCCTGAGCGCCTCTGTGGGCGATCGGGTGACCATCA
CATGTCGGGCTTCTCAGTCCATCAGCAGCTGGCTGGCTTGGTATCAGCAGAAGCCCGGCAAGGC
CCCAAAGCTGCTGATCTACAAGGCCTCTTCCAGCGAGAGCGGCGTGCCATCCAGGTTTAGCGGC
TCCGGCTCCGGCACCGAGTTTACCCTGACCATCTCTTCCCTGCAGCCCGATGACTTTGCCACCT
ACTACTGTCAGCAGTACAATTCCTATCTGACATTCGGCGGCGGCACCAAGGTTGAGATCAAG SEQ ID NO: 23 (15572 VH protein sequence)
QLQLQESGPGLVKPSETLSLTCTVSGDSISSSSYYWGWIRQPPGKGLEWIGSIFYSGNTYYNPS
LKSRVTISVDTSKNQFSLKLSSVTAADTAVYYCAREDDFLTDYYGAFDIWGQGTMVTVSS SEQ ID NO: 24 (15572 VL protein sequence)
DIQMTQSPSTLSASVGDRVTITCRASQSISSWLAWYQQKPGKAPKLLIYKASSSESGVPSRFSG
SGSGTEFTLTISSLQPDDFATYYCQQYNSYLTFGGGTKVEIK SEQ ID NO: 25 (15011 VH DNA sequence)
GAGGTGCAGCTGCTGGAATCCGGAGGAGGACTGGTCCAGCCAGGTGGATCCCTGCGACTGAGCT
GCGCCGCTTCTGGCTTCGACTTTAGAAGCTACGCAATGATGTGGGTCCGCCAGGCACCAGGAA
GGGACTGGAGTGGGTGGGAGGGATCAACGGTGAAGTCGGTGGCTCTAATACATACTATGCACCT
GCCGTCAAGGGAAGGGCTACTATTAGTCGGGACAACTCAAAAAATACCCTGTATCTGCAAATGA
ACAGTCTGAGGGCCGAGGATACCGCCGTGTACTATTGCGTGAAAGGTGCTGGCGCATGCGGCAT
CTGTAATGACGATATTGATGCATGGGGACAGGGGACCCTGGTGACAGTCTCGAGT SEQ ID NO: 26 (15011 VL DNA sequence)
AGTTATGAGCTGACTCAGGACCCAGCAGTGTCAGTCGCCCTGGGCCAGACAGTGAGAATCACTT
GCAGTGGGGCTGGTTCATATGCAGGCTCCTACTATTACGGATGGCACCAGCAGAAGCCCGGACA
GGCACCTGTGACAGTCATCTACGACAACGATAAAAGGCCAAGCAATATTCCCGACCGGTTCTCT
GGGTCCAGCTCTGGTAACACCGCCTCCCTGACCATTACTGGGGCCCAGGCTGAGGACGAAGCTG
ATTATTACTGTGGCTCTACAAACGATAATGACGATGGCGGACTGTTTGGCTCCGGAACTAAGGT
CACCGTCCTA SEQ ID NO: 27 (15011 VH protein sequence)
EVQLLESGGGLVQPGGSLRLSCAASGFDFRSYAMMWVRQAPGKGLEWVGGINGEVGGSNTYYAP
AVKGRATISRDNSKNTLYLQMNSLRAEDTAVYYCVKGAGACGICNDDIDAWGQGTLVTVSS SEQ ID NO: 28 (15011 VL protein sequence)
SYELTQDPAVSVALGQTVRITCSGAGSYAGSYYYGWHQQKPGQAPVTVIYDNDKRPSNIPDRFS
GSSSGNTASLTITGAQAEDEADYYCGSTNDNDDGGLFGSGTKVTVL Constant region DNA and protein sequences
SEQ ID NO: 29 (IgHC constant region DNA sequence)
GCCTCCACCAAGGGCCCATCGGTCTTCCCCCTGGCACCCTCCTCCAAGAGCACCTCTGGGGGCA
CAGCGGCCCTGGGCTGCCTGGTCAAGGACTACTTCCCCGAACCGGTGACGGTGTCGTGGAACTC
AGGCGCCCTGACCAGCGGCGTGCACACCTTCCCGGCTGTCCTACAGTCCTCAGGACTCTACTCC
CTCAGCAGCGTGGTGACCGTGCCCTCCAGCAGCTTGGGCACCCAGACCTACATCTGCAACGTGA
ATCACAAGCCCAGCAACACCAAGGTGGACAAGAGAGTTGAGCCCAAATCTTGTGACAAAACTCA
CACATGCCCACCGTGCCCAGCACCTGAAGCCGCGGGGGACCGTCAGTCTTCCTCTTCCCCCCA
AAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAA
GACAAAGCCGCGGGAGGAGCAGTACAACAGCACGTACCGTGTGGTCAGCGTCCTCACCGTCCTG
CACCAGGACTGGCTGAATGGCAAGGAGTACAAGTGCAAGGTCTCCAACAAAGCCCTCCCAGCCC
CCATCGAGAAAACCATCTCCAAAGCCAAAGGGCAGCCCCGAGAACCACAGGTGTACACCCTGCC
CCCATCCCGGGAGGAGATGACCAAGAACCAGGTCAGCCTGACCTGCCTGGTCAAAGGCTTCTAT
CCCAGCGACATCGCCGTGGAGTGGGAGAGCAATGGGCAGCCGGAGAACAACTACAAGACCACGC
CTCCCGTGCTGGACTCCGACGGCTCCTTCTTCCTCTATAGCAAGCTCACCGTGGACAAGAGCAG
GTGGCAGCAGGGGAACGTCTTCTCATGCTCCGTGATGCATGAGGCTCTGCACAACCACTACACG
CAGAAGAGCCTCTCCCTGTCCCCGGGTAAA
```

Sequence List

SEQ ID NO: 30 (IgHC constant region protein sequence)
ASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPAPEAAGGPSVFLFPP
KPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHYT
QKSLSLSPGK SEQ ID NO: 31 (IgLC constant region DNA sequence)
GGCCAGCCCAAGGCCAACCCCACTGTCACTCTGTTCCCGCCCTCCTCTGAGGAGCTCCAAGCCA
ACAAGGCCACACTAGTGTGTCTGATCAGTGACTTCTACCCGGGAGCTGTGACAGTGGCCTGGAA
GGCAGATGGCAGCCCCGTCAAGGCGGGAGTGGAGACCACCAAACCCTCCAAACAGAGCAACAAC
AAGTACGCGGCCAGCAGCTACCTGAGCCTGACGCCCGAGCAGTGGAAGTCCCACAGAAGCTACA
GCTGCCAGGTCACGCATGAAGGGAGCACCGTGGAGAAGACAGTGGGCCCTACAGAATGTTCA SEQ ID NO: 32 (IgLC constant region protein sequence)
GQPKANPTVTLFPPSSEELQANKATLVCLISDFYPGAVTVAWKADGSPVKAGVETTKPSKQSNN
KYAASSYLSLTPEQWKSHRSYSCQVTHEGSTVEKTVAPTECS SEQ ID NO: 33 (IgKC constant region DNA sequence)
CGTACGGTGGCTGCACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAAGTACAGTGGAAGGT
GGATAACGCCCTCCAATCGGGTAACTCGCAGGAGAGTGTCACAGAGCAGGACAGCAAGGACAGC
ACCTACAGCCTCAGCAGCACCCTGACGCTGAGCAAAGCAGACTACGAGAAACACAAAGTCTACG
CCTGCGAAGTCACCCATCAGGGCCTGAGCTCGCCCGTCACAAAGAGCTTCAACAGGGGAGAGTG
T SEQ ID NO: 34 (IgKC constant region protein sequence)
RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC

SEQ ID NO: 35 (15646/15723 H-CDR1)
GGSFSGYY

SEQ ID NO: 36 (15646 H-CDR2)
INHRGST

SEQ ID NO: 37 (15646 H-CDR3)
CTRGEEWESLFFDYW

SEQ ID NO: 38 (15646 L-CDR1)
QSISSY

SEQ ID NO: 39 (15646 L-CDR2)
GAS

SEQ ID NO: 40 (15646/15532/15723/15431 L-CDR3)
CQQRSNWPLTF

SEQ ID NO: 41 (15532 H-CDR1)
GESFSGYY

SEQ ID NO: 42 (15532/15723 H-CDR2)
INHSGST

SEQ ID NO: 43 (15532 H-CDR3)
CARGWDLLDWNDYWNEYW

SEQ ID NO: 44 (15532/15723/15431 L-CDR1)
QSVSSY

SEQ ID NO: 45 (15532/15431 L-CDR2)
DAS

SEQ ID NO: 46 (15723 H-CDR3)
CARGEDWGESFFDYW

SEQ ID NO: 47 (15723/15595 L-CDR2)
AAS

SEQ ID NO: 48 (15595 H-CDR1)
GYSLTEIS

SEQ ID NO: 49 (15595 H-CDR2)
FDPEDGET

| Sequence List |
| --- |

SEQ ID NO: 50 (15595 H-CDR3)
CATGGWGPNWFDPW

SEQ ID NO: 51 (15595 L-CDR1)
QGISSW

SEQ ID NO: 52 (15595 L-CDR3)
CQQANSFPFTF

SEQ ID NO: 53 (15431 H-CDR1)
GDSVSSNSA

SEQ ID NO: 54 (15431 H-CDR2)
TYYRSKW

SEQ ID NO: 55 (15431 H-CDR3)
CARDDDWNDFDYW

SEQ ID NO: 56 (15572 H-CDR1)
GDSISSSSYY

SEQ ID NO: 57 (15572 H-CDR2)
IFYSGNT

SEQ ID NO: 58 (15572 H-CDR3)
CAREDDFLTDYYGAFDIW

SEQ ID NO: 59 (15572 L-CDR1)
QSISSW

SEQ ID NO: 60 (15572 L-CDR2)
KAS

SEQ ID NO: 61 (15572 L-CDR3)
CQQYNSYLTF

SEQ ID NO: 62 (15011 H-CDR1)
GFDFRSYA

SEQ ID NO: 63 (15011 H-CDR2)
INGEVGGSNT

SEQ ID NO: 64 (15011 H-CDR3)
CVKGAGACG1CNDDIDAW

SEQ ID NO: 65 (15011 L-CDR1)
GSYAGSY

SEQ ID NO: 66 (15011 L-CDR2)
DND

SEQ ID NO: 67 (15011 L-CDR3)
CGSTNDNDDGGLF

SEQ ID NO: 68 (human LAG-3)
MWEAQFLGLLFLQPLWVAPVKPLQPGAEVPVVWAQEGAPAQLPCSPTIPLQDLSLLRRAG
VTWQHQPDSGPPAAAPGHPLAPGPHPAAPSSWGPRPRRYTVLSVGPGGLRSGRLPLQPRV
QLDERGRQRGDFSLWLRPARRADAGEYRAAVHLRDRALSCRLRLRLGQASMTASPPGSLR
ASDWVILNCSFSRPDRPASVHWFRNRGQGRVPVRESPHHHLAESFLFLPQVSPMDSGPWG
CILTYRDGFNVSIMYNLTVLGLEPPTPLTVYAGAGSRVGLPCRLPAGVGTRSFLTAKWTP
PGGGPDLLVTGDNGDFTLRLEDVSQAQAGTYTCHIHLQEQQLNATVTLAIITVTPKSFGS
PGSLGKLLCEVTPVSGQERFVWSSLDTPSQRSFSGPWLEAQEAQLLSQPWQCQLYQGERL
LGAAVYFTELSSPGAQRSGRAPGALPAGHLLLFLILGVLSLLLLVTGAFGFHLWRRQWRP
RRFSALEQGIHPPQAQSKIEELEQEPEPEPEPEPEPEPEPEPEQL SEQ ID NO: 69 (cynomolgus LAG-3)
MWEAQFLGLLFLQPLWVAPVKPPQPGAEISVVWAQEGAPAQLPCSPTIPLQDLSLLRRAGVTWQHQPDSG
PPAXAPGHPPVPGHRPAAPYSWGPRPRRYTVLSVGPGGLRSGRLPLQPRVQLDERGRQRGDFSLWLRPAR
RADAGEYRATVHLRDRALSCRLRLRVGQASMTASPPGSLRTSDWVILNCSFSRPDRPASVHWFRSRGQGR
VPVQGSPHHHLAESFLFLPHVGPMDSGLWGCILTYRDGFNVSIMYNLTVLGLEPATPLTVYAGAGSRVEL
PCRLPPAVGTQSFLTAKWAPPGGGPDLLVAGDNGDFTLRLEDVSQAQAGTYICHIRLQGQQLNATVTLAI
ITVTPKSFGSPGSLGKLLCEVTPASGQEHFVWSPLNTPSQRSFSGPWLEAQEAQLLSQPWQCQLHQGERL
LGAAVYFTELSSPGAQRSGRAPGALRAGHLPLFLILGVLFLLLLVTGAFGFHLWRRQWRPRRFSALEQGI
HPPQAQSKIEELEQEPELEPEPELERELGPEPEPGPEPEPEQL Sequence List SEQ ID NO: 70 (rat LAG-3)
MRQDLFLDLLLLQLLWEAPVVSSGPGKELSVVWAQEGAPVHLPCSLEFPHLDPNFLRRGW
VTWQHRPDSDQPASIPALDLLQGMPSTRRHPPHRYTVLSVAPGGLRSGRQPLLSHVQLEK
RGPQRGDFSLWLRPATRKDAGEYHAFVRLPDRDFSCSLRLRVGQASMIASPPGTLKPSDW
VILNCSFSRPDRPVSVHWFQGQSRVPVHNSPRHYLAESFLLLPQVSPLDSGTWGCVLTYR
DGFNVSITYNLKVQGLEPVAPLTVYAAEGSRVELPCHLPPWGTPSLLIAKWTPPGGGPE
LPVTGKSGNFTLQLENVGRAQAGTYTCSIHLQGRQLSAAVTLAVITVTPKSFGLPGSPQK
LLCEVVPASGEGRFVWRPLSDLSRSSLGPVLELQEAKLLAEQWQCQLYEGQKLLGATVYT
AESSSGAWSAKRISGDLKGGHLFLSLILGALALFLLVTGAFGFHLWRRQLLRRRFSALEH
GIRPPPVQSKIEELEREPETEMEPETEPDPEPQPEPELEPESRQL SEQ ID NO: 71 (dog LAG-3)
MWEVQFLVLLLLQLLWVAPVAAPGSGTEVQWWAQEGAPVQLPCSPTIPLQDVSLLRNAG
VTWYHLPESGPAAPALSLRPAAPSARGPGPRSYVVLMRAPGGLRSGLVPTVNALALNSPG
PTRFSLALQTVISLPHSWLFPGPSSLPGQPLASCWPSPHVGVGCVCEHPPFIHLTLLPAR
QSPLLFLLPSLQPQCSASLYLSLSASTLASSFPGLEPSGPLTVYTGAGSRVGLPCRLPPG
VGTQSFLTAKWTPPGGGPDLLVAGDDGNFTLQLEVVNQAQAGTYTCIHLQGQQLSTTVT
LAVITVTPKSSGLPGNLRKLLCEVTPASGQERFVWSPLDKQSWRGSPGPCLEMQETRLLS
QPWQCHVYQAERLLGTAVYLIDPAGPGAQRSGRAQGVLKTGHLSLLLILGILFLLLLMTG
AFGFQLWRRQWRPRRFSALELGTHPPQAQSKIGELEQEPELELEPEPELEPEPEPE SEQ ID NO: 72 (mouse LAG-3)
MREDLLLGFLLLGLLWEAPVVSSGPGKELPVVWAQEGAPVHLPCSLKSPNLDPNFLRRGG
VIWQHQPDSGQPTPIPALDLHQGMPSPRQPAPGRYTVLSVAPGGLRSGRQPLHPHVQLEE
RGLQRGDFSLWLRPALRTDAGEYHATVRLPNRALSCSLRLRVGQASMIASPSGVLKLSDW
VLLNCSFSRPDRPVSVHWFQGQNRVPVYNSPRHFLAETFLLLPQVSPLDSGTWGCVLTYR
DGFNVSITYNLKVGLEPVAPLTVYAAEGSRVELPCHLPPGVGTPSLLIAKWTPPGGGPE
LPVAGKSGNFTLHLEAVGLAQAGTYTCSIHLQGQQLNATVTLAVITVTPKSFGLPGSRGK
LLCEVTPASGKERFVWRPLNNLSRSCPGPVLEIQEARLLAERWQCQLYEGQRLLGATVYA
AESSSGAHSARRISGDLKGGHLVLVLILGALSLFLLVAGAFGFHWWRKQLLLRRFSALEH
GIQPFPAQRKIEELERELETEMGQEPEPEPEPQLEPEPRQL

What is claimed is:

1. Isolated nucleic acid molecule(s) comprising a nucleotide sequence that encodes a heavy chain sequence, and a nucleotide sequence that encodes a light chain sequence, of an anti-LAG-3 antibody or an antigen-binding portion thereof that comprises the H-CDR1-3 and L-CDR1-3 amino acid sequences of:
   a) SEQ ID NOs: 41, 42, 43, 44, 45, and 40, respectively;
   b) SEQ ID NOs: 35, 36, 37, 38, 39, and 40, respectively;
   c) SEQ ID NOs: 35, 42, 46, 44, 47, and 40, respectively;
   d) SEQ ID NOs: 48, 49, 50, 51, 47, and 52, respectively;
   e) SEQ ID NOs: 53, 54, 55, 44, 45, and 40, respectively;
   f) SEQ ID NOs: 56, 57, 58, 59, 60, and 61, respectively; or
   g) SEQ ID NOs: 62, 63, 64, 65, 66, and 67, respectively.

2. Vector(s) comprising the isolated nucleic acid molecule(s) of claim 1, wherein said vector(s) further comprise an expression control sequence.

3. A host cell comprising the isolated nucleic acid molecule(s) of claim 1.

4. A method for producing an anti-LAG-3 antibody or an antigen-binding portion thereof, comprising providing a host cell according to claim 3, culturing said host cell under conditions suitable for expression of the anti-LAG-3 antibody or antigen-binding portion thereof, and isolating the resulting antibody or antigen-binding portion.

5. The isolated nucleic acid molecule(s) of claim 1, wherein the anti-LAG-3 antibody or antigen-binding portion thereof comprises a heavy chain variable domain and a light chain variable domain having the amino acid sequences of:
   a) SEQ ID NOs: 7 and 8, respectively;
   b) SEQ ID NOs: 3 and 4, respectively;
   c) SEQ ID NOs: 11 and 12, respectively;
   d) SEQ ID NOs: 15 and 16, respectively;
   e) SEQ ID NOs: 19 and 20, respectively;
   f) SEQ ID NOs: 23 and 24, respectively; or
   g) SEQ ID NOs: 27 and 28, respectively.

6. The isolated nucleic acid molecule(s) of claim 1, wherein the anti-LAG-3 antibody is of isotype $IgG_1$.

7. The isolated nucleic acid molecule(s) of claim 1, wherein the anti-LAG-3 antibody comprises:
   a) a heavy chain (HC) comprising the amino acid sequences of SEQ ID NOs: 7 and 30 and a light chain (LC) comprising the amino acid sequences of SEQ ID NOs: 8 and 34;
   b) an HC comprising the amino acid sequences of SEQ ID NOs: 3 and 30 and an LC comprising the amino acid sequences of SEQ ID NOs: 4 and 34;
   c) an HC comprising the amino acid sequences of SEQ ID NOs: 11 and 30 and an LC comprising the amino acid sequences of SEQ ID NOs: 12 and 34;
   d) an HC comprising the amino acid sequences of SEQ ID NOs: 15 and 30 and an LC comprising the amino acid sequences of SEQ ID NOs: 16 and 34;
   e) an HC comprising the amino acid sequences of SEQ ID NOs: 19 and 30 and an LC comprising the amino acid sequences of SEQ ID NOs: 20 and 34;
   f) an HC comprising the amino acid sequences of SEQ ID NOs: 23 and 30 and an LC comprising the amino acid sequences of SEQ ID NOs: 24 and 34; or
   g) an HC comprising the amino acid sequences of SEQ ID NOs: 27 and 30 and an LC comprising the amino acid sequences of SEQ ID NOs: 28 and 32.

8. The isolated nucleic acid molecule(s) of claim 1, wherein the anti-LAG-3 antibody or antigen-binding portion thereof has at least one property selected from:
   a) at a concentration of 20 µg/mL, reduces the binding of human LAG-3 to human MHC class II on A375 cells by greater than 85% compared to a negative control antibody as determined by a flow cytometric competition assay;

b) at a concentration of 20 µg/mL, reduces the binding of human LAG-3 to human MHC class II on A375 cells to between 35% and 85% compared to a negative control antibody as determined by a flow cytometric competition assay;
c) blocks binding between human LAG-3 expressed on Jurkat cells and human MHC class II expressed on Raji cells;
d) binds to human LAG-3 with an $EC_{50}$ of 0.1 nM or less as measured by flow cytometry;
e) binds to cynomolgus LAG-3 with an $EC_{50}$ of 0.3 nM or less as measured by flow cytometry;
f) binds to human LAG-3 with a $K_D$ of $3.0 \times 10^{-8}$ M or less as measured by surface plasmon resonance;
g) binds to cynomolgus LAG-3 with a $K_D$ of $1.5 \times 10^{-7}$ M or less as measured by surface plasmon resonance;
h) binds to mouse LAG-3 with a $K_D$ of $3.5 \times 10^{-8}$ M or less as measured by surface plasmon resonance;
i) stimulates IL-2 production in Staphylococcal enterotoxin B (SEB) treated human peripheral blood mononuclear cells (PBMCs);
j) reduces cellular levels of LAG-3 in human T cells;
k) reduces soluble levels of LAG-3 in the culture of human T cells;
l) induces tumor growth regression in vivo;
m) delays tumor growth in vivo; and
n) does not bind to the same epitope of human LAG-3 as antibody 25F7-Lag3.5.

9. Isolated nucleic acid molecule(s) comprising a nucleotide sequence that encodes a heavy chain sequence, and a nucleotide sequence that encodes a light chain sequence, of an anti-LAG-3 antibody or an antigen-binding portion thereof, wherein the antibody or antigen-binding portion comprises the H-CDR1-3 and L-CDR1-3 amino acid sequences of SEQ ID NOs: 41, 42, 43, 44, 45, and 40, respectively.

10. The isolated nucleic acid molecule(s) of claim 9, wherein
the heavy chain variable domain of the anti-LAG-3 antibody or antigen-binding portion thereof is at least 90% identical in sequence to SEQ ID NO: 7, and
the light chain variable domain of the anti-LAG-3 antibody or antigen-binding portion thereof is at least 90% identical in sequence to SEQ ID NO: 8.

11. The isolated nucleic acid molecule(s) of claim 9, wherein the anti-LAG-3 antibody or antigen-binding portion thereof comprises a heavy chain variable domain and a light chain variable domain having the amino acid sequences of SEQ ID NOs: 7 and 8, respectively.

12. The isolated nucleic acid molecule(s) of claim 9, wherein the anti-LAG-3 antibody is of isotype IgG.

13. The isolated nucleic acid molecule(s) of claim 9, wherein the anti-LAG-3 antibody is of isotype $IgG_1$.

14. Vector(s) comprising the isolated nucleic acid molecule(s) of claim 9, wherein said vector(s) further comprise an expression control sequence.

15. A host cell comprising the isolated nucleic acid molecule(s) of claim 9.

16. A method for producing an anti-LAG-3 antibody or an antigen-binding portion thereof, comprising providing a host cell according to claim 15, culturing said host cell under conditions suitable for expression of the anti-LAG-3 antibody or antigen-binding portion thereof, and isolating the resulting antibody or antigen-binding portion.

17. Isolated nucleic acid molecule(s) comprising a nucleotide sequence that encodes a heavy chain sequence, and a nucleotide sequence that encodes a light chain sequence, of an anti-LAG-3 antibody, wherein the antibody comprises a heavy chain with the amino acid sequences of SEQ ID NOs: 7 and 30 and a light chain with the amino acid sequences of SEQ ID NOs: 8 and 34.

18. Vector(s) comprising the isolated nucleic acid molecule(s) of claim 17, wherein said vector(s) further comprise an expression control sequence.

19. A host cell comprising the isolated nucleic acid molecule(s) of claim 17.

20. A method for producing an anti-LAG-3 antibody, comprising providing a host cell according to claim 19, culturing said host cell under conditions suitable for expression of the anti-LAG-3 antibody, and isolating the resulting antibody.

* * * * *

SEQUENCE LISTING

<160> NUMBER OF SEQ ID NOS: 74

<210> SEQ ID NO 1
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
caggtgcagc tgcagcagtg gggtgccggt ctgctgaagc cttctgaaac tctgtctctg    60
acttgtgccg tctatggtgg atcattcagc ggctactatt ggtcctggat caggcagccc   120
cctggcaagg gcctggagtg gatcggcgag atcaaccacc ggggctctac caactacaat   180
ccctctctga agagcagggt gaccatctcc gtggacacat ctaagaatca gttcagcctg   240
aagctgagct ccgtgaccgc cgctgataca gccgtgtact attgcacaag gggggaggaa   300
tgggagtcac tgttctttga ttactggggg caggggacac tggtcacagt ctcgagt     357

<210> SEQ ID NO 2
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
gaaatcgtcc tgacccagtc ccccgccacc ctgagcctga gccccggaga aagagccacc    60

-continued

```
ctgtcctgcc gagcaagcca gtccatcagc tcctatctcg cctggtatca gcagaaacca      120
ggccaggctc cccggctgct gatctacggc gcctccaaca gagctacagg aatcccagcc      180
cgcttcagcg gctccggctc tggcacagac tttaccctga caatctctag cctggagcct      240
gaggatttcg ccgtgtacta ttgccagcag agatctaatt ggccactgac attcggcggc      300
ggcacacggg tggagatcaa g                                                321
```

<210> SEQ ID NO 3
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Arg Gly Glu Glu Trp Glu Ser Leu Phe Phe Asp Tyr Trp Gly Gln Gly
            100                 105                 110

Thr Leu Val Thr Val Ser Ser
        115

<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Arg Val Glu Ile Lys
            100                 105

<210> SEQ ID NO 5
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

```
caggttcagc tgcagcagtg gggcgccggc ctgctgagac caagcgagac cctgtccctg      60
acatgcgccg tgtatggcga gagcttctcc ggctattact ggaactggat ccggcagcct     120
cccggcaagg gcctggagtg gatcggcgag atcaatcact ccggctccac caattacaac     180
ccatccctga gtctcgggt gacaatcagc gtggatacaa gcaagaccca gttcagcctg     240
aagctgagct ccgtgacagc tgccgatacc gccgtgtatt actgcgccag aggctgggac     300
ctgctggatt ggaatgacta ctggaatgag tactggggcc aggggaccct ggtgaccgtc     360
tcgagt                                                                366
```

<210> SEQ ID NO 6
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
gagatcgtgc tgacccagtc ccctgccacc ctgtctctgt ccctggcga gcgggccacc      60
ctgtcctgta gagcttctca gtccgtgtct tcctacctgg cttggtacca gcagaagcca     120
ggacaggccc caagactgct gatctatgac gcttccaatc gggctaccgg catcccagct     180
cgctttagcg gctccggctc cggcaccgac ttcaccctga caatcagctc cctggagcca     240
gaggattttg ccgtgtatta ctgtcagcag aggtccaatt ggccactgac atttggcggc     300
ggcacaaagg ttgagatcaa g                                               321
```

<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Gln Val Gln Leu Gln Gln Trp Gly Ala Gly Leu Leu Arg Pro Ser Glu
 1               5                  10                  15

Thr Leu Ser Leu Thr Cys Ala Val Tyr Gly Glu Ser Phe Ser Gly Tyr
             20                  25                  30

Tyr Trp Asn Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Thr Gln Phe Ser Leu
 65                  70                  75                  80

Lys Leu Ser Ser Val Thr Ala Ala Asp Thr Ala Val Tyr Tyr Cys Ala
                 85                  90                  95
```

Arg Gly Trp Asp Leu Leu Asp Trp Asn Asp Tyr Trp Asn Glu Tyr Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 9
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
caggttcagc tgcagcagtg gggcgctggc ctgctgaagc cctctgagac cctgtctctg      60
acctgtgccg tgtatggcgg cagcttctcc ggctattact ggaactggat ccgccagccc     120
cccggcaagg gcctggagtg gatcggcgag atcaaccact ccggctctac caactacaat     180
ccttctctga gtccagggt gacaatcagc gtggacacca gcaagaacca gtttagcctg     240
aagctgtcca gcgtgacagc tgccgataca gccgtgtatt actgcgccag aggcgaggat     300
tggggcgaga gcttctttga ttactggggc caggggaccc tggtgaccgt ctcgagt       357

<210> SEQ ID NO 10
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
gagatcgtgc tgacccagtc ccctgccacc ctgtctctgt ccctggcga gcgggccacc      60 ctgagctgtc gggcctccca gtccgtgagc tcctacctgg cttggtatca gcagaagcca    120

```
ggacaggccc caagactgct gatctacgcc gcttccaatc gggccaccgg catccccgcc      180
agattttccg gctctggctc cggcaccgat ttcacccctga caatcagctc cctggagcca     240
gaggacttcg ccgtgtacta ctgccagcag aggtctaatt ggccactgac atttggcggc      300
ggcaccaagg ttgagatcaa g                                                321
```

```
<210> SEQ ID NO 11
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11
```

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Asp Trp Gly Glu Ser Phe Phe Asp Tyr Trp Gly Gln Gly
            100                 105                 110

Thr Leu Val Thr Val Ser Ser
        115
```

```
<210> SEQ ID NO 12
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 13
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
caggttcagc tggtgcagtc cggcgctgag gtgaagaagc tggagcttc tgtgaaggtt      60 tcctgtaagg tttccggcta tagcctgacc gagatctcta tgcactgggt acggcaagcc     120
cccggcaagg gcctggagtg gatgggcggc tttgacccag aggatggcga gaccatctac     180
gctcagaggt tcagggggcg cgtgatcatg accgaggata ccagcaccga taccgcctac     240
atggagctgt ccagcctgag atccgaggat accgccgtgt attactgcgc tactggtggc     300
tggggcccca attggttcga tccttgggc caggggaccc tggtgaccgt ctcgagt         357
```

<210> SEQ ID NO 14
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
gacatccaga tgacacagtc tccttcctct gtgagcgcct ctgtgggcga ccgcgtgacc      60
atcacatgcc gcgcttccca ggggatctct tcctggctgg cttggtacca gcagaagccc     120
ggcaaggccc ccaagctgct gatctatgct gccagcagcc tgcagtccgg cgtgccttcc     180
aggtttagcg gctccggctc cggcaccgac tttacactga caatcagctc cctgcagccc     240
gaggattttg ccacctatta ctgtcagcag gcgaattcct tccctttac attcggccct     300 ggcaccaagg ttgatatcaa g                                               321
```

<210> SEQ ID NO 15
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Ser Leu Thr Glu Ile
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Arg Phe
    50                  55                  60

Gln Gly Arg Val Ile Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Trp Gly Pro Asn Trp Phe Asp Pro Trp Gly Gln Gly
            100                 105                 110
```

Thr Leu Val Thr Val Ser Ser
        115

<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 17
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
caggttcagc tgcagcagtc cggccccggc ctggtgaagc caagccagac cctgtctctg      60
acatgcgcca tctccggcga cagcgtgtcc tctaactccg ccgcttggaa ttggatccgg     120
cagtctccat ccagaggcct ggagtggctg ggcagaacct attaccggtc caagtggtac     180
aacgattatg ccgtgtccgt gaagagcaga atcaccatca accctgatac cagcaagaac     240
cagttcagcc tgcagctgaa ttccgtgacc ccagaggata cagccgtgta ttactgtgct     300
agggacgatg attggaatga cttcgattac tggggccagg ggaccctggt gacagtctcg     360
agt                                                                   363

<210> SEQ ID NO 18
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
gagatcgtgc tgacccagtc cccagctaca ctgtccctgt ctccggcga gcgggccacc       60 ctgagctgta gagcttccca gtccgtgtct tcctatctgg cttggtatca gcagaagcca     120

```
ggacaggccc caaggctgct gatctacgac gcctccaata gagccaccgg catcccagct    180
agattttctg ctccggctc cggcaccgat tcacactga ccatctctag cctggagcca      240
gaggattttg ctgtatatta ctgccagcag cgcagcaact ggcccctgac atttggcggc    300
ggcaccaagg ttgagatcaa g                                              321
```

```
<210> SEQ ID NO 19
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Asp Asp Trp Asn Asp Phe Asp Tyr Trp Gly
            100                 105                 110

Gln Gly Thr Leu Val Thr Val Ser Ser
        115                 120

```
<210> SEQ ID NO 20
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

```
<210> SEQ ID NO 21
```

```
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
cagctgcagc tgcaggaaag cggccccggc ctggtgaagc cctctgagac cctgtccctg      60
acatgcaccg tgagcggcga ttccatcagc tcttccagct attactgggg ctggatccgg     120 cagcccccg gcaagggcct ggagtggatc ggcagcatct tctactccgg caatacatat     180
tataatcctt ctctgaagag cagggtgaca atcagcgtgg ataccccaa gaatcagttt     240 agcctgaagc tgagctccgt gacagctgcc gatacagccg tgtattactg cgctagggag     300
gacgattttc tgaccgatta ttacggcgct ttcgacatct ggggccaggg gacaatggtg     360
acagtctcga gt                                                        372

<210> SEQ ID NO 22
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
gatatccaga tgacccagtc tccaagcacc ctgagcgcct ctgtgggcga tcgggtgacc      60
atcacatgtc gggcttctca gtccatcagc agctggctgg cttggtatca gcagaagccc     120
ggcaaggccc caaagctgct gatctacaag gcctcttcca gcgagagcgg cgtgccatcc     180
aggtttagcg gctccggctc cggcaccgag tttaccctga ccatctcttc cctgcagccc     240
gatgactttg ccacctacta ctgtcagcag tacaattcct atctgacatt cggcggcggc     300
accaaggttg agatcaag                                                   318

<210> SEQ ID NO 23
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Phe Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Asp Phe Leu Thr Asp Tyr Tyr Gly Ala Phe Asp
```

```
                100             105             110
Ile Trp Gly Gln Gly Thr Met Val Thr Val Ser Ser
            115             120

<210> SEQ ID NO 24
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Ser Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Leu Thr
                85                  90                  95

Phe Gly Gly Gly Thr Lys Val Glu Ile Lys
            100                 105

<210> SEQ ID NO 25
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gaggtgcagc tgctggaatc cggaggagga ctggtccagc caggtggatc cctgcgactg    60
agctgcgccg cttctggctt cgactttaga agctacgcaa tgatgtgggt ccgccaggca   120
ccaggaaagg gactggagtg ggtgggaggg atcaacggtg aagtcggtgg ctctaataca   180
tactatgcac ctgccgtcaa gggaagggct actattagtc gggacaactc aaaaaatacc   240
ctgtatctgc aaatgaacag tctgagggcc gaggataccg ccgtgtacta ttgcgtgaaa   300
ggtgctggcg catgcggcat ctgtaatgac gatattgatg catggggaca ggggaccctg   360
gtgacagtct cgagt                                                    375

<210> SEQ ID NO 26
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
agttatgagc tgactcagga cccagcagtg tcagtcgccc tgggccagac agtgagaatc    60
acttgcagtg gggctggttc atatgcaggc tcctactatt acggatggca ccagcagaag   120
```

```
cccggacagg cacctgtgac agtcatctac gacaacgata aaaggccaag caatattccc    180
gaccggttct ctgggtccag ctctggtaac accgcctccc tgaccattac tggggcccag    240
gctgaggacg aagctgatta ttactgtggc tctacaaacg ataatgacga tggcggactg    300
tttggctccg gaactaaggt caccgtccta                                     330
```

<210> SEQ ID NO 27
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Arg Ser Tyr
            20                  25                  30

Ala Met Met Trp Val Arg Gln Ala Pro Gly Lys Gly Leu Glu Trp Val
        35                  40                  45

Gly Gly Ile Asn Gly Glu Val Gly Gly Ser Asn Thr Tyr Tyr Ala Pro
    50                  55                  60

Ala Val Lys Gly Arg Ala Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys Gly Ala Gly Ala Cys Gly Ile Cys Asn Asp Asp Ile
            100                 105                 110

Asp Ala Trp Gly Gln Gly Thr Leu Val Thr Val Ser Ser
        115                 120                 125
```

<210> SEQ ID NO 28
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 28

```
Ser Tyr Glu Leu Thr Gln Asp Pro Ala Val Ser Val Ala Leu Gly Gln
1               5                   10                  15

Thr Val Arg Ile Thr Cys Ser Gly Ala Gly Ser Tyr Ala Gly Ser Tyr
            20                  25                  30

Tyr Tyr Gly Trp His Gln Gln Lys Pro Gly Gln Ala Pro Val Thr Val
        35                  40                  45

Ile Tyr Asp Asn Asp Lys Arg Pro Ser Asn Ile Pro Arg Phe Ser
    50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Gly Ser Thr Asn Asp Asn Asp
                85                  90                  95

Asp Gly Gly Leu Phe Gly Ser Gly Thr Lys Val Thr Val Leu
            100                 105                 110
```

<210> SEQ ID NO 29
<211> LENGTH: 990
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaagc cgccggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggaggga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                      990
```

<210> SEQ ID NO 30
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 31
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
ggccagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca acaagtacgc ggccagcagc tacctgagcc tgacgcccga gcagtggaag   240
tcccacagaa gctacagctg ccaggtcacg catgaaggga gcaccgtgga agacagtg     300 gcccctacag aatgttca                                                 318

<210> SEQ ID NO 32
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gly Gln Pro Lys Ala Asn Pro Thr Val Thr Leu Phe Pro Pro Ser Ser
1               5                   10                  15
```

Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                    85                  90                  95

Glu Lys Thr Val Ala Pro Thr Glu Cys Ser
            100                 105

<210> SEQ ID NO 33
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 34
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                    85                  90                  95

Pro Val Thr Lys Ser Phe Asn Arg Gly Glu Cys
            100                 105

<210> SEQ ID NO 35
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Gly Ser Phe Ser Gly Tyr Tyr
1               5

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ile Asn His Arg Gly Ser Thr
1               5

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Cys Thr Arg Gly Glu Glu Trp Glu Ser Leu Phe Phe Asp Tyr Trp
1               5                   10                  15

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gln Ser Ile Ser Ser Tyr
1               5

<210> SEQ ID NO 39
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Ala Ser
1

<210> SEQ ID NO 40
<211> LENGTH: 11
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 40

Cys Gln Gln Arg Ser Asn Trp Pro Leu Thr Phe
1               5                   10

<210> SEQ ID NO 41
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Glu Ser Phe Ser Gly Tyr Tyr
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ile Asn His Ser Gly Ser Thr
1               5

<210> SEQ ID NO 43
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Cys Ala Arg Gly Trp Asp Leu Leu Asp Trp Asn Asp Tyr Trp Asn Glu
1               5                   10                  15

Tyr Trp

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gln Ser Val Ser Ser Tyr
1               5

<210> SEQ ID NO 45
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 45

Asp Ala Ser
1

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Cys Ala Arg Gly Glu Asp Trp Gly Glu Ser Phe Phe Asp Tyr Trp
1               5                   10                  15

<210> SEQ ID NO 47
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Ala Ser
1

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Tyr Ser Leu Thr Glu Ile Ser
1               5

<210> SEQ ID NO 49
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Phe Asp Pro Glu Asp Gly Glu Thr
1               5

<210> SEQ ID NO 50
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Cys Ala Thr Gly Gly Trp Gly Pro Asn Trp Phe Asp Pro Trp
```

<210> SEQ ID NO 51
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Gly Ile Ser Ser Trp
1               5

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Cys Gln Gln Ala Asn Ser Phe Pro Phe Thr Phe
1               5                   10

<210> SEQ ID NO 53
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Asp Ser Val Ser Ser Asn Ser Ala
1               5

<210> SEQ ID NO 54
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Thr Tyr Tyr Arg Ser Lys Trp
1               5

<210> SEQ ID NO 55
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Cys Ala Arg Asp Asp Asp Trp Asn Asp Phe Asp Tyr Trp
1               5                   10

<210> SEQ ID NO 56

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Asp Ser Ile Ser Ser Ser Ser Tyr Tyr
1               5                   10

<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ile Phe Tyr Ser Gly Asn Thr
1               5

<210> SEQ ID NO 58
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Cys Ala Arg Glu Asp Asp Phe Leu Thr Asp Tyr Tyr Gly Ala Phe Asp
1               5                   10                  15

Ile Trp

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Ser Ile Ser Ser Trp
1               5

<210> SEQ ID NO 60
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Lys Ala Ser
1

<210> SEQ ID NO 61
<211> LENGTH: 10
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Cys Gln Gln Tyr Asn Ser Tyr Leu Thr Phe
1               5                   10

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Phe Asp Phe Arg Ser Tyr Ala
1               5

<210> SEQ ID NO 63
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ile Asn Gly Glu Val Gly Gly Ser Asn Thr
1               5                   10

<210> SEQ ID NO 64
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Cys Val Lys Gly Ala Gly Ala Cys Gly Ile Cys Asn Asp Asp Ile Asp
1               5                   10                  15

Ala Trp

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gly Ser Tyr Ala Gly Ser Tyr
1               5

<210> SEQ ID NO 66
<211> LENGTH: 3
<212> TYPE: PRT
<213> ORGANISM: Artificial Sequence
<220> FEATURE:
```

-continued

<221> NAME/KEY: source
<223> OTHER INFORMATION: /note="Description of Artificial Sequence:
      Synthetic peptide"

<400> SEQUENCE: 66

Asp Asn Asp
1

<210> SEQ ID NO 67
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Cys Gly Ser Thr Asn Asp Asn Asp Asp Gly Gly Leu Phe
1               5                   10

<210> SEQ ID NO 68
<211> LENGTH: 525
<212> TYPE: PRT
<213> ORGANISM: Homo sapiens

<400> SEQUENCE: 68

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

-continued

```
Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
        515                 520                 525

<210> SEQ ID NO 69
<211> LENGTH: 533
<212> TYPE: PRT
<213> ORGANISM: Macaca fascicularis
<220> FEATURE:
<221> NAME/KEY: MOD_RES
<222> LOCATION: (74)..(74)
<223> OTHER INFORMATION: Any amino acid

<400> SEQUENCE: 69

Met Trp Glu Ala Gln Phe Leu Gly Leu Leu Phe Leu Gln Pro Leu Trp
1               5                   10                  15

Val Ala Pro Val Lys Pro Pro Gln Pro Gly Ala Glu Ile Ser Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Xaa Ala Pro Gly His Pro Pro
65                  70                  75                  80
```

```
Val Pro Gly His Arg Pro Ala Ala Pro Tyr Ser Trp Gly Pro Arg Pro
                85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
            130                 135                 140

Gly Glu Tyr Arg Ala Thr Val His Leu Arg Asp Arg Ala Leu Ser Cys
145                 150                 155                 160

Arg Leu Arg Leu Arg Val Gly Gln Ala Ser Met Thr Ala Ser Pro Pro
                165                 170                 175

Gly Ser Leu Arg Thr Ser Asp Trp Val Ile Leu Asn Cys Ser Phe Ser
                180                 185                 190

Arg Pro Asp Arg Pro Ala Ser Val His Trp Phe Arg Ser Arg Gly Gln
            195                 200                 205

Gly Arg Val Pro Val Gln Gly Ser Pro His His Leu Ala Glu Ser
            210                 215                 220

Phe Leu Phe Leu Pro His Val Gly Pro Met Asp Ser Gly Leu Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Ala Thr Pro Leu Thr Val Tyr Ala
                260                 265                 270

Gly Ala Gly Ser Arg Val Glu Leu Pro Cys Arg Leu Pro Pro Ala Val
            275                 280                 285

Gly Thr Gln Ser Phe Leu Thr Ala Lys Trp Ala Pro Pro Gly Gly Gly
            290                 295                 300

Pro Asp Leu Leu Val Ala Gly Asp Asn Gly Asp Phe Thr Leu Arg Leu
305                 310                 315                 320

Glu Asp Val Ser Gln Ala Gln Ala Gly Thr Tyr Ile Cys His Ile Arg
                325                 330                 335

Leu Gln Gly Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Ala Ser Gly Gln Glu His Phe Val Trp Ser Pro
370                 375                 380

Leu Asn Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu His Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Arg Ala Gly
            435                 440                 445

His Leu Pro Leu Phe Leu Ile Leu Gly Val Leu Phe Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Leu Glu Pro Glu Pro
```

```
            500                 505                 510
Glu Leu Glu Arg Glu Leu Gly Pro Glu Pro Glu Pro Gly Pro Glu Pro
            515                 520                 525

Glu Pro Glu Gln Leu
            530

<210> SEQ ID NO 70
<211> LENGTH: 525
<212> TYPE: PRT
<213> ORGANISM: Rattus norvegicus

<400> SEQUENCE: 70

Met Arg Gln Asp Leu Phe Leu Asp Leu Leu Leu Gln Leu Leu Trp
1               5                   10                  15

Glu Ala Pro Val Val Ser Ser Gly Pro Gly Lys Glu Leu Ser Val Val
                20                  25                  30

Trp Ala Gln Glu Gly Ala Pro Val His Leu Pro Cys Ser Leu Glu Phe
            35                  40                  45

Pro His Leu Asp Pro Asn Phe Leu Arg Arg Gly Trp Val Thr Trp Gln
        50                  55                  60

His Arg Pro Asp Ser Asp Gln Pro Ala Ser Ile Pro Ala Leu Asp Leu
65                  70                  75                  80

Leu Gln Gly Met Pro Ser Thr Arg Arg His Pro Pro His Arg Tyr Thr
                85                  90                  95

Val Leu Ser Val Ala Pro Gly Gly Leu Arg Ser Gly Arg Gln Pro Leu
            100                 105                 110

Leu Ser His Val Gln Leu Glu Lys Arg Gly Pro Gln Arg Gly Asp Phe
        115                 120                 125

Ser Leu Trp Leu Arg Pro Ala Thr Arg Lys Asp Ala Gly Glu Tyr His
130                 135                 140

Ala Phe Val Arg Leu Pro Asp Arg Asp Phe Ser Cys Ser Leu Arg Leu
145                 150                 155                 160

Arg Val Gly Gln Ala Ser Met Ile Ala Ser Pro Gly Thr Leu Lys
                165                 170                 175

Pro Ser Asp Trp Val Ile Leu Asn Cys Ser Phe Ser Arg Pro Asp Arg
            180                 185                 190

Pro Val Ser Val His Trp Phe Gln Gly Gln Ser Arg Val Pro Val His
        195                 200                 205

Asn Ser Pro Arg His Tyr Leu Ala Glu Ser Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Gln Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Val Val Gly Thr Pro Ser Leu Leu
        275                 280                 285

Ile Ala Lys Trp Thr Pro Pro Gly Gly Gly Pro Glu Leu Pro Val Thr
        290                 295                 300

Gly Lys Ser Gly Asn Phe Thr Leu Gln Leu Glu Asn Val Gly Arg Ala
305                 310                 315                 320

Gln Ala Gly Thr Tyr Thr Cys Ser Ile His Leu Gln Gly Arg Gln Leu
                325                 330                 335
```

-continued

```
Ser Ala Ala Val Thr Leu Ala Val Ile Thr Val Thr Pro Lys Ser Phe
                340                 345                 350

Gly Leu Pro Gly Ser Pro Gln Lys Leu Leu Cys Glu Val Val Pro Ala
            355                 360                 365

Ser Gly Glu Gly Arg Phe Val Trp Arg Pro Leu Ser Asp Leu Ser Arg
        370                 375                 380

Ser Ser Leu Gly Pro Val Leu Glu Leu Gln Glu Ala Lys Leu Leu Ala
385                 390                 395                 400

Glu Gln Trp Gln Cys Gln Leu Tyr Glu Gly Gln Lys Leu Leu Gly Ala
                405                 410                 415

Thr Val Tyr Thr Ala Glu Ser Ser Gly Ala Trp Ser Ala Lys Arg
            420                 425                 430

Ile Ser Gly Asp Leu Lys Gly Gly His Leu Phe Leu Ser Leu Ile Leu
            435                 440                 445

Gly Ala Leu Ala Leu Phe Leu Leu Val Thr Gly Ala Phe Gly Phe His
        450                 455                 460

Leu Trp Arg Arg Gln Leu Leu Arg Arg Arg Phe Ser Ala Leu Glu His
465                 470                 475                 480

Gly Ile Arg Pro Pro Val Gln Ser Lys Ile Glu Glu Leu Glu Arg
                485                 490                 495

Glu Pro Glu Thr Glu Met Glu Pro Glu Thr Glu Pro Asp Pro Glu Pro
            500                 505                 510

Gln Pro Glu Pro Glu Leu Glu Pro Glu Ser Arg Gln Leu
            515                 520                 525

<210> SEQ ID NO 71
<211> LENGTH: 476
<212> TYPE: PRT
<213> ORGANISM: Canis familiaris

<400> SEQUENCE: 71

Met Trp Glu Val Gln Phe Leu Val Leu Leu Leu Gln Leu Leu Trp
1               5                   10                  15

Val Ala Pro Val Ala Ala Pro Gly Ser Gly Thr Glu Val Gln Val Val
                20                  25                  30

Trp Ala Gln Glu Gly Ala Pro Val Gln Leu Pro Cys Ser Pro Thr Ile
            35                  40                  45

Pro Leu Gln Asp Val Ser Leu Leu Arg Asn Ala Gly Val Thr Trp Tyr
        50                  55                  60

His Leu Pro Glu Ser Gly Pro Ala Ala Pro Ala Leu Ser Leu Arg Pro
65                  70                  75                  80

Ala Ala Pro Ser Ala Arg Gly Pro Gly Pro Arg Ser Tyr Val Val Leu
                85                  90                  95

Met Arg Ala Pro Gly Gly Leu Arg Ser Gly Leu Val Pro Thr Val Asn
            100                 105                 110

Ala Leu Ala Leu Asn Ser Pro Gly Pro Thr Arg Phe Ser Leu Ala Leu
        115                 120                 125

Gln Thr Val Ile Ser Leu Pro His Ser Trp Leu Phe Pro Gly Pro Ser
    130                 135                 140

Ser Leu Pro Gly Gln Pro Leu Ala Ser Cys Trp Pro Ser Pro His Val
145                 150                 155                 160

Gly Val Gly Cys Val Cys Glu His Pro Pro Phe Ile His Leu Thr Leu
                165                 170                 175

Leu Pro Ala Arg Gln Ser Pro Leu Leu Phe Leu Leu Pro Ser Leu Gln
            180                 185                 190
```

```
Pro Gln Cys Ser Ala Ser Leu Tyr Leu Ser Leu Ser Ala Ser Thr Leu
        195                 200                 205

Ala Ser Ser Phe Pro Gly Leu Glu Pro Ser Gly Pro Leu Thr Val Tyr
    210                 215                 220

Thr Gly Ala Gly Ser Arg Val Gly Leu Pro Cys Arg Leu Pro Pro Gly
225                 230                 235                 240

Val Gly Thr Gln Ser Phe Leu Thr Ala Lys Trp Thr Pro Gly Gly
                245                 250                 255

Gly Pro Asp Leu Leu Val Ala Gly Asp Asp Gly Asn Phe Thr Leu Gln
            260                 265                 270

Leu Glu Val Val Asn Gln Ala Gln Ala Gly Thr Tyr Thr Cys His Ile
            275                 280                 285

His Leu Gln Gly Gln Gln Leu Ser Thr Thr Val Thr Leu Ala Val Ile
        290                 295                 300

Thr Val Thr Pro Lys Ser Ser Gly Leu Pro Gly Asn Leu Arg Lys Leu
305                 310                 315                 320

Leu Cys Glu Val Thr Pro Ala Ser Gly Gln Glu Arg Phe Val Trp Ser
                325                 330                 335

Pro Leu Asp Lys Gln Ser Trp Arg Gly Ser Pro Gly Pro Cys Leu Glu
            340                 345                 350

Met Gln Glu Thr Arg Leu Leu Ser Gln Pro Trp Gln Cys His Val Tyr
        355                 360                 365

Gln Ala Glu Arg Leu Leu Gly Thr Ala Val Tyr Leu Ile Asp Pro Ala
    370                 375                 380

Gly Pro Gly Ala Gln Arg Ser Gly Arg Ala Gln Gly Val Leu Lys Thr
385                 390                 395                 400

Gly His Leu Ser Leu Leu Leu Ile Leu Gly Ile Leu Phe Leu Leu Leu
                405                 410                 415

Leu Met Thr Gly Ala Phe Gly Phe Gln Leu Trp Arg Arg Gln Trp Arg
            420                 425                 430

Pro Arg Arg Phe Ser Ala Leu Glu Leu Gly Thr His Pro Pro Gln Ala
        435                 440                 445

Gln Ser Lys Ile Gly Glu Leu Glu Gln Glu Pro Glu Leu Glu Leu Glu
    450                 455                 460

Pro Glu Pro Glu Leu Glu Pro Glu Pro Glu
465                 470                 475

<210> SEQ ID NO 72
<211> LENGTH: 521
<212> TYPE: PRT
<213> ORGANISM: Mus musculus

<400> SEQUENCE: 72

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Val Ile Trp Gln
        50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
```

-continued

```
                    85                  90                  95
Val Leu Ser Val Ala Pro Gly Gly Leu Arg Ser Gly Arg Gln Pro Leu
                100                 105                 110

His Pro His Val Gln Leu Glu Glu Arg Gly Leu Gln Arg Gly Asp Phe
                115                 120                 125

Ser Leu Trp Leu Arg Pro Ala Leu Arg Thr Asp Ala Gly Glu Tyr His
            130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
                180                 185                 190

Pro Val Ser Val His Trp Phe Gln Gly Gln Asn Arg Val Pro Val Tyr
                195                 200                 205

Asn Ser Pro Arg His Phe Leu Ala Glu Thr Phe Leu Leu Leu Pro Gln
            210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
                260                 265                 270

Glu Leu Pro Cys His Leu Pro Pro Gly Val Gly Thr Pro Ser Leu Leu
            275                 280                 285

Ile Ala Lys Trp Thr Pro Pro Gly Gly Gly Pro Glu Leu Pro Val Ala
            290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
                340                 345                 350

Gly Leu Pro Gly Ser Arg Gly Lys Leu Leu Cys Glu Val Thr Pro Ala
            355                 360                 365

Ser Gly Lys Glu Arg Phe Val Trp Arg Pro Leu Asn Asn Leu Ser Arg
            370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
                420                 425                 430

Ile Ser Gly Asp Leu Lys Gly Gly His Leu Val Leu Val Leu Ile Leu
            435                 440                 445

Gly Ala Leu Ser Leu Phe Leu Leu Val Ala Gly Ala Phe Gly Phe His
            450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
            500                 505                 510
```

```
Gln Leu Glu Pro Glu Pro Arg Gln Leu
        515                 520

<210> SEQ ID NO 73
<211> LENGTH: 6
<212> TYPE: PRT
<213> ORGANISM: Unknown
<220> FEATURE:
<221> NAME/KEY: source
<223> OTHER INFORMATION: /note="Description of Unknown:
      LAG-3 motif"

<400> SEQUENCE: 73

Lys Ile Glu Glu Leu Glu
1               5

<210> SEQ ID NO 74
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Gly Gly Gly Gly Ser Gly Gly Gly Gly Ser Gly Gly Gly Gly Ser
1               5                   10                  15
```

UNITED STATES PATENT AND TRADEMARK OFFICE
CERTIFICATE OF CORRECTION

PATENT NO.        : 11,834,503 B2
APPLICATION NO.   : 17/834497
DATED             : December 5, 2023
INVENTOR(S)       : Grandal et al.

It is certified that error appears in the above-identified patent and that said Letters Patent is hereby corrected as shown below:

In the Specification

Column 61, Lines 3-9 should appear as follows:
SEQ ID NO: 30 (IgHC constant region protein sequence)
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMH
EALHNHYTQKSLSLSPGK Column 61, Lines 11-16 should appear as follows:
SEQ ID NO: 31 (IgLC constant region DNA sequence)
GGCCAGCCCAAGGCCAACCCCACTGTCACTCTGTTCCCGCCCTCCTCTGAGGAGCTCCAA
GCCAACAAGGCCACACTAGTGTGTCTGATCAGTGACTTCTACCCGGGAGCTGTGACAGTG
GCCTGGAAGGCAGATGGCAGCCCCGTCAAGGCGGGAGTGGAGACCACCAAACCCTCCAA
ACAGAGCAACAACAAGTACGCGGCCAGCAGCTACCTGAGCCTGACGCCCGAGCAGTGGA
AGTCCCACAGAAGCTACAGCTGCCAGGTCACGCATGAAGGGAGCACCGTGGAGAAGACA
GTGGCCCCTACAGAATGTTCA Column 61, Lines 22-28 should appear as follows:
SEQ ID NO: 33 (IgKC constant region DNA sequence)
CGTACGGTGGCTGCACCATCTGTCTTCATCTTCCCGCCATCTGATGAGCAGTTGAAATCTG
GAACTGCCTCTGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACGA
GAAACACAAAGTCTACGCCTGCGAAGTCACCCATCAGGGCCTGAGCTCGCCCGTCACAA
AGAGCTTCAACAGGGGAGAGTGT Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 11,834,503 B2

Column 63, Lines 44-45 should appear as follows:
SEQ ID NO: 64 (15011 H-CDR3)
CVKGAGACGICNDDIDAW Column 65, Lines 2-11 should appear as follows:
SEQ ID NO: 70 (rat LAG-3)
MRQDLFLDLLLLQLLWEAPVVSSGPGKELSVVWAQEGAPVHLPCSLEFPHLDPNFLRRGW
VTWQHRPDSDQPASIPALDLLQGMPSTRRHPPHRYTVLSVAPGGLRSGRQPLLSHVQLEK
RGPQRGDFSLWLRPATRKDAGEYHAFVRLPDRDFSCSLRLRVGQASMIASPPGTLKPSDW
VILNCSFSRPDRPVSVHWFQGQSRVPVHNSPRHYLAESFLLLPQVSPLDSGTWGCVLTYR
DGFNVSITYNLKVQGLEPVAPLTVYAAEGSRVELPCHLPPVVGTPSLLIAKWTPPGGGPE
LPVTGKSGNFTLQLENVGRAQAGTYTCSIHLQGRQLSAAVTLAVITVTPKSFGLPGSPQK
LLCEVVPASGEGRFVWRPLSDLSRSSLGPVLELQEAKLLAEQWQCQLYEGQKLLGATVYT
AESSSGAWSAKRISGDLKGGHLFLSLILGALALFLLVTGAFGFHLWRRQLLRRRFSALEH
GIRPPPVQSKIEELEREPETEMEPETEPDPEPQPEPELEPESRQL Column 65, Lines 13-21 should appear as follows:
SEQ ID NO: 71 (dog LAG-3)
MWEVQFLVLLLLQLLWVAPVAAPGSGTEVQVVWAQEGAPVQLPCSPTIPLQDVSLLRNAG
VTWYHLPESGPAAPALSLRPAAPSARGPGPRSYVVLMRAPGGLRSGLVPTVNALALNSPG
PTRFSLALQTVISLPHSWLFPGPSSLPGQPLASCWPSPHVGVGCVCEHPPFIHLTLLPAR
QSPLLFLLPSLQPQCSASLYLSLSASTLASSFPGLEPSGPLTVYTGAGSRVGLPCRLPPG
VGTQSFLTAKWTPPGGGPDLLVAGDDGNFTLQLEVVNQAQAGTYTCHIHLQGQQLSTTVT
LAVITVTPKSSGLPGNLRKLLCEVTPASGQERFVWSPLDKQSWRGSPGPCLEMQETRLLS
QPWQCHVYQAERLLGTAVYLIDPAGPGAQRSGRAQGVLKTGHLSLLLILGILFLLLLMTG
AFGFQLWRRQWRPRRFSALELGTHPPQAQSKIGELEQEPELELEPEPELEPEPEPE